(12) United States Patent
Eldridge et al.

(10) Patent No.: US 12,097,496 B2
(45) Date of Patent: *Sep. 24, 2024

(54) MIXING AND MICROFLUIDIC APPARATUSES RELATED THERETO

(71) Applicant: Nutcracker Therapeutics, Inc., Emeryville, CA (US)

(72) Inventors: Benjamin Eldridge, Danville, CA (US); Ximiao Wen, Hayward, CA (US)

(73) Assignee: Nutcracker Therapeutics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,521

(22) Filed: May 19, 2023

(65) Prior Publication Data

US 2023/0356221 A1   Nov. 9, 2023

Related U.S. Application Data

(63) Continuation of application No. 17/727,937, filed on Apr. 25, 2022, now Pat. No. 11,724,257, which is a
(Continued)

(51) Int. Cl.
*B01L 3/00* (2006.01)
*A61K 31/7105* (2006.01)
(Continued)

(52) U.S. Cl.
CPC ...... *B01L 3/50273* (2013.01); *A61K 31/7105* (2013.01); *B01F 23/405* (2022.01);
(Continued)

(58) Field of Classification Search
CPC ............. B01L 3/50273; A61K 31/7105; B01F 2215/0472
See application file for complete search history.

(56) References Cited

U.S. PATENT DOCUMENTS

| 9,574,167 B2 | 2/2017 | Lee et al. |
| 11,278,895 B2 | 3/2022 | Eldridge et al. |

(Continued)

FOREIGN PATENT DOCUMENTS

| EP | 0870541 A2 | 10/1998 |
| EP | 2089144 B1 | 10/2011 |

(Continued)

OTHER PUBLICATIONS

Chen, Delai, et al. "Rapid discovery of potent siRNA-containing lipid nanoparticles enabled by controlled microfluidic formulation." *Journal of the American Chemical Society* 134.16 (2012): 6948-6951.
(Continued)

*Primary Examiner* — Anshu Bhatia
(74) *Attorney, Agent, or Firm* — Frost Brown Todd LLP

(57) ABSTRACT

The application relates to microfluidic apparatus and methods of use thereof. Provided in one example is a microfluidic device comprising: a first fluidic input and a second fluidic input; and a fluidic intersection channel to receive fluid from the first fluidic input and the second fluidic input, wherein the fluidic intersection channel opens into a first mixing chamber on an upper region of a first side of the first mixing chamber, wherein the first mixing chamber has a length, a width, and a depth, wherein the depth is greater than about 1.5 times a depth of the fluidic intersection channel; an outlet channel on an upper region of a second side of the first mixing chamber, wherein the outlet channel has a depth that is less than the depth of the first mixing chamber, and wherein an opening of the outlet channel is offset along a width of the second side of the first mixing chamber relative to the fluidic intersection.

20 Claims, 28 Drawing Sheets

Related U.S. Application Data continuation of application No. 17/360,263, filed on Jun. 28, 2021, now Pat. No. 11,325,122, which is a continuation of application No. PCT/US2020/066541, filed on Dec. 22, 2020.

(60) Provisional application No. 62/953,102, filed on Dec. 23, 2019.

(51) Int. Cl.
  *B01F 23/40* (2022.01)
  *B01F 33/301* (2022.01)
  *B01F 101/22* (2022.01)

(52) U.S. Cl.
  CPC .... *B01F 33/3017* (2022.01); *B01L 3/502738* (2013.01); *B01F 2101/22* (2022.01); *B01F 2215/0472* (2013.01); *B01L 2300/0854* (2013.01); *B01L 2300/0858* (2013.01); *B01L 2300/0867* (2013.01); *B01L 2300/0877* (2013.01); *B01L 2300/0883* (2013.01); *B01L 2400/0478* (2013.01); *B01L 2400/0487* (2013.01); *B01L 2400/06* (2013.01)

(56) References Cited

U.S. PATENT DOCUMENTS

| | | | | |
|---|---|---|---|---|
| 11,325,122 B2* | 5/2022 | Eldridge | ................ | B01F 33/30 |
| 11,571,693 B2 | 2/2023 | Eldridge et al. | | |
| 11,724,257 B2* | 8/2023 | Eldridge | ................ | B01F 25/10 |
| | | | | 514/44 R |
| 2001/0048900 A1 | 12/2001 | Bardell et al. | | |
| 2005/0041525 A1 | 2/2005 | Pugia et al. | | |
| 2006/0078471 A1 | 4/2006 | Witty et al. | | |
| 2009/0145485 A1 | 6/2009 | Smith et al. | | |
| 2011/0155667 A1 | 6/2011 | Charest et al. | | |
| 2012/0103427 A1 | 5/2012 | Park et al. | | |
| 2012/0218857 A1 | 8/2012 | Ocola et al. | | |
| 2019/0168221 A1 | 6/2019 | Sollier et al. | | |
| 2021/0040472 A1 | 2/2021 | Deutsch et al. | | |

FOREIGN PATENT DOCUMENTS

| | | |
|---|---|---|
| JP | 2009-183876 A | 8/2009 |
| KR | 20090106089 A | 10/2009 |
| TW | 200533413 A | 10/2005 |
| WO | WO 2010/077322 A1 | 7/2010 |

OTHER PUBLICATIONS

Extended European Search Report dated Jan. 2, 2024, for Application No. 20907142.2, 9 pages.

International Search Report and Written Opinion dated Apr. 27, 2021, for International Application No. PCT/US2020/066541, 14 pages.

Taiwan First Office Action dated Mar. 7, 2024, for Application No. 109145527, 9 pages.

* cited by examiner

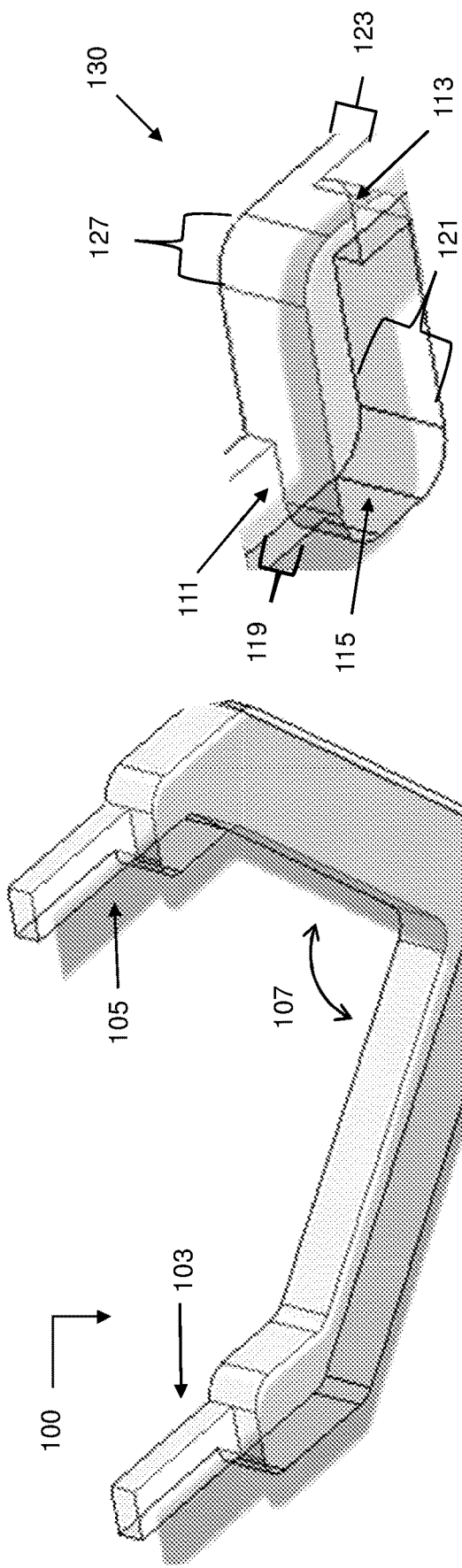
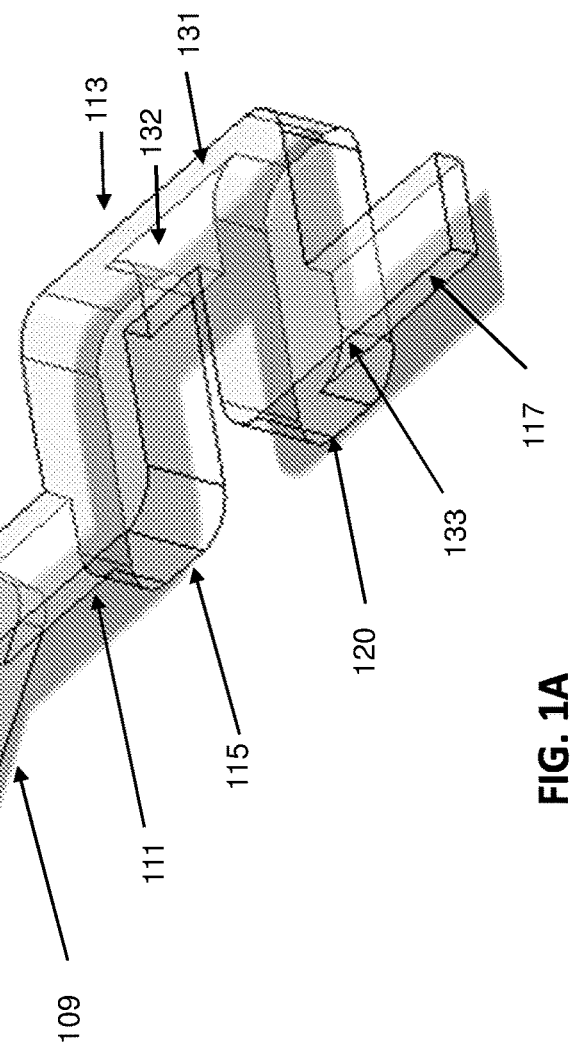
FIG. 1A
FIG. 1B

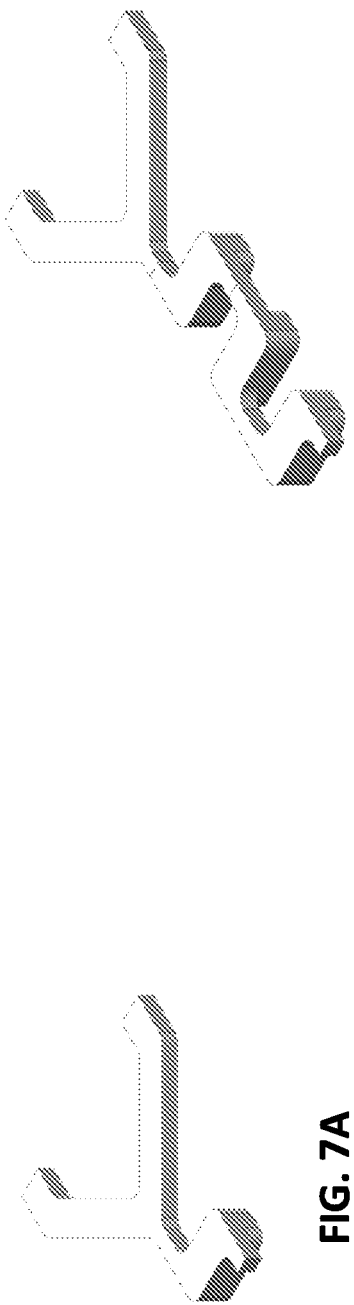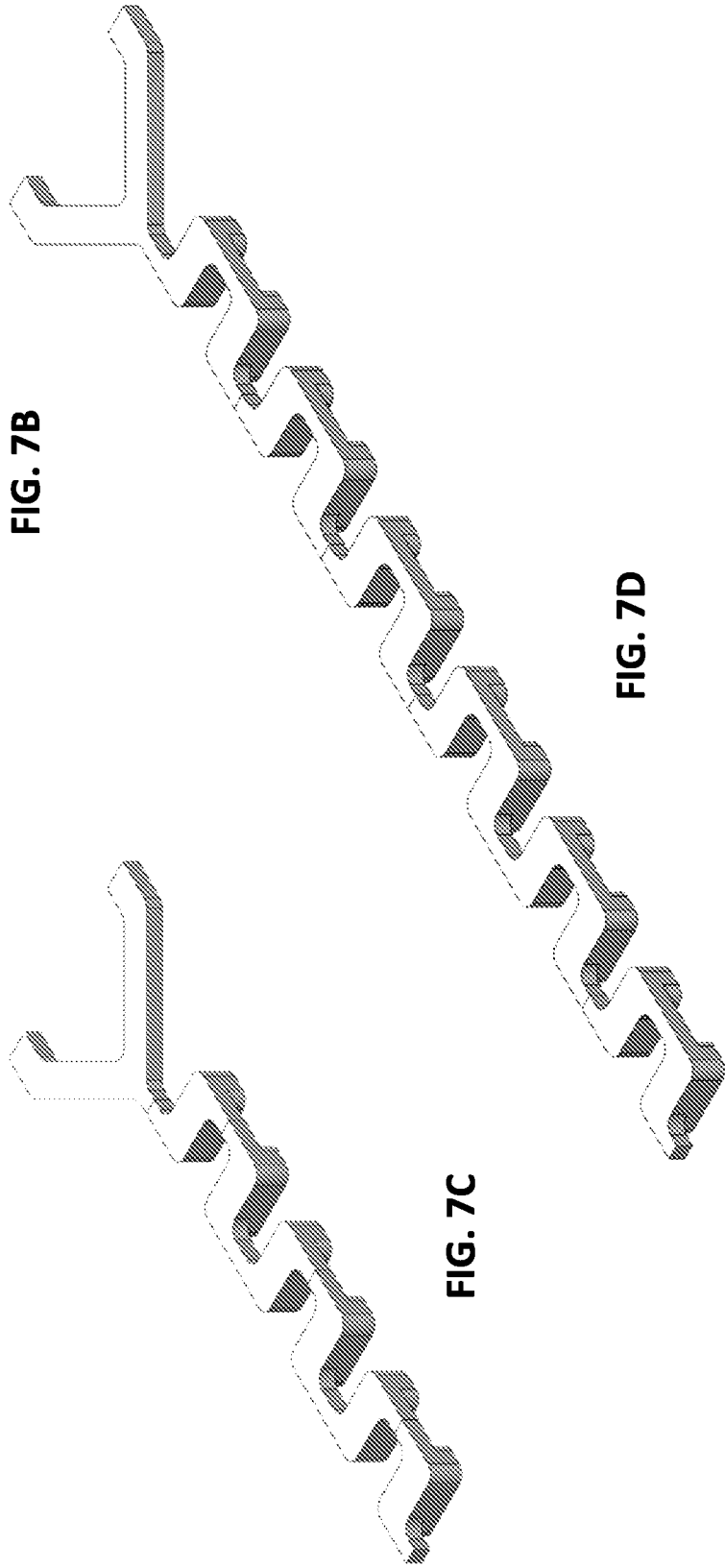

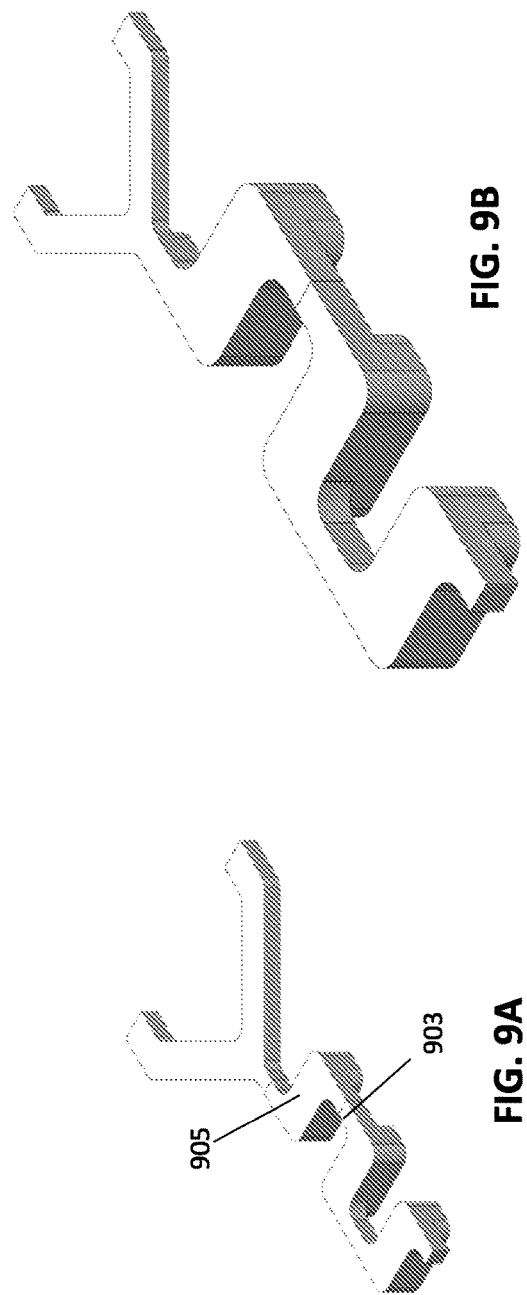
FIG. 9A
FIG. 9B
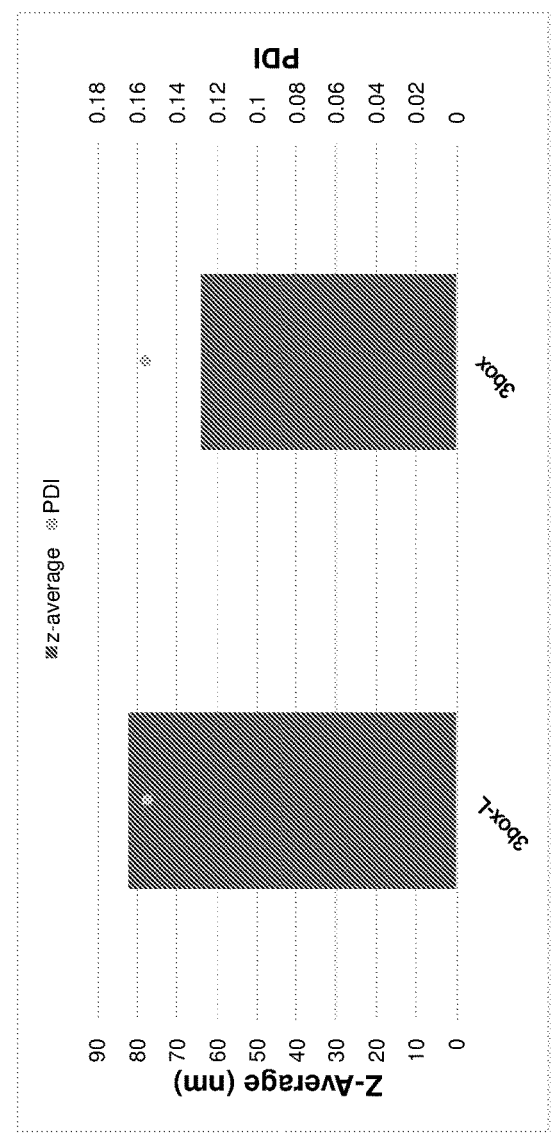
FIG. 9C

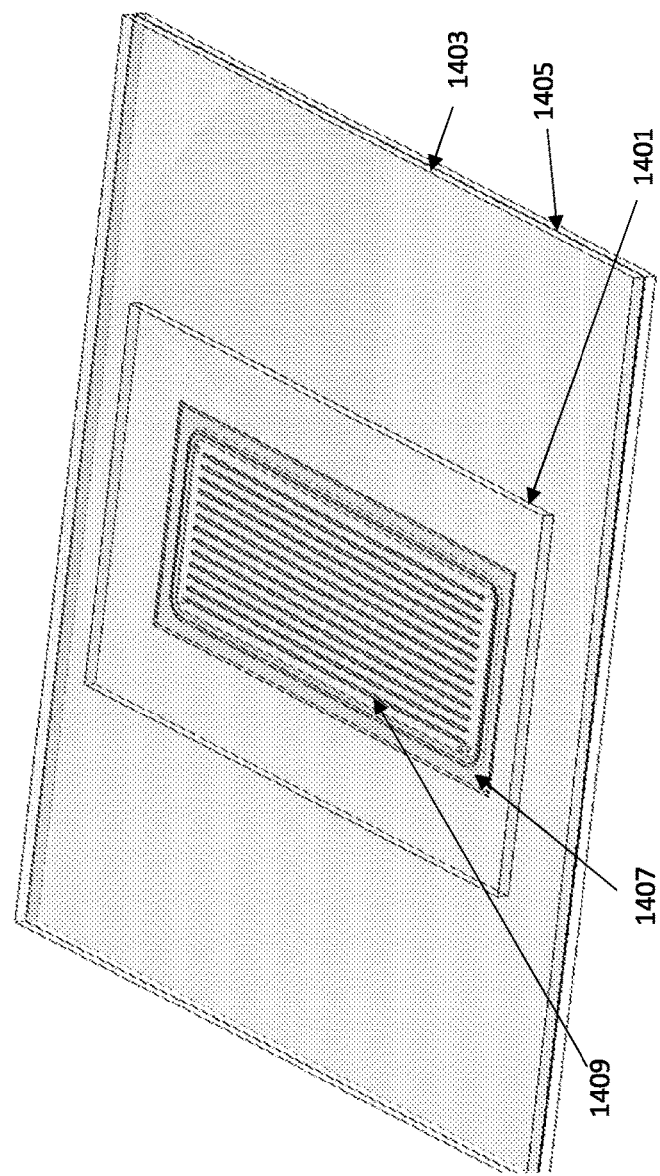
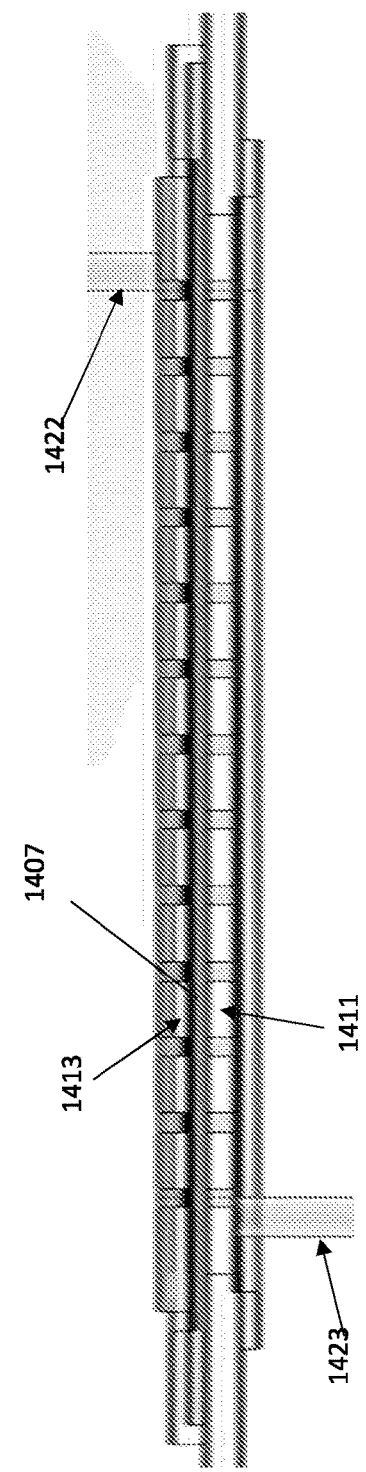
FIG. 14A
FIG. 14B

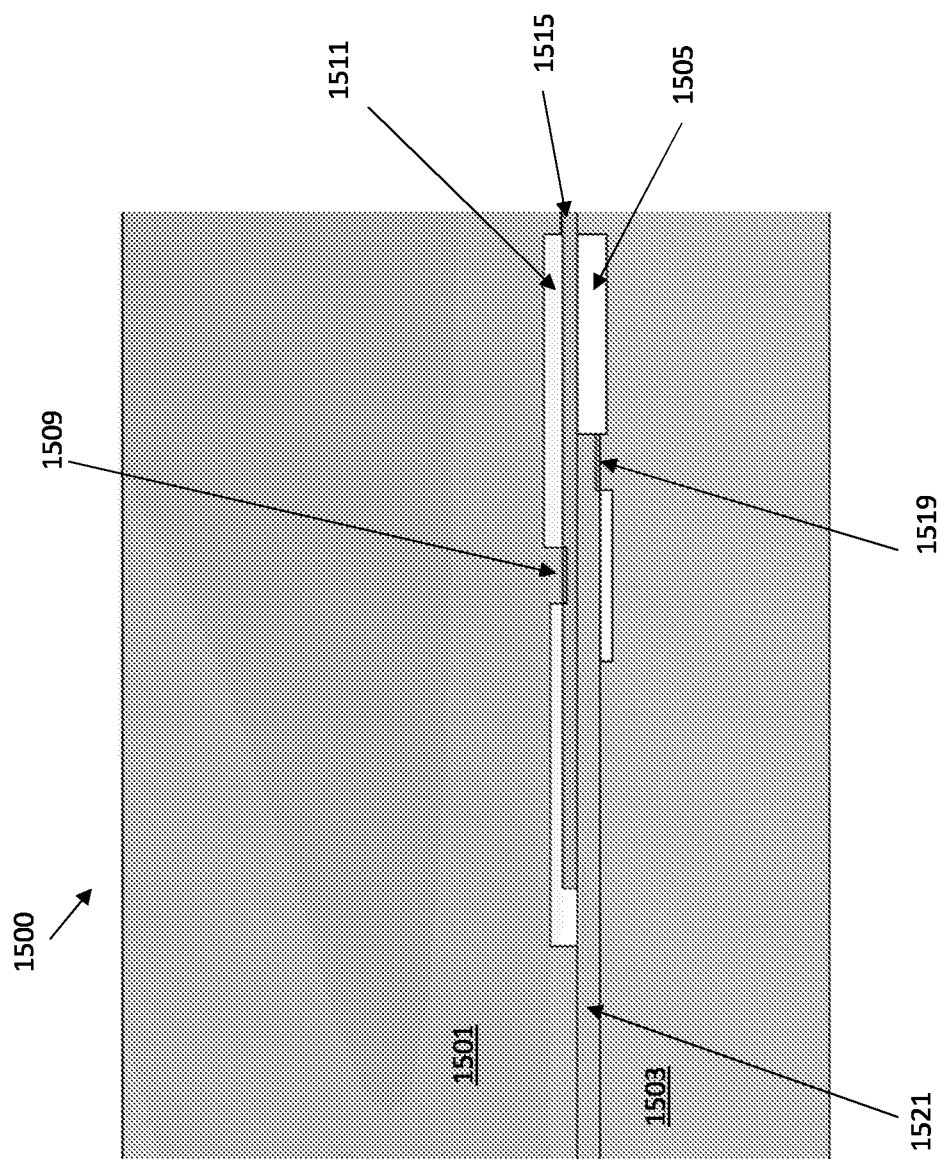

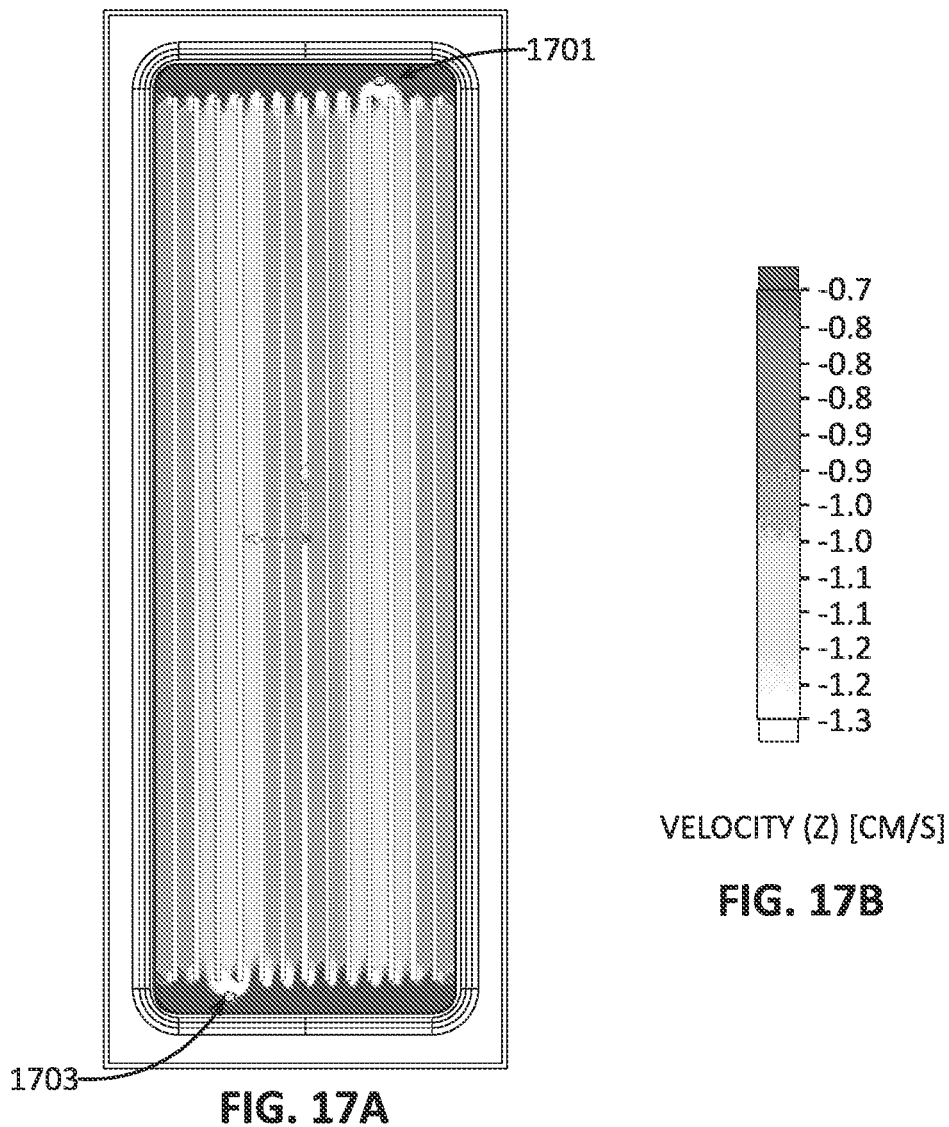
FIG. 17B
FIG. 17A
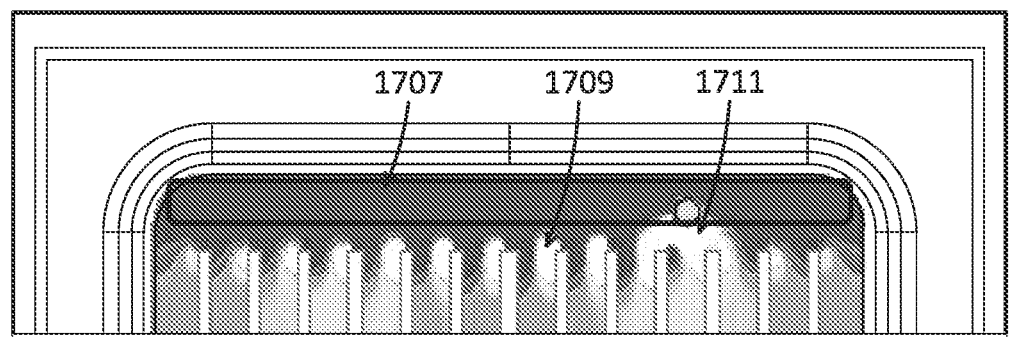
FIG. 17C

MIXING AND MICROFLUIDIC APPARATUSES RELATED THERETO

CROSS REFERENCE TO RELATED APPLICATIONS

This application is a continuation of U.S. patent application Ser. No. 17/727,937, titled "MIXING AND MICROFLUIDIC APPARATUSES RELATED THERETO," filed Apr. 25, 2022, issued as U.S. Pat. No. 11,724,257 on Aug. 15, 2023, which is a continuation of U.S. patent application Ser. No. 17/360,263, titled "MIXING AND MICROFLUIDIC APPARATUSES RELATED THERETO," filed Jun. 28, 2021, issued as U.S. Pat. No. 11,325,122 on May 10, 2022, which is a continuation of International patent application no. PCT/US2020/066541, filed Dec. 22, 2020, titled "MICROFLUIDIC APPARATUS AND METHODS OF USE THEREOF," which claims priority to U.S. provisional patent application No. 62/953,102, filed, Dec. 23, 2019, and titled "MICROFLUIDIC APPARATUS AND METHODS OF USE THEREOF," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Currently available technologies for manufacturing and formulating polynucleotide therapeutics, particularly mRNA therapeutics, often expose the products to contamination and degradation. Currently available centralized production can be too costly, too slow, and susceptible to contamination for use in therapeutic formulations possibly including multiple polynucleotide species. Development of scalable polynucleotide manufacturing, production of single patient dosages, elimination of touchpoints to limit contamination, input and process tracking for meeting clinical manufacturing requirements, and use in Point-of-Care operations can advance the use of these promising therapeutic modalities. Microfluidic instrumentation and processes can provide major advantages against these goals.

SUMMARY OF THE DISCLOSURE

The apparatuses and methods described herein may be used for the manufacture and formulation of biomolecule-containing products, particularly therapeutics for individualized care. In particular, described herein are closed path methods and apparatuses for processing therapeutic polynucleotides at a point of care.

In general, described herein are apparatuses and method for formulating composition using microfluidic devices. In particular, described herein are methods and apparatuses that include formulating compositions using a microfluidic mixing chamber (or a series of interconnected microfluidic mixing chambers) that are configured to provide highly efficient mixing in a relatively small footprint. These mixing chambers may operate within a particular flow rate to achieve a high degree of mixing. In some examples the mixing chambers may be cooled to a temperature that is below room temperature that enhancing mixing within the microfluidic mixing chambers described herein.

For example, the mixing chambers described herein may be referred to as box mixing chambers and/or vortex mixing chambers. These mixing chambers may be part of a microfluidic apparatus, e.g., microfluidic device, which may alternatively be referred to herein as a microfluidic path device. These chambers may generally include a base, having a base (e.g., bottom) surface, and side walls, and a cover (e.g., top) surface, enclosing the chamber. These mixing chambers may also include an inlet, e.g., mixing inlet, that receives input from two or more fluid paths within (or into) the microfluidic device. The inlet feeds into a chamber (e.g., in some examples, a box-shaped chamber) near a region of one side of the box chamber that is offset from the top and/or bottom, generally near the upper region of the first side of the chamber. The inlet is generally offset from the top and/or bottom of the chamber by a depth that is greater than about 1.5 times the depth of the inlet. The inlet may also be referred to as the fluidic intersection channel. For example, the mixing inlet channel may include an opening into the mixing chamber at a first side wall of the vortex mixing chamber. These chambers may also include a mixing outlet channel. The mixing outlet channel may include an opening into the mixing chamber in a second side wall of the vortex mixing chamber. In general, a vertical dimension of the vortex mixing chamber may be larger than a vertical dimension of the mixing inlet channel and may be larger than a vertical dimension of the mixing outlet channel.

The mixing channels described herein may receive two or more fluids from the inlet (e.g., a first fluid containing a first composition, such as an mRNA, and a second fluid containing a second composition, such as a delivery vehicle). The fluids (which may be combined prior to being driven into the mixing chamber), may extend into the mixing chamber and be directed slightly downward and against the wall opposite from the inlet. This may form a curving or curling fluid path in which the fluid is directed across, down and under the inlet, to mix and combine back with new material entering into the chamber from the inlet. The fluid may continue to mix, eventually driving the mixed fluid out of the outlet. In some examples the first mixing chamber is coupled to one or more mixing chambers in series so that the adjacent mixing chambers feed into each other in series. For example, the outlet of one chamber may be fed into the inlet in another chamber. As will be described below, any of these methods and apparatuses may include controlling the temperature of the mixing chamber to a temperature or range of temperatures (in some examples between about 10 and about 20 degrees C.) that is calibrated to enhance mixing for mixing in the mixing chambers described herein. The enhanced mixing temperature may be based on the formulation being mixed (in some examples the sequence of the mRNA and/or the delivery vehicle) within the particular geometry of the mixing chamber. This optimal temperature may be determined experimentally and/or by simulation. As used herein, "delivery vehicle" refers to any substance that facilitates, at least in part, the in vivo, in vitro, or ex vivo delivery of a polynucleotide to targeted cells or tissues (e.g., tumors, etc.). Referring to something as a delivery vehicle need not necessarily mean that it may not also have therapeutic effects. In one example, the delivery vehicle provides additional therapeutic effects. In another example, the delivery vehicle does not provide additional therapeutic effects. For example, a delivery vehicle may be an amino-lipidated peptoid delivery vehicle that may at least partially encapsulate an mRNA.

The apparatuses and methods described herein may be used with any appropriate microfluidic apparatus (e.g., microfluidic device, microfluidic system, etc.), particularly those in which a high degree of mixing is desired as part of an in-line, and in some examples, enclosed (e.g., closed-path) microfluidic path in which space may be a premium. Examples of microfluidic systems that may be used with any of the mixers and mixing techniques described herein may be found, for example, in Ser. No. 16/989,833, titled "METHODS AND APPARATUSES FOR MANUFACTURING FOR REMOVING MATERIAL FROM A THERAPEUTIC COMPOSITION," and filed on Aug. 10, 2020, which claims priority to U.S. provisional patent Application No. 62/885,159, entitled "MICROFLUIDIC APPARATUS AND METHODS OF USE THEREOF", filed on Aug. 9, 2019, and to U.S. provisional patent application No. 62/885,170, entitled "METHODS AND APPARATUSES FOR MANUFACTURING THERAPEUTIC COMPOSITIONS", filed on Aug. 9, 2019, each of which disclosures is herein incorporated by reference in its entirety.

Also described herein are microfluidic devices that include one or more mixers as described. For example, a microfluidic device may include: a first fluidic input and a second fluidic input; and a fluidic intersection channel configured to receive fluid from the first fluidic input and the second fluidic input, wherein the fluidic intersection channel opens into a first mixing chamber on an upper region of a first side of the first mixing chamber, wherein the first mixing chamber has a depth that is greater than about 1.5 times a depth of the fluidic intersection channel; an outlet channel on an upper region of a second side of the first mixing chamber, wherein the outlet channel has a depth that is less than the depth of the first mixing chamber, further wherein an opening of the outlet channel is offset along a width of the second side of the first mixing chamber relative to the fluidic intersection.

A microfluidic device may include: a first fluidic input channel and a second fluidic input channel, wherein the first and second fluidic input channels converge to form a fluidic intersection channel having a depth extending from a top surface to a first bottom surface and a width; a first mixing chamber having a depth extending from the top surface to a second bottom surface, a width extending from a first side to a second side, and a length, wherein the depth of the first mixing chamber is greater than the depth of the fluidic intersection channel and the width of the first mixing chamber is greater than the width of the fluidic intersection channel, further wherein the first mixing chamber is fluidly connected to the fluidic intersection channel at the top surface and proximate the first side; and an outlet channel, wherein the outlet channel is fluidly connected to the first mixing chamber at the top surface and proximate the second side of the mixing chamber.

A microfluidic device may include a first fluidic input and a second fluidic input; and a fluidic intersection channel configured to receive fluid from the first fluidic input and the second fluidic input, wherein the fluidic intersection channel opens into a first mixing chamber on an upper region of a first side of the first mixing chamber, wherein the first mixing chamber has a depth that is greater than about 1.5 times a depth of the fluidic intersection channel; a connection channel on an upper region of a second side of the first mixing chamber, wherein the connection channel has a depth that is less than the depth of the first mixing chamber, further wherein an opening of the connection channel is offset along a width of the second side of the first mixing chamber relative to the fluidic intersection, wherein the connection channel opens into a second mixing chamber; and an outlet channel extending from the second mixing chamber.

Any of these microfluidic devices may be configured as a single mixer in which the outlet channel forms a mixer output (e.g., without connecting in series to an additional mixing chamber). The outlet channel may connect to an output for the microfluidic device, or it may provide an input for further processing, including for combining with another fluid (and subsequent mixing), etc. When the mixing chamber is configured as a single mixer, the outlet channel does not act as the sole input to a second mixing chamber connected in series with the first mixing chamber.

Any of these microfluidic devices may have a depth of the first mixing chamber that is between about 2 times and about 4 times the fluidic intersection channel depth. The depth of the first mixing chamber may be approximately 3 times the fluidic intersection channel depth. In some examples the width of the first mixing chamber is between about 1.5 times and about 3 times the box length. For example, the width of the first mixing chamber may be approximately 2 times the box length.

The length of the first mixing chamber may be between about 2 times and about 4 times the fluidic intersection channel length. In some examples the length of the first mixing chamber is approximately 3 times the box length.

In general, the mixers described herein may be integrated into a microfluidics path device. For example, the fluidic intersection channel, first mixing chamber and outlet channel may all be formed within a first layer, further wherein the top surface of the fluidic intersection channel, first mixing chamber and outlet channel is formed of a second layer.

In general, the inlet and outlet into/out of the mixing chambers described herein may be separated from each other by an offset. For example, the outlet channel may fluidly communicate with the first mixing chamber at a first length of the mixing chamber and the fluidic intersection channel may fluidly communicate with the mixing chamber at a second length of the mixing chamber.

The mixing chamber may be a box having squared and/or rounded corners. For example, the first mixing chamber may have a corner radius of between about 65-85 µm at all or some of the corners. As used herein rounded refers to surfaces that transition smoothly, in a curve, rather than abruptly in an angle. A rounded corner may have a non-zero radius of curvature that is, e.g., 0.5 times and 0.01 times the length of the shortest sidewall to which it connects.

The microfluidic device of any of the examples described herein may be configured to provide a change in fluid pressure through the first mixing chamber at a flow rate of between about 0.25 ml/min and about 5 ml/min (e.g., between about 0.25 ml/min and about 4 ml/min, between about 0.25 ml/min and about 3 ml/min, between about 0.25 ml/min and about 2 ml/min, between about 0.25 ml/min and about 1.5 ml/min, etc.) and between about 1 psi (6.9 kPa) and about 30 psi (206.8 kPa), e.g., between about 1 psi and about 25 psi (about 6.9 kPa and about 172.4 kPa), between about 1 psi and about 22.5 psi (about 6.9 kPa and 155.1 kPa), between about 1 psi and about 20 psi (about 6.9 kPa and 137.9 kPa), between 1 and 10 psi (about 6.9 kPa and 68.9 kPa), between 1 and 5 psi (about 6.9 kPa and 34.5 kPa), etc.

A microfluidic device may include any number of mixing chambers that may be connected in series. Thus, a microfluidic apparatus may include a plurality of fluidly connected mixing chambers. For example a microfluidics path device may have a second mixing chamber having a depth extending from the top surface to a bottom surface of the second mixing chamber, a width extending from a first side to a second side of the second mixing chamber, and a length, wherein the depth of the second mixing chamber is greater than the depth of the outlet channel and the width of the second mixing chamber is greater than a width of the outlet channel, further wherein the second mixing chamber is fluidly connected to the outlet channel at the top surface and proximate the second side; and a second outlet channel having a depth and a width, wherein the second outlet channel is fluidly connected to the second mixing chamber at the top surface and proximate the first side of the second mixing chamber.

Any of these microfluidic devices may include one or more fluid pumps configured to pump fluid from the fluidic intersection channel into the first mixing chamber by deflecting at least a portion of an elastic membrane within the microfluidic device. For example, the microfluidic device may include one or more fluid pumps between the plurality of blending chambers and the microfluidic mixer, wherein the fluid pumps are configured to pump fluid from the fluidic intersection channel into the first mixing chamber by deflecting at least a portion of an elastic membrane within the microfluidic device. Alternatively or additionally, any of these apparatuses (e.g., any of these microfluidic devices) described herein may use a non-pulsatile pressure source to drive fluid from the fluidic intersection channel into one or more mixing chambers. Thus, the flow through the mixer may be continuous and non-pulsing.

For example, any of these microfluidic devices may include a plurality of pressure ports configured to deflect an elastic layer in the microfluidic device to drive fluid between through the first mixing chamber.

In some examples the microfluidic device includes a flow restrictor in fluid communication with the first fluidic input, wherein the flow restrictor comprises a serpentine elongate fluidic channel. In some examples the outlet channel is in fluid communication with one or more final blending chambers.

In general, a microfluidic mixer (e.g., a mixing apparatus, mixing system, mixing device, microfluidics vortex mixing apparatus, etc.) may include: a vortex mixing chamber comprising a base defining a bottom surface, side walls, and an upper surface enclosing the vortex mixing chamber; a mixing inlet channel comprising an opening into the vortex mixing chamber at a first side wall of the vortex mixing chamber, a mixing outlet channel comprising an opening into the vortex mixing chamber at a second side wall of the vortex mixing chamber, wherein a vertical dimension of the vortex mixing chamber is larger than a vertical dimension of the mixing inlet channel and is larger than a vertical dimension of the mixing outlet channel.

The first side wall and the second side wall may be on opposing side walls of the vortex mixing chamber. In some examples the mixing inlet channel and the mixing outlet channel connect to the vortex mixing chamber at offset locations along the first side wall and the second side wall. The height of the opening of the mixing inlet channel and the height of the opening of the mixing outlet channel may be the same. The width of the opening of the mixing inlet channel and the width of the opening of the mixing outlet channel may be the same.

The opening of the mixing inlet channel and the opening of the mixing outlet channel may be disposed at a height of the respective first side wall and second wall adjacent to the upper surface of the vortex mixing chamber.

The mixing inlet channel may have a first terminus comprising a fluidic intersection and a second terminus comprising the opening into the vortex mixing chamber. In some examples the fluidic intersection may further comprise a first fluidic input channel and a second fluidic input channel configured to intersect the mixing inlet channel at the fluidic intersection.

The first fluidic channel and the second fluidic channel may be configured to intersect at the fluidic intersection at an angle smaller than 180 degrees with respect to each other. The first fluidic channel and the second fluidic channel may be configured to intersect at the fluidic intersection at an angle greater than 30 degrees with respect to each other.

In some examples, the vortex mixing chamber, mixing inlet channel, and mixing outlet channel may be a first vortex mixing chamber, a first mixing inlet channel, and a second mixing outlet channel, and the microfluidic apparatus may further comprise a second microfluidic mixing apparatus comprising: a second vortex mixing chamber comprising a base defining a bottom surface, side walls, and an upper surface enclosing the second vortex mixing chamber; a second mixing inlet channel comprising an opening into the second vortex mixing chamber at a first side wall of the second vortex mixing chamber, a second mixing outlet channel comprising an opening into the second vortex mixing chamber at a second side wall of the second vortex mixing chamber, wherein a vertical dimension of the second vortex mixing chamber is larger than a vertical dimension of the second mixing inlet channel and is larger than a vertical dimension of the second mixing outlet channel.

As used herein a mixing apparatus may include a mixing system or a mixing device. A mixing apparatus may equivalently be referred to herein as a microfluidic mixer, or a microfluidic mixing device, or a microfluidic mixing system.

Any of the microfluidic apparatuses described herein may include one or more of: the first side wall and the second side wall of the second vortex chamber are opposing side walls of the second vortex mixing chamber; the second mixing inlet channel and the second mixing outlet channel connect to the second vortex mixing chamber at offset locations along the first side wall and the second side wall of the second vortex chamber; a height of the opening of the second mixing inlet channel and a height of the opening of the second mixing outlet channel are the same; a width of the opening of the second mixing inlet channel and a width of the opening of the second mixing outlet channel are the same; the opening of the second mixing inlet channel and the opening of the second mixing outlet channel are disposed at a height of the respective first side wall and second wall of the second vortex mixing chamber adjacent to the upper surface of the second vortex mixing chamber; and any combination thereof.

Any of the microfluidic apparatuses described herein may include a second mixing outlet channel that comprises a first terminus at the opening into the second vortex mixing chamber.

The microfluidic mixers described herein may be included as part of a microfluidic device (e.g., microfluidics chip) that is formed between two layers, and may include one or more pumps, blending chambers, etc. For example, a microfluidic apparatus may include: a first plate and a second plate; an elastic layer disposed between the first plate and the second plate; and a microfluidic path formed between the first plate and the second plate, wherein the microfluidic flow path comprises: a plurality of blending chambers each comprising a fixed volume configured to drive fluid between the blending chambers by deflecting at least a region of the elastic layer; a microfluidic mixer, wherein the microfluidic mixer comprises: a first fluidic input and a second fluidic input; and a fluidic intersection configured to receive fluid from the first fluidic input and the second fluidic input, wherein the fluidic intersection opens into a first mixing chamber on an upper region of a first side of the first mixing chamber, wherein the first mixing chamber has a depth that is greater than about 1.5 times a depth of the fluidic intersection; a connection channel on an upper region of a second side of the first mixing chamber, wherein the connection channel has a depth that is less than the depth of the first mixing chamber, further wherein an opening of the connection channel is offset along a width of the second side of the first mixing chamber relative to the fluidic intersection, wherein the connection channel opens into a second mixing chamber on an upper region of a first side of the second mixing chamber, further wherein the second mixing chamber has a depth that is greater than about 1.5 times a depth of the connection channel; and an output channel from the second mixing chamber on an upper region of a second side of the second mixing chamber wherein the second side of the second mixing chamber is opposite from the first side of the second mixing chamber.

An upper surface of the fluidic intersection may be configured to be level with an upper surface of the first mixing chamber. In some examples, an upper surface of the connection channel may be configured to be level with an upper surface of the first mixing chamber and an upper surface of the second mixing chamber. In some examples, the microfluidic apparatus may also include one or more fluid pumps configured to pump fluid from the blending chamber into the microfluidic mixer by deflecting at least a portion of the elastic layer.

Any of these microfluidic apparatuses may include one or more fluid pumps between the plurality of blending chambers and the microfluidic mixer, wherein the fluid pumps are configured to pump fluid from the blending chamber into the microfluidic mixer by deflecting at least a portion of the elastic layer. For example, a microfluidic apparatus may include a plurality of microfluidic mixers. In some examples the apparatus may include a plurality of pressure ports into the first plate configured to deflect the elastic layer to drive fluid between the blending chambers and through the microfluidic mixer.

In some examples the microfluidic apparatus includes a flow restrictor in fluid communication with the first fluidic input, wherein the flow restrictor comprises a serpentine elongate fluidic channel. The output channel may be in fluid communication with one or more blending chambers. The blending chamber may be a final blending chamber and/or may include a pair of blending chambers having a fixed volume, each blending chamber formed between the first plate and the second plate, wherein a portion of the elastic layer divides each chamber into a fluid-contacting side in the second plate and a pressure-receiving side in the first plate.

Any of the methods and apparatuses described herein including mixing using one or more of the mixing chambers described herein may include mixing at a lower temperature (e.g., a mixing temperature) that is generally between about 1 and about 30 degrees C. (e.g., about 2 and about 20 degrees C., e.g., between about 5 and about 18 degrees C., between about 5 degrees C. and about 15 degrees C., etc.). The enhanced mixing temperature for a particular composition (e.g., therapeutic mRNA and/or delivery vehicle) and/or for the geometry of the mixing chamber and/or for the flow rate (fluid pressure, etc.) of the fluids being mixed.

For example, a method of formulating a therapeutic mRNA with a delivery vehicle may include mixing the mRNA and delivery vehicle in a microfluidic mixing chamber at a temperature that is between about 2 and about 20 degrees C., wherein the temperature is selected based on the composition of the mRNA and/or the composition of the delivery vehicle. The temperature may be selected based on one or more of: a polynucleotide sequence of the therapeutic mRNA; a sequence of the delivery vehicle; a molecular weight of the delivery vehicle, a molecular weight of the therapeutic mRNA, a charge of the delivery vehicle, a charge of the mRNA, a molecular weight of the delivery vehicle; a molecular weight of the mRNA, a flow rate of the mRNA and/or the delivery vehicle within the microfluidic mixing chamber, and a dimension of the microfluidic mixing chamber.

In any of these methods and apparatuses, mixing may comprise mixing in a microfluidic device comprising the microfluidic mixing chamber. Any of these methods may include separately maintaining the temperature of the mixing chamber(s) relative to the rest of the microfluidic device. Mixing in the microfluidic mixing chamber may comprise passing the mRNA and delivery vehicle through a first opening into the mixing chamber of a microfluidic device so that the mRNA and delivery vehicle are driven against a wall of the mixing chamber and driven out of a plane of the first opening to a depth of greater than one times the depth of the first opening to form a mixed fluid comprising a therapeutic composition.

Passing may include driving the mRNA and delivery vehicle against the wall of the mixing chamber and out of a plane transverse to the first opening to the depth of greater than about 2.5 times the depth of the first opening. The mRNA and delivery vehicle may be driven against the wall of the mixing chamber and out of a plane transverse to the first opening to a depth of about 3 or more times the depth of the first opening. The top of the first opening may be in line with the top of the mixing chamber.

Also described are therapeutic compositions made using any of the method described herein. For example, described herein are therapeutic compositions of mRNA and delivery vehicles made by mixing the mRNA and delivery vehicle in a microfluidic mixing chamber at a temperature that is between about 2 and about 20 degrees C., wherein the temperature is selected based on the composition of the mRNA and/or the composition of the delivery vehicle.

A method of mixing within a microfluidic device as described herein may include: passing a first fluid and a second fluid through a first opening into a mixing chamber within a microfluidic device, so that the first and second fluids are driven against a wall of the mixing chamber and driven out of a plane of the first opening to a depth of greater than one times the depth of the first opening to form a mixed fluid; and passing the mixed fluid out of an outlet opening out of the mixing chamber; wherein the mixing chamber is maintained at a temperature of between about 2 and about 20 degrees C.

A method of mixing within a microfluidic device may include: passing a first fluid and a second fluid through at least one opening into a mixing chamber within a microfluidic device, so that the first and second fluids are driven against a wall of the mixing chamber and driven out of a plane of at least first opening; and passing the mixed fluid out of an outlet opening out of the mixing chamber; wherein the mixing chamber is maintained at a temperature of between about 2 and about 20 degrees C.

In some examples of the methods described herein the method is a method of mixing an oligonucleotide and delivery vehicle within a microfluidic device to form an aggregated nanoparticle and may include: passing a first fluid containing oligonucleotide molecules and a second fluid containing delivery vehicle chemistry through at least one opening into a mixing chamber within a microfluidic device, so that the first and second fluids are driven against a wall of the mixing chamber and driven out of a plane of an opening; and passing the mixed fluid out of an outlet opening out of the mixing chamber; wherein the mixing chamber is maintained at a temperature of between about 2 and about 20 degrees C.

A method of mixing within a microfluidic device may include: passing a first fluid and a second fluid through a first opening into a mixing chamber within a microfluidic device, so that the first and second fluids are driven against a wall of the mixing chamber and out of a plane transverse to the first opening to a depth of greater than about 2.5 times the depth of the first opening to form a uniformly mixed fluid; and passing the uniformly (or nearly uniformly) mixed fluid out of an outlet opening out of the mixing chamber, wherein the outlet opening is opposite from the first opening but is offset from the first opening; wherein the mixing chamber is maintained at a temperature of between about 5 and about 20 degrees C. to uniformly mix the first and second fluid.

Passing the first fluid and the second fluid through the first opening into the mixing chamber may include passing the first and second fluids so that the first and second fluids are driven against the wall of the mixing chamber and out of the plane transverse to the first opening to the depth of greater than about 2.5 times the depth of the first opening.

As mentioned above, in some examples the mixing chamber may be maintained at a temperature of between about 5 and about 15 degrees C. to uniformly mix the first and second fluids; in some examples the temperature of the mixture is maintained at between about 5 and about 15 degrees C. (e.g., at approximately 10 degrees C.). Any of these methods may include passing the mixed fluid from the outlet opening into a second opening into a second mixing chamber, so that the fluid is driven against a wall of the second mixing chamber and driven out of a plane of the second opening to a depth of greater than one times the depth of the second opening to further mix the mixed fluid. For example, the fluid may be driven against the wall of the mixing chamber and out of the plane transverse to the first opening to a depth of about 3 or more times the depth of the first opening. As mentioned, the top of the first opening may be in line with the top of the first mixing chamber. In some examples the outlet opening has a cross-section area that is equivalent to a cross-sectional area of the first opening. The mixing chamber may be formed between a first layer and a second layer of the microfluidics path device. The mixing chamber may have a length that is greater than the width, further wherein the length is greater than about 2 times the width of the first opening.

Also described herein are therapeutic compositions comprising an mRNA and a delivery vehicle (DV), made as described herein, e.g., by passing a first fluid comprising the mRNA and a second fluid comprising the DV through a first opening into a mixing chamber within a microfluidic device, so that the first and second fluids are driven against a wall of the mixing chamber and driven out of a plane of the first opening to a depth of greater than one times the depth of the first opening to form a mixed fluid; and passing the mixed fluid out of an outlet opening out of the mixing chamber; wherein the mixing chamber is maintained at a temperature of between about 2 and about 20 degrees C.

Also described are methods of treatment using any of the compositions formed as described herein. In some cases, these compositions may only be fabricated to the desired concentrations and volumes (and purity) when using the described methods. For example, a method of treating a disease may include: synthesizing one or more therapeutic mRNAs in a microfluidic device, wherein the one or more therapeutic mRNAs are within a first fluid and a delivery vehicle for the one or more therapeutic mRNAs is within a second fluid; passing the first fluid and the second fluid through a first opening into a mixing chamber within the microfluidic device, so that the first and second fluids are driven against a wall of the mixing chamber and driven out of a plane of the first opening to a depth of greater than one times the depth of the first opening to form a mixed fluid comprising a therapeutic composition; passing the mixed fluid out of an outlet opening out of the mixing chamber, wherein the mixing chamber is maintained at a temperature of between about 2 and about 20 degrees C.; and administering the therapeutic composition to a patient.

The mixing temperature, which may generally (but not necessarily) be between about 2 and about 20 degrees C., may be selected (as the enhanced mixing temperature) based on the dimensions of the mixer (e.g., the box mixer), the composition of the mRNA (e.g., the therapeutic mRNA) and/or the composition of the delivery vehicle (DV). Thus any of the methods described herein may include calibrating or selecting the temperature of the mixing chamber to set the enhanced mixing temperature; the temperature of the mixing chamber(s) may be controlled separately from the temperature(s) of other portions of the microfluidic device that includes the mixer. In some examples the mixing temperature may be calibrated or selected (to the enhanced mixing temperature) by modeling the mixing in vitro or in vivo. For example, an optimal mixing temperature may be estimated and/or set based on the mRNA composition (e.g., as a function of one or more of the percentages or ratios of the nucleotides making the mRNA(s), the length(s) of the mRNA(s), the concentration of the mRNA(s), etc.). Additionally or alternatively, an optimal mixing temperature may be estimated based on the composition of the delivery vehicle, such as but not limited to the molecular weight, the concentration, the charge, etc. For example, in some examples selecting and/or setting the enhanced mixing temperature includes selecting a temperature between about 2 and about 20 degrees C. based on the delivery vehicle and the one or more therapeutic mRNAs. In some examples the optimal temperature may be greater than about 2-20 degrees (greater than about 2 degrees, greater than about 5 degrees, greater than about 10 degrees, greater than about 12.5 degrees, greater than about 15 degrees, greater than about 17.5 degrees, greater than about 20 degrees, etc.). For example, in some examples the optimal temperature range may be between about 2 and about 50 degrees C. In some examples the optimal mixing temperate may be calculated or estimated in part on the geometry of the mixing chamber(s) and/or the fluid pressure and/or flow rate of the material being mixed in the mixing chamber(s). The optimal mixing temperature may refer to the temperature that the mixing chamber may be held at during mixing in order to result in more uniform mixing following passage through the mixing chamber(s).

Passing the first fluid and the second fluid through the first opening into the mixing chamber may include passing the first and second fluids so that the first and second fluids are driven against the wall of the mixing chamber and out of a plane transverse to the first opening to the depth of greater than about 2.5 times the depth of the first opening. The fluid may be driven against the wall of the mixing chamber and out of a plane transverse to the first opening to a depth of about 3 or more times the depth of the first opening. In some examples, the top of the first opening is in line with the top of the mixing chamber. The outlet opening may have a cross-section area that is equivalent to a cross-sectional area of the first opening. The mixing chamber may be formed between a first layer and a second layer of the microfluidics path device. In some examples, the mixing chamber has a length that is greater than the width, for example, the length may be greater than about 2 times the width of the first opening.

A method of forming a therapeutic composition to treat a disease may include: passing one or more therapeutic mRNAs that are within a first fluid and a delivery vehicle for the one or more therapeutic mRNAs within a second fluid the second fluid through a first opening into a mixing chamber within the microfluidic device, so that the first and second fluids are driven against a wall of the mixing chamber and driven out of a plane of the first opening to a depth of greater than one times the depth of the first opening to form a mixed fluid comprising the therapeutic composition; maintaining the temperature of the mixing chamber at a temperature determined by the one or more therapeutic and/or the delivery vehicle, wherein the temperature is between about 2 and about 20 degrees C., while forming the mixed fluid; and passing the mixed fluid out of an outlet opening out of the mixing chamber.

As mentioned above, any of these methods may include determining the optimum mixing temperature. For example, maintaining the temperature of the mixing chamber may further include selecting and/or setting the temperature of the mixing chamber to be the enhanced mixing temperature. The enhanced mixing temperature may be determined by may include modeling the mixing in vitro and/or experimentally determining an enhanced mixing temperature in vivo. In any of these examples, selecting and/or setting of the enhanced mixing temperature may include determining the temperature or range of temperatures at which a yield of mRNA (e.g., mRNA expression) in vivo or in vitro is maximized for various temperatures in order to enhance (e.g., increase) the production of active compounds. Thus, the enhanced mixing temperature may include the temperature or range of temperatures at which mixing occurs for mRNA expression in the system(s) described herein. Determining and/or setting the enhanced mixing temperature may include selecting a temperature between about 2 and about 20 degrees C. based on the delivery vehicle and the one or more therapeutic mRNAs.

For example, described herein are microfluidic devices comprising: a first fluidic input and a second fluidic input; and a fluidic intersection channel to receive fluid from the first fluidic input and the second fluidic input, wherein the fluidic intersection channel opens into a first mixing chamber on an upper region of a first side of the first mixing chamber, wherein the first mixing chamber has a length, a width, and a depth, wherein the depth is greater than about 1.5 times a depth of the fluidic intersection channel; an outlet channel on an upper region of a second side of the first mixing chamber, wherein the outlet channel has a depth that is less than the depth of the first mixing chamber, and wherein an opening of the outlet channel is offset along a width of the second side of the first mixing chamber relative to the fluidic intersection.

A microfluidic device may include: a first fluidic input channel and a second fluidic input channel, wherein the first and second fluidic input channels converge to a fluidic intersection channel having width and a depth extending from a top surface to a first bottom surface; a first mixing chamber having a depth extending from the top surface to a second bottom surface, a width extending from a first side to a second side, and a length, wherein the depth of the first mixing chamber is greater than the depth of the fluidic intersection channel and the width of the first mixing chamber is greater than the width of the fluidic intersection channel, and wherein the first mixing chamber is fluidly connected to the fluidic intersection channel at the top surface and proximate the first side; and an outlet channel, wherein the outlet channel is fluidly connected to the first mixing chamber at the top surface and proximate the second side of the first mixing chamber.

A microfluidic device may include: a first fluidic input and a second fluidic input; and a fluidic intersection channel to receive fluid from the first fluidic input and the second fluidic input, wherein the fluidic intersection channel opens into a first mixing chamber on an upper region of a first side of the first mixing chamber, wherein the first mixing chamber has a width, a length and a depth, wherein the depth is greater than about 1.5 times a depth of the fluidic intersection channel; a connection channel on an upper region of a second side of the first mixing chamber, wherein the connection channel has a depth that is less than the depth of the first mixing chamber, further wherein an opening of the connection channel is offset along the width of the second side of the first mixing chamber relative to the fluidic intersection, wherein the connection channel opens into a second mixing chamber; and an outlet channel extending from the second mixing chamber.

In any of these microfluidic devices the depth of the first mixing chamber may be between about 2 times and about 4 times the fluidic intersection channel depth. The depth of the first mixing chamber may be about 3 times the fluidic intersection channel depth. The width of the first mixing chamber may be between about 1.5 times and about 3 times the box length. The width of the first mixing chamber may be about 2 times the box length. The length of the first mixing chamber may be between about 2 times and about 4 times the fluidic intersection channel length. The length of the first mixing chamber may be about 3 times the box length.

The fluidic intersection channel, first mixing chamber and outlet channel may all be within a first layer, and wherein the top surface of the fluidic intersection channel, first mixing chamber and outlet channel comprises a second layer. The outlet channel may fluidly communicate with the first mixing chamber at a first length of the mixing chamber and the fluidic intersection channel fluidly communicates with the mixing chamber at a second length of the mixing chamber.

The first mixing chamber may have rounded corners. The first mixing chamber may have a corner radius of between about 65 and about 85 μm. The change in fluid pressure through the first mixing chamber at a flow rate of between 0.25 and 5 ml/min may be between about 6.9 kPa and about 206.8 kPa. The width of the first mixing chamber may be between about 150 and about 600 μm, the depth of the first mixing chamber may be between about 150 and about 500 μm, and the length of the first mixing chamber may be between about 500 μm and about 1000 μm.

The connecting channel may have a width that is between about 75 μm and about 225 μm, a depth that is between about 75 μm and about 225 μm, and a length that is between about 225 and about 550 μm.

Any of these microfluidic devices may include: a second mixing chamber having a depth extending from the top surface to a bottom surface of the second mixing chamber, a width extending from a first side to a second side of the second mixing chamber, and a length, wherein the depth of the second mixing chamber is greater than the depth of the outlet channel and the width of the second mixing chamber is greater than a width of the outlet channel, further wherein the second mixing chamber is fluidly connected to the outlet channel at the top surface and proximate the second side; and a second outlet channel having a depth and a width, wherein the second outlet channel is fluidly connected to the second mixing chamber at the top surface and proximate the first side of the second mixing chamber.

Any of the microfluidic devices described herein may have one or more fluid pumps to pump fluid from the fluidic intersection channel into the first mixing chamber by deflecting at least a portion of an elastic membrane within the microfluidic device. Any of the microfluidic device described herein may have one or more fluid pumps between the plurality of blending chambers and the microfluidic mixer, wherein the fluid pumps are to pump fluid from the fluidic intersection channel into the first mixing chamber by deflecting at least a portion of an elastic membrane within the microfluidic device.

A microfluidic device may include a plurality of fluidly connected mixing chambers including the first mixing chamber.

Any of the microfluidic devices described herein may include a plurality of pressure ports configured to deflect an elastic layer in the microfluidic device to drive fluid between through the first mixing chamber. Any of the microfluidic devices described herein may include a flow restrictor in fluid communication with the first fluidic input, wherein the flow restrictor comprises a serpentine elongate fluidic channel.

A microfluidic mixing apparatus may include: a mixing chamber (e.g., comprising a base defining a bottom surface, side walls, and an upper surface enclosing the mixing chamber); a mixing inlet channel (e.g., comprising an opening into the mixing chamber at a first side wall of the mixing chamber); a mixing outlet channel (e.g., comprising an opening into the mixing chamber at a second side wall of the mixing chamber), or any combination of these. A vertical dimension of the mixing chamber may be larger than a vertical dimension of the mixing inlet channel and may be larger than a vertical dimension of the mixing outlet channel.

The first side wall and the second side wall may be opposing side walls of the mixing chamber. The mixing inlet channel and the mixing outlet channel may connect to the mixing chamber at offset locations along the first side wall and the second side wall. The height of the opening of the mixing inlet channel and the height of the opening of the mixing outlet channel may be the same. The width of the opening of the mixing inlet channel and the width of the opening of the mixing outlet channel may be the same.

The opening of the mixing inlet channel and the opening of the mixing outlet channel may be disposed at a height of the respective first side wall and second wall adjacent to the upper surface of the mixing chamber. The mixing inlet channel may have a first terminus comprising a fluidic intersection and a second terminus comprising the opening into the mixing chamber.

The fluidic intersection may further comprise a first fluidic input channel and a second fluidic input channel that intersect the mixing inlet channel at the fluidic intersection. The first fluidic channel and the second fluidic channel may intersect at the fluidic intersection at an angle smaller than about 180 degrees with respect to each other. The first fluidic channel and the second fluidic channel may intersect at the fluidic intersection at an angle greater than about 30 degrees with respect to each other.

The mixing chamber may be a first mixing chamber, the mixing inlet channel may be a first mixing inlet channel, and/or the mixing outlet channel may be a first mixing outlet channel. The microfluidic apparatus may further comprise a second microfluidic mixing apparatus comprising: a second mixing chamber comprising a base defining a bottom surface, side walls, and an upper surface enclosing the second mixing chamber; a second mixing inlet channel comprising an opening into the second mixing chamber at a first side wall of the second mixing chamber, a second mixing outlet channel comprising an opening into the second mixing chamber at a second side wall of the second mixing chamber, wherein a vertical dimension of the second mixing chamber is larger than a vertical dimension of the second mixing inlet channel and is larger than a vertical dimension of the second mixing outlet channel.

The first side wall and the second side wall of the second chamber may be opposing side walls of the second mixing chamber; the second mixing inlet channel and the second mixing outlet channel may connect to the second mixing chamber at offset locations along the first side wall and the second side wall of the second chamber; a height of the opening of the second mixing inlet channel and a height of the opening of the second mixing outlet channel may be the same; and a width of the opening of the second mixing inlet channel and a width of the opening of the second mixing outlet channel may be the same.

A microfluidic apparatus as described above may include a second mixing outlet channel that comprises a first terminus at the opening into the second mixing chamber.

Also described herein are microfluidic apparatuses comprising cascading microfluidic mixing apparatuses, wherein each of the cascading microfluidic mixing apparatuses may include: a mixing chamber (e.g., comprising a base defining a bottom surface, side walls, and an upper surface); a mixing inlet channel (e.g., comprising an opening into the mixing chamber at a first side wall of the mixing chamber); a mixing outlet channel (e.g., comprising an opening into the mixing chamber at a second side wall of the mixing chamber), or any combination of these. A vertical dimension of the mixing chamber may be larger than a vertical dimension of the mixing inlet channel and may be larger than a vertical dimension of the mixing outlet channel. Further, cascading microfluidic mixers may be connected to one another in a series so that the mixing inlet channel of each of the cascading microfluidic mixers after a first microfluidic mixer in the series may be connected to the mixing outlet of a prior microfluidic mixer in the series.

A microfluidic apparatus may comprise: a first plate and a second plate; an elastic layer disposed between the first plate and the second plate; and a microfluidic path between the first plate and the second plate, wherein the microfluidic path comprises: a plurality of blending chambers each comprising a fixed volume separated by a portion of the elastic layer, wherein the portion of the elastic layer is configured to deflect to drive fluid between blending chambers of the plurality of blending chambers; a first microfluidic mixer, wherein the first microfluidic mixer comprises: a first fluidic input and a second fluidic input; a fluidic intersection to receive fluid from the first fluidic input and the second fluidic input, wherein the fluidic intersection opens into a first mixing chamber on an upper region of a first side of the first mixing chamber, wherein the first mixing chamber has a depth that is greater than 1.5 times a depth of the fluidic intersection; a connection channel on an upper region of a second side of the first mixing chamber, wherein the connection channel has a depth that is less than the depth of the first mixing chamber, further wherein an opening of the connection channel is offset along a width of the second side of the first mixing chamber relative to the fluidic intersection, wherein the connection channel opens into a second mixing chamber on an upper region of a first side of the second mixing chamber, further wherein the second mixing chamber has a depth that is greater than 1.5 times a depth of the connection channel; and an output channel from the second mixing chamber on an upper region of a second side of the second mixing chamber wherein the second side of the second mixing chamber is opposite from the first side of the second mixing chamber.

An upper surface of the fluidic intersection may be substantially level with an upper surface of the first mixing chamber. An upper surface of the connection channel may be configured to be level with an upper surface of the first mixing chamber and an upper surface of the second mixing chamber.

Any of the microfluidic apparatuses described herein may include one or more fluid pumps to pump fluid from the blending chamber into the first microfluidic mixer by deflecting at least a portion of the elastic layer. The microfluidic apparatuses described herein may include one or more fluid pumps between the plurality of blending chambers and the first microfluidic mixer, wherein the fluid pumps are to pump fluid from the blending chamber into the first microfluidic mixer by deflecting at least a portion of the elastic layer.

The microfluidic apparatus may comprise a plurality of microfluidic mixers including the first microfluidic mixer, and/or a plurality of pressure ports into the first plate configured to deflect the elastic layer to drive fluid between the blending chambers and through the first microfluidic mixer. Any of the microfluidic apparatuses described herein may include a flow restrictor in fluid communication with the first fluidic input, wherein the flow restrictor comprises a serpentine elongate fluidic channel.

The final blending chamber may comprise a pair of blending chambers having a fixed volume, each blending chamber is disposed between the first plate and the second plate, and wherein a portion of the elastic layer divides each chamber into a fluid-contacting side in the second plate and a pressure-receiving side in the first plate.

Also described herein are methods of formulating a therapeutic mRNA with a delivery vehicle, the method comprising mixing the mRNA and the delivery vehicle in a microfluidic mixing chamber at a temperature that is between about 2 and about 20 degrees C., wherein the temperature is selected using at least the composition of the mRNA, the composition of the delivery vehicle, or a combination thereof.

Any of these methods may include selecting the temperature using at least: a polynucleotide sequence of the therapeutic mRNA; a sequence of the delivery vehicle; a molecular weight of the delivery vehicle, a molecular weight of the therapeutic mRNA, a charge of the delivery vehicle, a charge of the mRNA, a molecular weight of the delivery vehicle; a molecular weight of the mRNA, a flow rate of the mRNA and/or the delivery vehicle within the microfluidic mixing chamber, and a dimension of the microfluidic mixing chamber, or any combination thereof.

Mixing may include mixing in a microfluidic device comprising the microfluidic mixing chamber.

Any of these methods may include separately maintaining the temperature of the mixing chamber to be between about 2 and about 20 degrees C., relative to the rest of the microfluidic device. Mixing in the microfluidic mixing chamber may include passing the mRNA and the delivery vehicle through a first opening into the mixing chamber of a microfluidic device so that the mRNA and the delivery vehicle are driven against a wall of the mixing chamber and driven out of a plane of the first opening to a depth of greater than one times the depth of the first opening. The methods described herein may include passing that comprises driving the mRNA and the delivery vehicle against the wall of the mixing chamber and out of a plane transverse to the first opening to the depth of greater than about 2.5 times the depth of the first opening.

The mRNA and the delivery vehicle may be driven against the wall of the mixing chamber and out of a plane transverse to the first opening to a depth of 3 or more times the depth of the first opening. A top of the first opening may be in line with a top of the mixing chamber.

Also described herein are methods of mixing including: passing a first fluid and a second fluid through a first opening into a mixing chamber in a microfluidic device, so that the first and second fluids are driven against a wall of the mixing chamber and driven out of a plane of the first opening to a depth of greater than one times the depth of the first opening to form a mixed fluid; and passing the mixed fluid out of an outlet opening out of the mixing chamber; wherein the mixing chamber is maintained at a temperature of between about 2 and about 20 degrees C.

A method of mixing may include: passing a first fluid and a second fluid through at least one opening into a mixing chamber within a microfluidic device, so that the first and second fluids are driven against a wall of the mixing chamber and driven out of a plane of at least first opening; and passing the mixed fluid out of an outlet opening out of the mixing chamber; wherein the mixing chamber is maintained at a temperature of between 2 and 20 degrees C.

Also described herein are methods of mixing, the method comprising: passing a first fluid containing oligonucleotide molecules and a second fluid containing delivery vehicle chemistry through at least one opening into a mixing chamber in a microfluidic device, so that the first and second fluids are driven against a wall of the mixing chamber and driven out of a plane of an opening; and passing the mixed fluid out of an outlet opening out of the mixing chamber; wherein the mixing chamber is maintained at a temperature of between about 2 and about 20 degrees C.

A method of mixing within a microfluidic device may include: passing a first fluid and a second fluid through a first opening into a mixing chamber within a microfluidic device, so that the first and second fluids are driven against a wall of the mixing chamber and out of a plane transverse to the first opening to a depth of greater than about 2.5 times the depth of the first opening to form a substantially mixed fluid; and passing the mixed fluid out of an outlet opening out of the mixing chamber, wherein the outlet opening is opposite from the first opening but is offset from the first opening; wherein the mixing chamber is maintained at a temperature of between about 5 and about 20 degrees C.

Passing the first fluid and the second fluid through the first opening into the mixing chamber may comprise passing the first and second fluids so that the first and second fluids are driven against the wall of the mixing chamber and out of the plane transverse to the first opening to the depth of greater than about 2.5 times the depth of the first opening.

Any of the methods described herein may include maintaining the temperature of the mixing chamber between about 5 and about 15 degrees C. The methods described herein may include maintain the temperature of the mixed fluid at between about 5 and about 15 degrees C. The method described herein may include maintaining a temperature of the mixed fluid at about degrees C. The methods described herein may include passing the mixed fluid from the outlet opening into a second opening into a second mixing chamber, so that the fluid is driven against a wall of the second mixing chamber and driven out of a plane of the second opening to a depth of greater than one times the depth of the second opening to further mix the mixed fluid. The fluid may be driven against the wall of the mixing chamber and out of the plane transverse to the first opening to a depth of about 3 or more times the depth of the first opening.

In any of these methods, a top of the first opening may be in line with a top of the first mixing chamber. The outlet opening may have a cross-section area that is equal to a cross-sectional area of the first opening. The mixing chamber may be between a first layer and a second layer of the microfluidic device. The mixing chamber may have a length that is greater than the width, and the length may be greater than about 2 times the width of the first opening.

Also described herein are methods of forming a composition comprising: synthesizing one or more therapeutic mRNAs in a microfluidic device, wherein the one or more therapeutic mRNAs are within a first fluid and a delivery vehicle for the one or more therapeutic mRNAs is within a second fluid; passing the first fluid and the second fluid through a first opening into a mixing chamber in the microfluidic device, so that the first and second fluids are driven against a wall of the mixing chamber and driven out of a plane of the first opening to a depth of greater than one times the depth of the first opening to form a mixed fluid, wherein the mixing chamber is maintained at a temperature that is selected to enhance mixing of the therapeutic mRNA and delivery vehicle; and passing the mixed fluid out of an outlet opening out of the mixing chamber. The temperature may be selected to enhance (e.g., increase) mixing as compared to mixing with all other parameters (except the temperature) are kept substantially constant; as described herein, this may result in mixing at lower temperatures to the same level or better (e.g., temperatures between 2 degrees C. and 20 degrees C.).

For example, the mixing chamber may be maintained at the temperature that is selected to enhance mixing of for the therapeutic mRNA and delivery vehicle and is between 2 and 20 degrees C.

Any of these methods may include selecting an enhanced mixing temperature of the mixing chamber. Selecting the enhanced mixing temperature may include modeling the mixing in vitro or in vivo. Selecting the enhanced mixing temperature may include selecting a temperature between about 2 and about 20 degrees C. based on the delivery vehicle and the one or more therapeutic mRNAs. The passing the first fluid and the second fluid through the first opening into the mixing chamber may include passing the first and second fluids so that the first and second fluids are driven against the wall of the mixing chamber and out of a plane transverse to the first opening to the depth of greater than about 2.5 times the depth of the first opening. The fluid may be driven against the wall of the mixing chamber and out of a plane transverse to the first opening to a depth of about 3 or more times the depth of the first opening. The top of the first opening may be in line with a top of the mixing chamber. The outlet opening may have a cross-section area that is equal to a cross-sectional area of the first opening. The mixing chamber may be between a first layer and a second layer of the microfluidic device. The mixing chamber may have a length that is greater than a width, further the length may be greater than 2 times the width of the first opening.

Also described herein are methods of forming a therapeutic composition, the method comprising: passing one or more therapeutic mRNAs within a first fluid and a delivery vehicle for the one or more therapeutic mRNAs within a second fluid through a first opening into a mixing chamber in a microfluidic device, so that the first and second fluids are driven against a wall of the mixing chamber and driven out of a plane of the first opening to a depth of greater than one times the depth of the first opening to form a mixed fluid comprising the therapeutic composition; maintaining a temperature of the mixing chamber at an enhanced mixing temperature determined to enhance mixing; and passing the mixed fluid out of an outlet opening out of the mixing chamber.

The enhanced mixing temperature may be between about 2 and about 20 degrees C. Maintaining may include determining the enhanced mixing temperature for the one or more therapeutic mRNAs and/or the delivery vehicle.

Any of the methods described herein may include determining the enhanced mixing temperature by modeling the mixing in vitro or in vivo. Any of these methods may include determining the enhanced mixing temperature by selecting a temperature between about 2 and about 20 degrees C. having greater mixing as compared to mixing at other temperatures between about 2 and about 20 degrees C. Thus, the enhanced mixing temperature may be a temperature within the range of about 2-20 degrees C. in which the mixing is at or near a maximum as compared to other temperatures within this temperature range. The enhanced mixing temperature may not be the peak (maximum) value, but may be within range of the temperature corresponding to the peak mixing value (e.g., within 2 degrees, within 1.5 degrees, within 1 degree, within 0.5 degrees, within 0.2 degrees, within 0.2 degrees, etc.).

The passing the first fluid and the second fluid through the first opening into the mixing chamber may comprise passing the first and second fluids so that the first and second fluids are driven against the wall of the mixing chamber and out of a plane transverse to the first opening to the depth of greater than about 2.5 times the depth of the first opening. The fluid may be driven against the wall of the mixing chamber and out of a plane transverse to the first opening to a depth of about 3 or more times the depth of the first opening. A top of the first opening may be in line with a top of the mixing chamber. The outlet opening may have a cross-section area that is equivalent to a cross-sectional area of the first opening. The mixing chamber may be formed between a first layer and a second layer of the microfluidic device. The mixing chamber may have a length that is greater than the width, and the length may be greater than 2 times the width of the first opening.

Also described herein are methods of mixing that include: passing a first fluid and a second fluid through a first opening into a mixing chamber in a microfluidic device, so that the first and second fluids are driven against a wall of the mixing chamber and driven out of a plane of the first opening to a depth of greater than one times the depth of the first opening to form a mixed fluid; and passing the mixed fluid out of an outlet opening out of the mixing chamber.

The methods of mixing described herein may include passing the first fluid and the second fluid through the first opening into the mixing chamber so that the first and second fluids are driven against the wall of the mixing chamber and out of the plane transverse to the first opening to the depth of greater than about 2.5 times the depth of the first opening.

Any of the methods of mixing described herein may be single mixing chamber mixers in which only a single mixing chamber (e.g., box mixer) is used, which can achieve substantially complete mixing. Thus, these single mixing chambers may achieve a high level of mixing in a very small footprint in a microfluidic device. The mixed fluid may be substantially mixed by the mixing chamber and the mixing chamber may be configured as a single mixer that does not connect to a second mixing chamber.

For example, a method of mixing within a microfluidic device may include: passing a first fluid and a second fluid through a first opening into a mixing chamber within a microfluidic device, so that the first and second fluids are driven against a wall of the mixing chamber and out of a plane transverse to the first opening to a depth of greater than about 2.5 times the depth of the first opening to form a substantially mixed fluid; and passing the mixed fluid out of an outlet opening out of the mixing chamber, wherein the outlet opening is opposite from the first opening but is offset from the first opening, wherein the mixed fluid is substantially mixed by the mixing chamber and the mixing chamber is configured as a single mixer that does not connect to a second mixing chamber.

Alternatively, these methods may be configured so that mixing is performed by linking, in series, two or more (e.g., 3, 4, 5, 6, etc.) mixing chambers. For example, a method may include passing the mixed fluid from the outlet opening into a second opening into a second mixing chamber, so that the fluid is driven against a wall of the second mixing chamber and driven out of a plane of the second opening to a depth of greater than one times the depth of the second opening to further mix the mixed fluid.

The fluid may be driven against the wall of the mixing chamber and out of the plane transverse to the first opening to a depth of about 3 or more times the depth of the first opening. The outlet opening may have a cross-section area that is equal to a cross-sectional area of the first opening. The mixing chamber may have a length that is greater than the width, and wherein the length is greater than about 2 times the width of the first opening. The mixing chamber may have rounded corners. The change in fluid pressure through the mixing chamber at a flow rate of between 0.25 and 5 ml/min may be between about 6.9 kPa and about 206.8 kPa. The width of the mixing chamber may be between about 150 and about 600 μm, the depth of the mixing chamber may be between about 150 and about 500 μm, and the length of the mixing chamber may be between about 500 μm and about 1000 μm.

All of the methods and apparatuses described herein, in any combination, are herein contemplated and can be used to achieve the benefits as described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative examples, in which the principles of the invention are utilized, and the accompanying drawings of which:

FIGS. 1A and 1B are schematic representations of mixing apparatus according to some examples of the disclosure.

FIG. 3C shows an enlarged view of the mixer (mixing apparatus) of FIG. 3B.

FIGS. 7A-7D illustrate examples of mixing apparatuses of different configurations. FIG. 7A shows a one-chamber mixing apparatus. FIG. 7B shows a three serially connected mixers as described herein. FIG. 7C shows an example of six serially connected mixers as described herein. FIG. 7D shows an example of twelve serially connected mixers as described herein.

FIGS. 9A-9B show a first example of mixing apparatus having three serially connected mixers ("3 box" mixers) of different sizes. In FIG. 9A each mixer of the mixing apparatus forms a box of 250 μm by 200 μm by 500 μm. In FIG. 9B, each mixer of the mixing apparatus is scaled up by twofold compared to the apparatus shown in FIG. 9A, so that each box forming each mixer is 500 μm by 400 μm by 1000 μm.

FIG. 9C is a graph comparing the mixing effects of the larger (scaled up) mixing apparatus shown in FIG. 9B ("3 box L") and the mixing apparatus shown in FIG. 9A ("3 box"). The bar graph shows the Z-average value, scale on left, while the dots show the polydispersity index (PDI), scale on the right.

FIG. 11A shows a top perspective view of the mixing apparatus, while FIG. 11B shows a sectional view through an upper (top) region of the mixing apparatus. The angle between adjacent mixers in FIGS. 11A and 11B is 135 degrees.

In FIG. 11C, the bar graph shows the Z-average value, scale on left, while the dots show the polydispersity index (PDI), scale on the right.

In FIG. 13, the bar graphs show the volume mean values, scale on left, while the dots show the polydispersity index (PDI), scale on the right. Four instances of 1 ml/min are shown, four instances at 2 ml/min are shown, and 2 instances of 4 ml/min are shown, along with a single hand mixed sample.

FIGS. 14A-14B illustrate one example of a dialyzer, shown in perspective and cross-sectional views, respectively.

FIG. 15 is a cross-sectional view of one example of an edge region of a dialyzer similar to that shown in FIGS. 14A-14B.

FIGS. 17A-17C are illustrations of flow rate through another example of a dialyzer apparatus as shown herein, showing flow rate through the device.

DETAILED DESCRIPTION

Figure 2A:
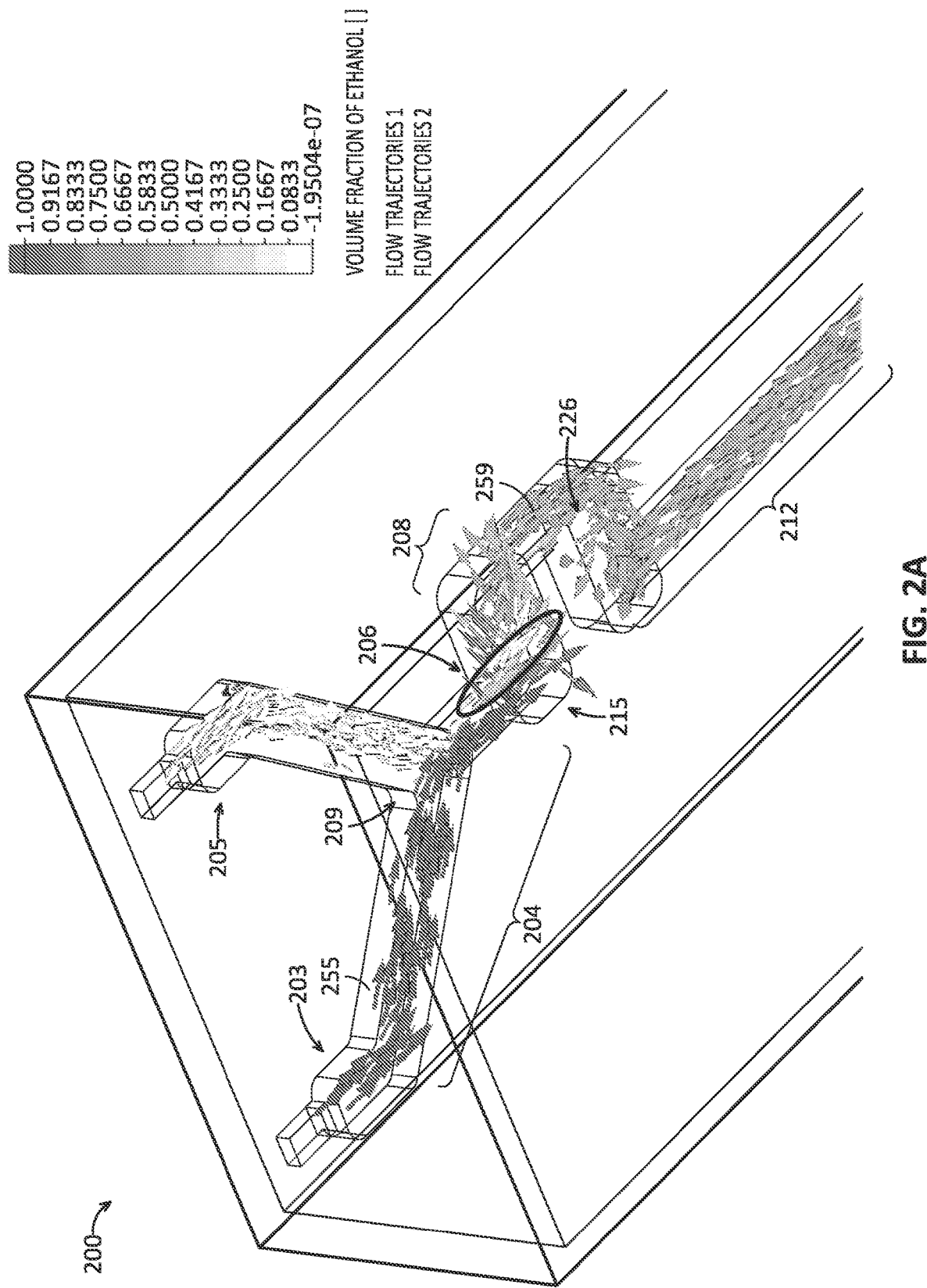
FIGS. 2A to 2C schematically illustrates mixing behavior for one example of a mixing apparatus.

In general, described herein are apparatuses (e.g., systems, devices, etc.) and methods for processing fluid mixtures, including but not limited to therapeutic polynucleotides. In particular, described herein are mixing apparatuses that may mix materials in a microfluidic apparatus more quickly and efficiently, using less microfluidic space, than previously described microfluidic mixers. Any of the mixing apparatuses described herein may include one or more mixers, which may be referred to as box mixers or vortex mixers; which may be connected in series and may be included as part of a microfluidic apparatus. For example, any of these apparatuses and methods may be used as part of a closed path microfluidic apparatus and method that may be configured to minimize, and in some instances even eliminate, manual handling. A closed path apparatus and method may provide a substantially aseptic environment and may form a sterile path for processing from initial input (e.g., template) to output (compounded therapeutic). As used herein, the term "substantially" may refer to mostly or essentially all/essentially completely (e.g., greater than 90%, greater than 95%, greater than 97.5%, greater than 99%, greater than 99.5%, greater than 99.9%, etc.), and may include all or completely. For example, "substantially mixed" may refer to a mixture that is mostly or completely mixed, that is, mixed to homogeneity. Material inputs (nucleotides, and any chemical components) into the apparatus may be sterile and may be input into the system without requiring virtually any manual interaction. The mixing apparatuses described herein may allow for complete and thorough mixing of these components for forming and/or compounding a composition using a microfluidic apparatus.

Thus, the mixing methods and apparatuses described herein may be used to generate therapeutics at rapid cycle times at high degree of reproducibility. Thus, the mixing methods and apparatuses described herein may allow a microfluidic apparatus to provide, in a single integrated apparatus, synthesis, purification, and compounding of one or more therapeutic compositions (including, but not limited to therapeutic polynucleotides). All or some of these processing steps may be performed in an unbroken fluid processing pathway, which may be configured as one or a series of consumable microfluidic device(s), which may also be referred to as a microfluidic path chip, microfluidic path plate, process chip, biochip, or process plate. This may allow for patient-specific therapeutics to be synthesized, including compounding, at a point of care (e.g. hospital, clinic, pharmacy, etc.).

During operation of the apparatus the fluid path may remain unbroken, and contamination may be substantially eliminated by non-contact monitoring (e.g., optically monitoring), including fluid flow measurement, mixing monitoring, etc. and by manipulating precise microfluidic amounts (metering, mixing, etc.) using pressure applied from a deflectable membrane on an opposite side of the fluidic chambers and channels.

These apparatuses and methods may be configured for use at a point of care. For example, the methods and apparatuses described herein may be configured for manufacturing customized therapeutic compositions including one or more therapeutic polynucleotide (e.g., mRNA, microRNA, DNA, etc.).

Thus, the methods and apparatuses described herein may provide scalable polynucleotide manufacturing, production of single patient dosages, elimination of touchpoints to limit contamination, input and process tracking for meeting clinical manufacturing requirements, and use in point-of-care operations for therapeutics. The microfluidic instrumentation and processes described herein can provide major advantages.

In general, the apparatuses described herein may be microfluidic apparatuses. In some examples, these microfluidic apparatuses may include closed path microfluidic apparatus for processing biomolecular products, such as, but not limited to therapeutic polynucleotides, which can include mixing and formulating (e.g., combining with a selected carrier or vehicle) biomolecular products. These apparatuses may be configured to operate on one or more microfluidic device. The microfluidic apparatus may include one or more microfluidic device (e.g. blending chip, formulation chip, etc.).

The mixing apparatuses described herein are surprisingly effective and may be implemented along the microfluidic flow path. These mixing apparatuses may be part of a microfluidics fluid path device that is in or between a pair of layers of material separated by a deflectable membrane. The fluid path, including the mixing apparatus, may be formed on one side of the deflectable membrane (e.g., by forming in the first layer or layers on one side of the membrane, and the membrane may form the top of the mixing apparatus; the plate on the opposite side of the membrane may be flat. In some examples the plate on the opposite side of the deflectable membrane may be cut-out and may form a chamber opposite of the mixer, which may be connected to a pressure channel to allow deflection of the membrane into the mixer and/or into the upper chamber, e.g., to drive fluid.

The mixing apparatuses described herein may include one or more individual mixers, which may be arranged in series and connected by channels having a smaller height and/or width. The mixers may be referred to as mixing components, box mixers, or vortex mixers. Examples of these mixers are described in greater detail herein. Thus, the mixing apparatus including one or more mixers may be referred to collectively as a "microfluidic mixing apparatus," a "box mixing apparatus" or "vortex mixing apparatus" or simply as a "mixing apparatus". The mixers described herein may employ vortex mixing within a vortex mixing chamber (e.g., a "box" or series of fluidly connected boxes) to efficiently mix a non-uniform incoming stream or pulse of fluid material to obtain a more uniformly mixed fluid mixture across a very small distance along the microfluidic flow path. This may be achieved over a wide range of fluidic mixtures. One or more of the fluids to be mixed may further include particles such as nanoparticle enclosed drug substances or the like. Efficient mixing may also be obtained over a wide variety of ratios of components entrained within the fluids introduced for mixing, as discussed in detail below. In some examples of the mixing apparatuses described herein the fluid are believed to form a vortex within the chamber of the mixing apparatus, so that the direction of fluid flow may double back onto itself, in a circular, vortex pattern. As illustrated in the fluid modeling provided below. Thus, these mixing apparatuses may be referred to as vortex mixers or vortex mixing chambers. It should be understood that referring to them mixing and mixing apparatuses described herein as vortex mixing or vortex mixing chambers is not intended to limit these methods and apparatuses to a particular theory of operation.

FIG. 1A shows a microfluidic mixing apparatus 100, having two fluidic inlet channels 103 and 105 which are offset from each other and are configured to transport one or more substances (e.g., biomolecular product(s), buffers, carriers, subsidiary components) that may be combined together. Although two inlet channels are shown, three or more (4, 5, 6, etc.) may be used, and may converge on the same mixer. The fluids to be mixed may transit the inlet channels under positive pressure. This pressure may be constant, variable, increasing, decreasing, and/or pulsatile. The mixing apparatus is configured to be disposed along a microfluidic flow path between an input terminus and an output terminus, where mixed and formulated biomolecular products may be exported from the microfluidic flow path and apparatus. The microfluidic apparatus may have a first, or upper, plate and a second, or lower plate. The microfluidic flow path and microfluidic components (mixer, pumps, etc.) may be formed therebetween, and may be machined, molded or manufactured in any suitable manner. The microfluidic flow path may have one or more widths along the flow path and may have one or more vertical dimensions. Generally, the upper surface defining the microfluidic path may be at the same level throughout the microfluidic flow path of the apparatus.

In FIG. 1A, the microfluidic mixing apparatus receives fluid from two fluidic channels 103, 105, which may each have a width, e.g., of between about 50 to about 500 µm (e.g., between about 50 to about 400, between about 50 to about 300, between about 50 to about 200, about 170 µm, about 150 µm, about 110 µm, about 100 µm, about 80 µm, about 60 µm, about 50 µm, etc.). The channels may have the same width (and/or cross-sectional diameter) or may have different widths (and/or cross-sectional diameters). The channels 103, 105 may have a vertical dimension of between about 20 and about 200 µm (e.g., about 200 µm, about 175 µm, about 150 µm, about 125 µm, about 100 µm, about 75 µm, about 60 µm, about 50 µm, about 40 µm, or any value therebetween). The two channels 103, 105 intersect at a fluidic intersection 109, merging the two streams of fluid together. The channels meet at an angle 107. The angle 107 may be less than about 180 degrees (e.g., between 5 degrees and 179 degrees, between 10 degrees and 160 degrees, between 15 degrees and 145 degrees, between 30 degrees and 120 degrees, etc.). In some examples, the angle 107 may be about 30 degrees or greater (e.g., the angle 107 may be about 35 degrees, about 40 degrees, about 50 degrees, about 60 degrees, about 75 degrees, about 90 degrees, about 100 degrees, about 120 degrees, about 145 degrees, about 160 degrees, or any value therebetween).

The merged channel, leaving the fluidic intersection 109, may have a width, e.g., of between about 50 µm to about 200 µm (e.g., between about 50 to about 180, between about 50-150, between about 50-140, between about 50-130, between about 50-120 µm, about 110 µm, about 100 µm, about 80 µm, about 60 µm, or about 50 µm, etc.). The merged channel is a mixing inlet channel, and may have a vertical dimension that matches one or more (e.g., all) of the inlet vertical dimension(s), e.g., about 100 µm, about 75 µm, about 60 µm, about 50 µm, about 40 µm, or any value therebetween. The mixing inlet channel has a first terminus comprising a fluidic intersection and a second terminus comprising the opening into the vortex mixing chamber. The mixing inlet channel enters a vortex mixing chamber 115, where the channel has a mixing inlet opening 111 into the vortex mixing chamber 115 through a side wall of the vortex mixing chamber 115.

Increasing the vertical dimension 121 of the vortex mixing chamber 115 so that it is greater than the vertical dimension 119 of the mixing inlet channel opening 111, and in some examples being greater than the vertical dimension 123 of the opening 113 of the mixing outlet channel, results in surprisingly enhanced mixing. FIG. 1B shows one example of a microfluidic mixing unit 130. One example of the vortex mixing chamber provides a common upper surface for both the mixing chamber 115 and the inlet channel opening, thus forcing the incoming fluid to drop vertically towards the lower surface. Additionally, the vortex mixing chamber 115 may be configured so that the fluid exits the vortex mixing chamber 115, at an outlet opening 113 of a mixing outlet channel. The outlet opening may be configured similarly to the opening 111 into the mixing chamber, e.g., the vertical dimension of opening 113 in this example is smaller than the vertical dimension of the vortex mixing chamber 115, and may share the same upper surface as the vortex mixing chamber; the height and/or cross-sectional area of the outlet may be the same as that of the inlet opening 111. To exit the vortex mixing chamber 115, fluid is forced to move upward as well as laterally; the inlet and outlet openings 111, 113 are also disposed on opposing sides (and in FIG. 1B on opposite walls) of the vortex mixing chamber 115. In some examples, the openings 111, 113 are disposed vertically through the side walls of vortex mixing chamber 115 such that the upper limit of the openings 111, 113 (e.g., the upper surface defining the mixing inlet channel and the mixing outlet channel) are at the same vertical dimension as the upper surface of the vortex mixing chamber 115. The openings 111, 113 are additionally disposed on the opposing side walls of the vortex mixing chamber 115, offset horizontally from each other. The fluid is forced to form a vortex around a horizontal axis of the box and mix strongly as it moves from opening 111 to opening 113 of the mixing outlet channel. In general, the outlet opening is offset from the inlet opening so that the fluid will deflect from a sidewall of the chamber opposite to the inlet and deflect "down" towards the bottom surface as part of the mixing.

In general, the vortex mixing chamber 115 has a base defining a bottom surface, one or more side walls, and an upper surface enclosing the vortex mixing chamber. The vortex chamber may have a rectangular, oval, circular, hexagonal, etc. shape; the sidewalls may be curved (e.g., having a radius of curvature 127 that is between 0.5 times and 0.01 times the length of the shortest sidewall to which it connects). As mentioned, a mixing inlet channel and a mixing outlet channel each open into the vortex mixing chamber at a first and a second side wall of the vortex mixing chamber, respectively. The size of the vortex mixing chamber 115, 120 and mixing inlet/mixing outlet channels may be selected to provide efficient mixing for a particular overall flow rate or range of flow rates.

In some examples, the mixing inlet channel and/or the mixing outlet channel may each have a width of between about 50 to about 200 µm (e.g., between about 50 and 170 µm, about 170 µm, about 110 µm, about 100 µm, about 80 µm, about 60 µm, about 50 µm, etc.). The mixing inlet channel and/or the mixing outlet channel may each have a vertical dimension of about 75 µm, about 60 µm, about 50 µm, about 40 µm, or any value therebetween. In some examples, the mixing inlet channel and the mixing outlet channel may have the same width and the same height as each other.

A mixing assembly may include a plurality of vortex mixing chambers that are linked together so that the inlet of the subsequent vortex mixing chamber is linked to the outlet of the prior vortex mixing chamber, as shown in FIG. 1A; a connecting channel 132 may be connected between each vortex mixing chamber. The microfluidic vortex mixing units may have the same shape and/or dimensions or may be different shapes and/or dimensions.

In some examples the microfluidic vortex mixing unit(s) 130 may have a length of between about 250 µm to about 1100 µm (e.g., about 300 µm, about 350 µm, about 400 µm, about 500 µm, about 600 µm, about 1000 µm, about 1100 µm, or any length therebetween). The vortex mixing chamber may have a width of between about 175 µm to about 600 µm (e.g., about 200 µm, about 250 µm, about 275, about 400 µm, about 500 µm, about 600 µm, or any width therebetween). In some examples, the chamber may have a height of between about 125 µm to about 500 µm in a vertical dimension (e.g., about 125 µm, about 150 µm, about 170 µm, about 200 µm, about 250 µm, about 300 µm, about 400 µm, about 500 µm, or any height therebetween). As mentioned, in some examples, the corners of the vortex mixing chamber may be rounded, and a corner may have a radius of curvature 127 of from about 50 µm to about 90 µm, or about 50 µm, about 60 µm, about 75 µm, about 80 µm, about 90 µm, or any radius therebetween. Dimensions of the vortex mixing chamber and the mixing inlet/outlet channels may be selected to allow for straightforward machining and minimizing the change in fluidic pressure (delta P) while maximizing mixing in within a small distance. Efficient usage of microfluidic chip surface area also is included within the design considerations. For example, mixing/size selection factors may include a vortex mixing chamber height that is between about 2 times and about 5 times (e.g., about 2 times, 3 times, 4 times, 5 times, between about 2 times—about 4 times, etc.) the height of the mixing inlet/outlet channels. In some examples, the vortex mixing chamber height is about 3 times the height of the mixing inlet/outlet channels. The length of a side wall of the vortex mixing chamber may be about two or more times (e.g., about 2 times, about 3 times, about 4 times, between about 2 times—about 5 times, between about 2 times—about 4 times, etc.) of the width of the mixing inlet/outlet channels.

In general the dimensional specifications of the mixing chambers provided herein are exemplary; for example, the dimensions provided above may be used for a mixer having a flow rate of between about 0.1 to 10 ml/min (e.g., between about 0.2 ml/min to about 5 ml/min, between about 0.5 ml/min to about 4 ml/min, etc.). The dimensions described herein may be scaled up or down to provide larger or smaller flow rates (e.g., at different dimensional values) in order to achieve the same vertical flow (e.g., equivalent mixing) for a particular applied pressure (e.g., between about 6.99 kPa and about 206.8 kPa). Thus, the dimensions provide herein may be scaled (e.g., scaling of these structures) in order to allow for different flow rates.

For example, a microfluidic mixing apparatus may include a mixing inlet channel, a microfluidic vortex mixing chamber and a mixing outlet channel, where the mixing inlet and mixing outlet channels have a width of about 100 µm and a vertical dimension from the base of the mixing inlet/outlet channel(s) of about 50 µm; a vortex mixing chamber having a length of 350 µm, a width of 250 µm, a height of 150 µm, and a radius of curvature of about 75 µm at the rounded corners of the chamber. The mixing inlet opening 111 is therefore offset along the 350 µm long side wall horizontally away from the mixing outlet opening 113 along the opposite 350 µm long side wall by up to about 150 µm.

In another example, a microfluidic mixing apparatus may include a mixing inlet channel, a microfluidic vortex mixing unit and a mixing outlet channel, where the mixing inlet and mixing outlet channels may have a width of about 150 µm and a vertical dimension from the base of the mixing inlet/outlet channel(s) of about 50 µm; a vortex mixing chamber having a length of 500 µm, a width of 250 µm, a height of 150 µm, and a radius of curvature of about 75 µm at the rounded corners of the chamber. The mixing inlet opening 111 is therefore offset along the 500 µm long side wall horizontally away from the mixing outlet opening 113 along the opposite 500 µm long side wall by up to about 200 µm.

As mentioned, a vortex mixing unit 130 may be disposed along the microfluidic flow path paired with a second (or more) vortex mixing unit, similarly to the pair of vortex mixing units shown in FIG. 1A. The second vortex mixing unit may be configured similarly to the first vortex mixing unit. That is, vortex mixing chamber 115 and 120 may have the same dimensions as each other, to provide similar vortexing and mixing characteristics as desired above. For example, the respective mixing inlet and outlet channels may be related as follows: the first mixing outlet channel of the first vortex mixing unit may have a first terminus including the opening 113 into the first vortex mixing chamber 115 and a second terminus including the second mixing inlet channel comprising the opening 131 into the second vortex mixing chamber 120 of the second vortex mixing unit. The second mixing outlet channel, e.g., of the second vortex mixing unit, has a first terminus at the opening 133 into the second vortex mixing chamber 120, and a second terminus at the outlet 117 from the mixing apparatus, along the microfluidic path. The pair of two microfluidic vortex mixing units may be designed to minimize the pressure drop (Delta P) and for a smaller pair of mixing units having a vortex chamber with a 350 µm length, 250 µm width, and 150 µm height, as described above, the Delta P per pair at a 0.5 ml/min flow rate is about 10.3 kPa (e.g., between about 6.9 kPa and about 206.8 kPa, between about 6.9 kPa and about 172.4 kPa, between about 6.9 kPa and about 106.0 kPa, between about 6.9 kPa and about 103.4 kPa, between about 6.9 kPa and about 68.9 kPa, between about 6.9 kPa and about 34.5 kPa, etc.). A pair of vortex mixing units having the larger dimension where the chamber is 500 µm long, 250 µm wide and 150 µm deep, has a Delta P at a 1 ml/min flow rate of about 2.4 psi (16.5 kPa).

Figure 3A:
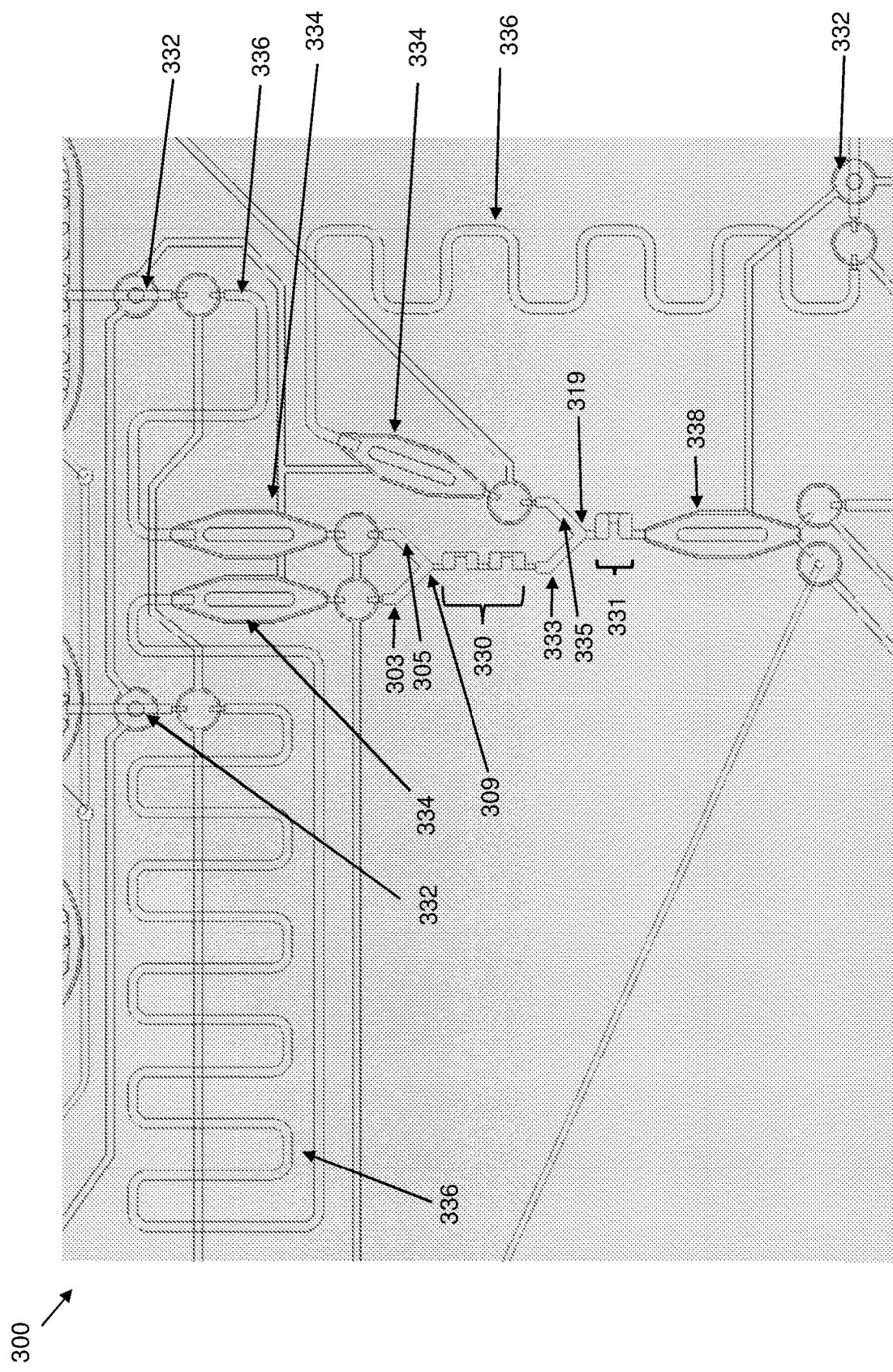
FIG. 3A schematically illustrates one example of an apparatus (e.g., microfluidic apparatus) including a mixer (e.g., mixing apparatus) as described herein.

In some examples, a third or fourth microfluidic vortex mixing unit(s) may be included along the microfluidic flow path, as shown in FIG. 3A, to provide a two-stage mixing apparatus. The first chained group of mixing units 330 is a first stage; this mixed product may then be combined with a second group of mixing units 331 at a second stage. The additional microfluidic vortex mixing units may be configured like the microfluidic vortex mixing units described above. Generally, each individual vortex mixing unit may have the same features and dimensions, or different dimensions. In FIG. 3A, the first stage 330 includes four mixing units (e.g., two pairs of mixing units) that may be connected as shown. For example, a second terminus of the second mixing outlet channel is continuous with a third mixing inlet channel and an opening into a third vortex mixing chamber. A third mixing outlet channel may have a first terminus that includes an opening into the third vortex mixing chamber and a second terminus that may be the fourth mixing inlet channel and an opening into a fourth vortex chamber. A fourth mixing outlet channel may have a first terminus that may be an opening into the fourth vortex mixing chamber and a second terminus that may be an output from the microfluidic mixing apparatus.

Figure 2B:
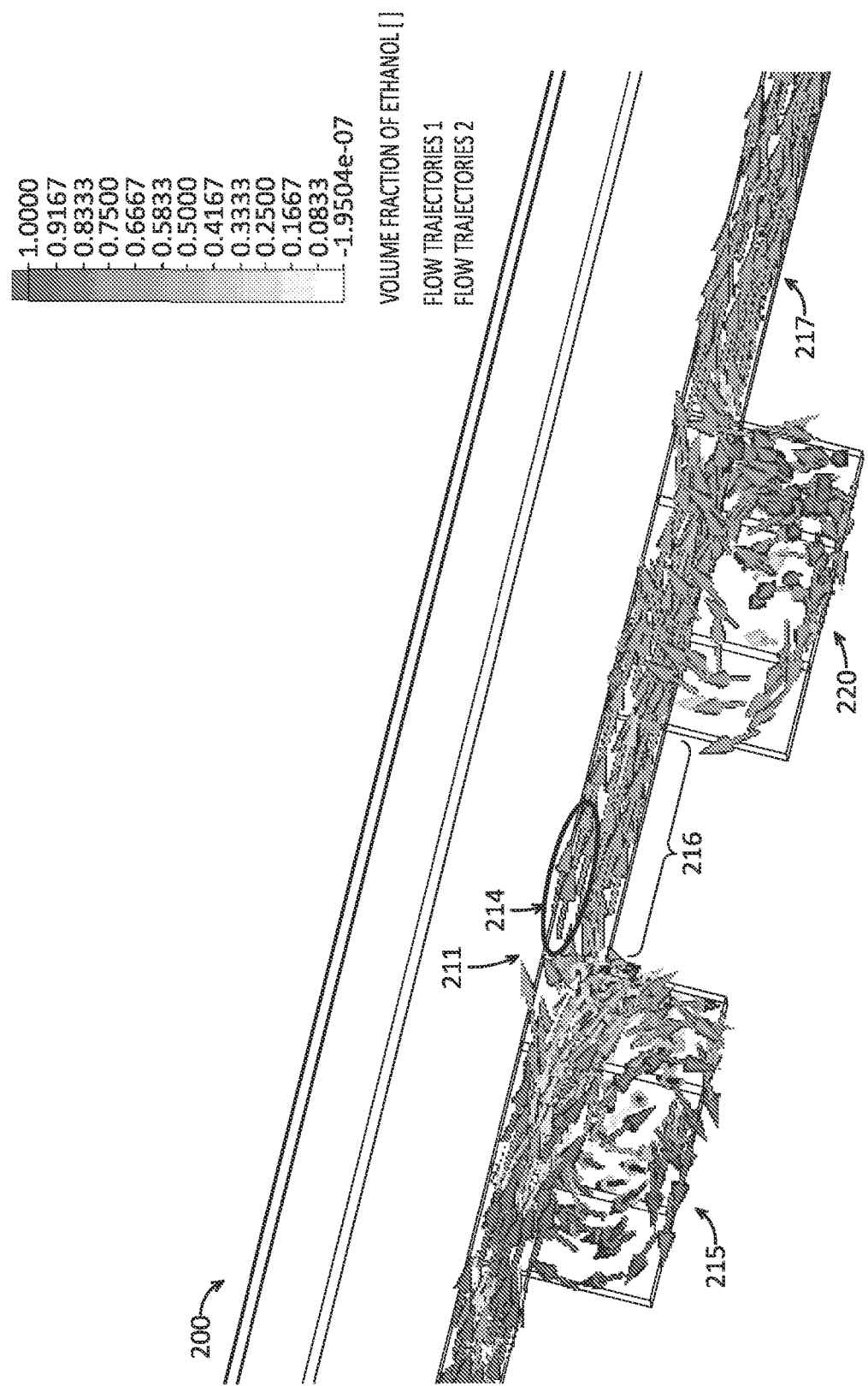

Returning now to FIGS. 2A-2C, FIG. 2A shows flow trajectory modelling for the microfluidic mixing apparatus 200, which is similar to the mixing apparatus 100 of FIG. 1A, having one pair of microfluidic vortex mixing units 130, and demonstrates the mixing capability of the microfluidic mixing apparatuses (showing mixing of equal parts ethanol (arrows 255) and water (arrows 257), by mixing fraction). The shading of the arrow indicates the mixing fraction. In FIG. 2A the perspective flow model for a 1:1 mixture of ethanol, introduced at the first inlet 203, and water, introduced at the second inlet 205. The volume fraction of ethanol to water along the microfluidic flow path shown by the arrows indicates substantial mixing in the vortex mixer. Inlet 203 is labeled to represent the 100% volume ethanol fraction, while second inlet 205 is labeled to show that there is no ethanol present. At fluidic intersection 209, the flows are moving laminarly without much mixing, as indicated by region 204, which shows distinct and unmixed ethanol and water flow. However region 206, encompassed by the white oval, shows abrupt change of concentration of ethanol as the fluid flow cascades down into vortex mixing chamber 215 (which may be like 115, 120 of generic microfluidic vortex mixing unit 130), where the aqueous edge of the flow is now about 0.1667 fraction of ethanol (v/v). As the flow reaches the mixing outlet opening region 208, the flow now contains nearly an equivalent volume fraction of ethanol, and the rest of the flow (arrows 259) within region 212 is a 0.5000 mixture (v/v) of ethanol. FIG. 2B shows a representation for a similar experiment, showing a side view within both a first and a second vortex mixing unit (215, 220) along the microfluidic path, both of which may be like 115, 120 of generic microfluidic vortex mixing unit 130. The side view of FIG. 2B more clearly shows the vortexing movement that the fluid is forced to flow in, in order to exit the vortex mixing chamber 215. The flow of 1:1 ethanol:water v/v can be shown to be substantially mixed to somewhere between 0.4167 to 0.5833 ethanol/water v/v at the opening 211 of the mixing outlet channel from the vortex mixing chamber 215. In this example, there is a small region at 214 where volume fraction as high as 0.667 still is present, but throughout most of region 216, the 0.4167 to 0.5833 ethanol/water v/v ratios are predominant. A second vortex mixing unit 226 may be used for final mixing within vortex mixing chamber 220 to produce thoroughly mixed ethanol/water at the second output 217 from the pair of microfluidic vortex mixing units. Within the vortex mixing chambers, the arrangement of the chamber allows for mixing in which the flow is directed down towards the bottom of the chamber, as shown in FIG. 2B. As will be described in greater detail below, the enhanced mixing temperature may be determined by calibrating the geometry, and particularly the depth of the chamber, and the flow rate, permitting nearly complete mixing in a single vortex mixing chamber.

Figure 2C:
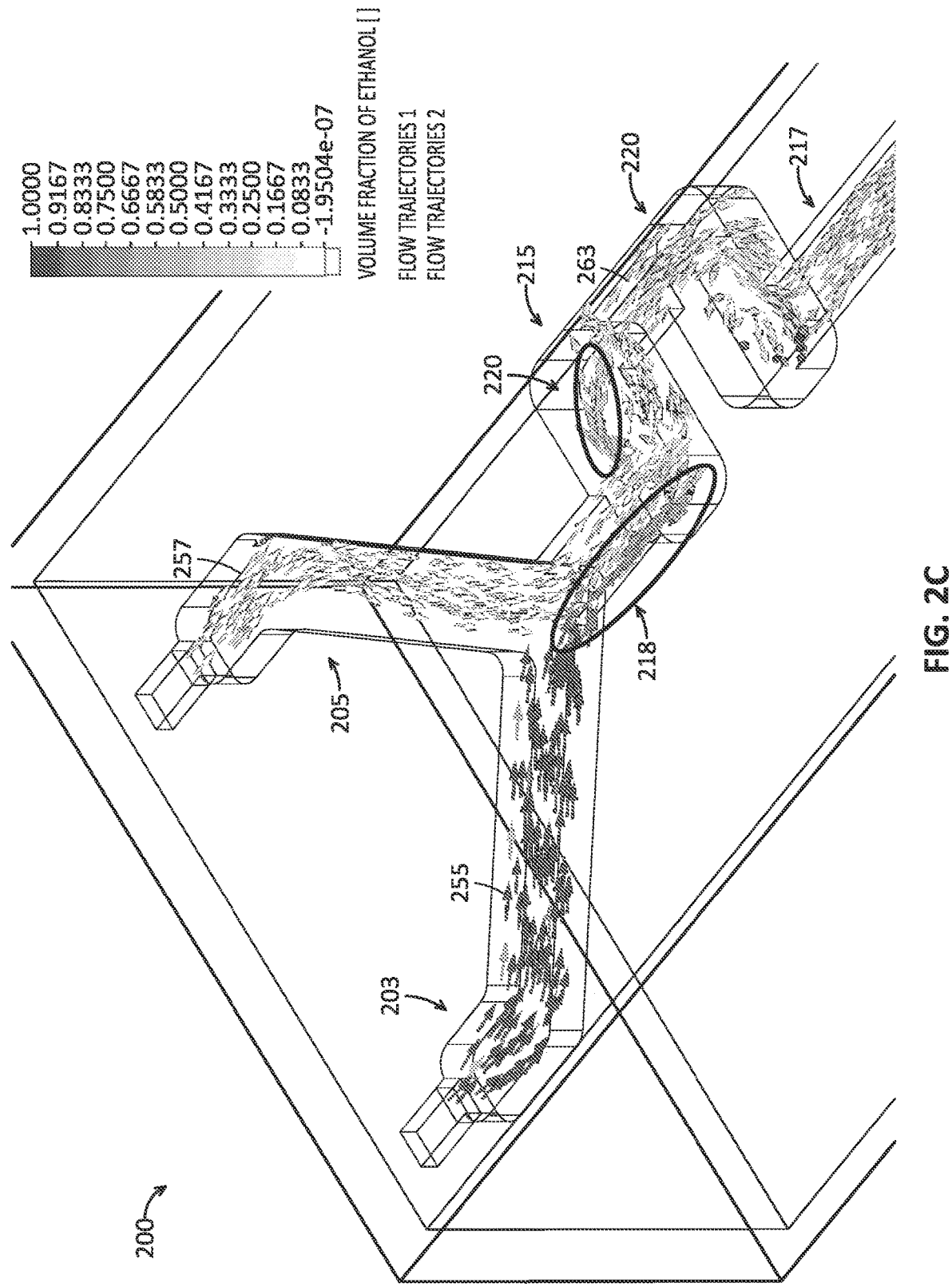

Another flow modelling example is shown in FIG. 2C, showing a ratio of 1:10 ethanol (input at inlet 203) to water (input at inlet 205). The shading indicates the fraction of ethanol to water (per scale). Region 218 shows the side-by-side flow of ethanol/water where the volume fraction of ethanol is already reduced to between 0.7500 to 0.4167, as the flow starts to cascade down into the vortex mixing chamber 215. Region 220 shows a portion of the flow having a slightly elevated volume fraction of ethanol between 0.1667 to 0.2500, but at the point of exiting the second vortex mixing chamber 220, the volume fraction of ethanol 263 has been completely equilibrated, and is outputted from the microfluidic mixing apparatus at 217. The arrangement of the mixing inlet opening, mixing outlet opening, vortex mixing chamber as shown provides a mixing apparatus that is substantially insensitive to the ratio of the fluids being mixed, as both a 1:1 ratio and a 1:10 ratio of fluids in the two inlet channels are brought to an equilibrated mixture upon exiting the mixing apparatus at 217.

FIGS. 2D-2J illustrate examples of other vortex mixing apparatuses showing the effects of examples in the configuration of the vortex mixing chamber on total mixing at exemplary pressures and flow rates.

Figure 2E:
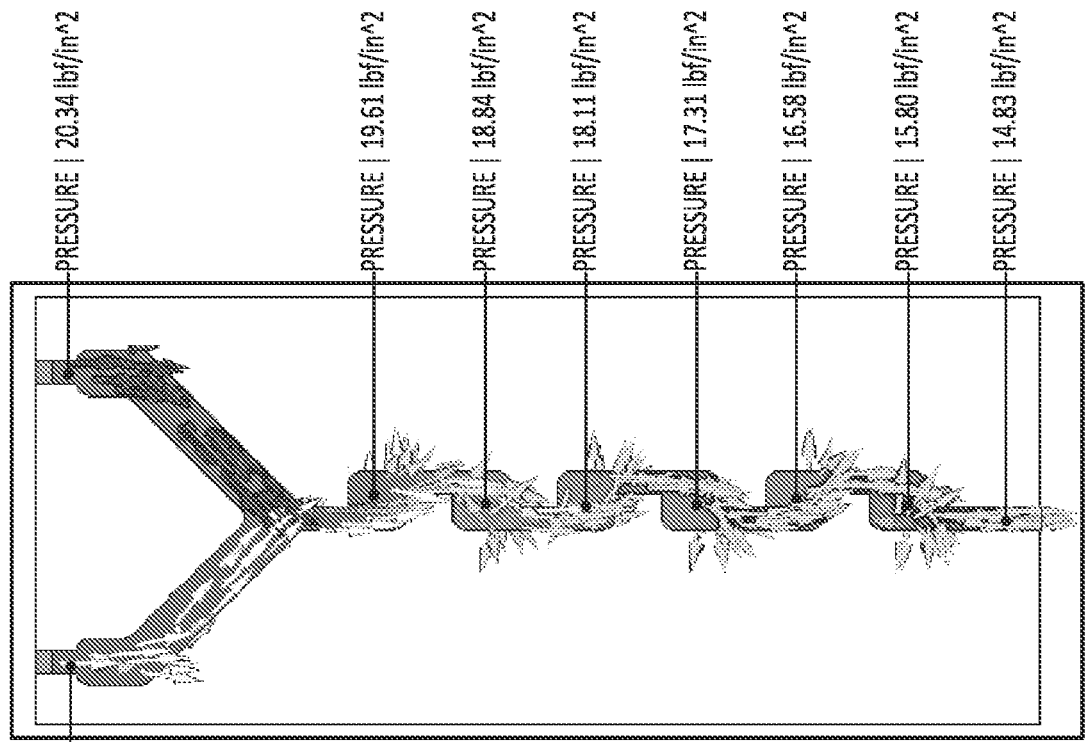
FIGS. 2D and 2E illustrate another example of a mixing apparatus as described herein, showing the mixing of ethanol:water.
Figure 2D:
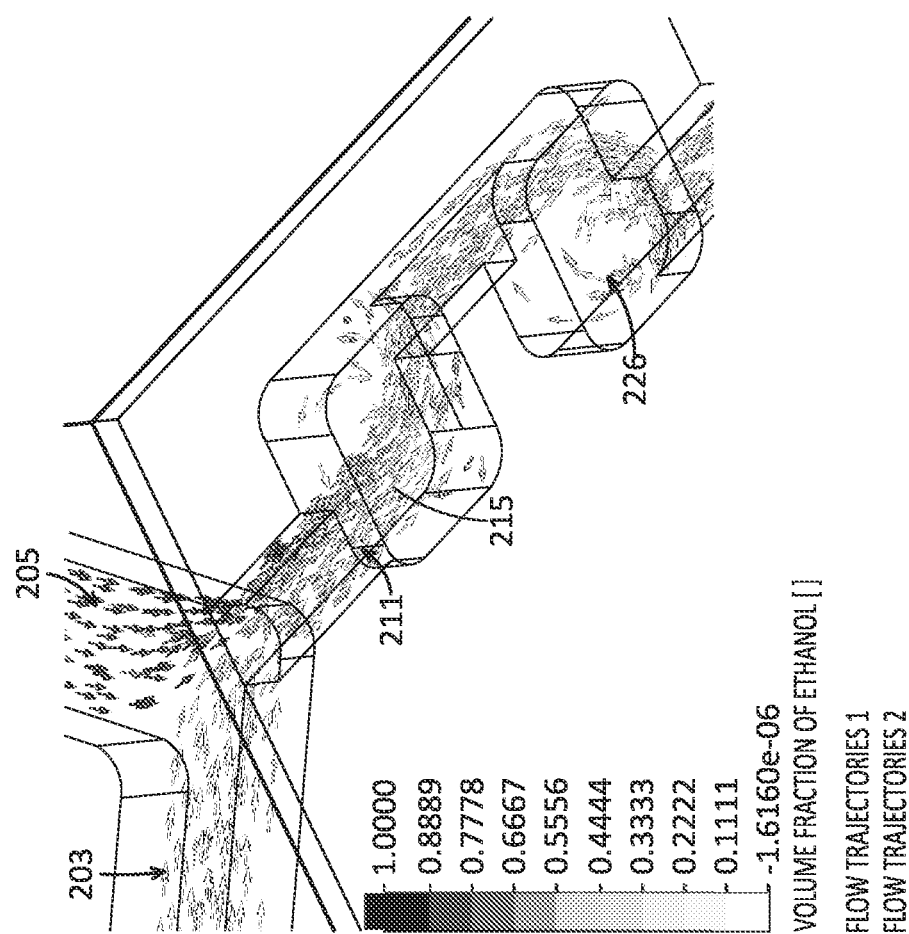

For example, FIGS. 2D-2E show an example of an apparatus including a series of vortex mixing chambers in which each of the channel inlets 211 is 100 μm wide by 50 μm deep. The depth is measured from the top surface (e.g., top plate), and the vortex mixing chamber is approximately square (with rounded sides), having a length that is 250 μm, a width of 250 μm and a depth of 100 μm. Thus, in this example, the depth of the vortex mixing chamber is 2 times the depth of the inlet, where the inlet opening and the chamber have a common upper surface, so that the maximum drop from the inlet opening to the top (or bottom, depending on the frame of reference) of the vortex mixing chamber is approximately the same as the depth of the inlet. In this case, as shown by the shaded arrows, for a 1:10 mixture of ethanol:water, mixing is not complete after the second sequential vortex mixing chamber 226 (connected in series). FIG. 2E shows the pressure drop for the same example (showing six sequentially connected vortex mixing chambers). Mixing is substantially complete by the third mixing chamber. The pressure drops from each of the water 205 and ethanol 203 supply channels of about 20.3 lbf/in$^2$, dropping by about 0.76 lbf/in$^2$ between each sequential vortex mixing chamber.

Figure 2G:
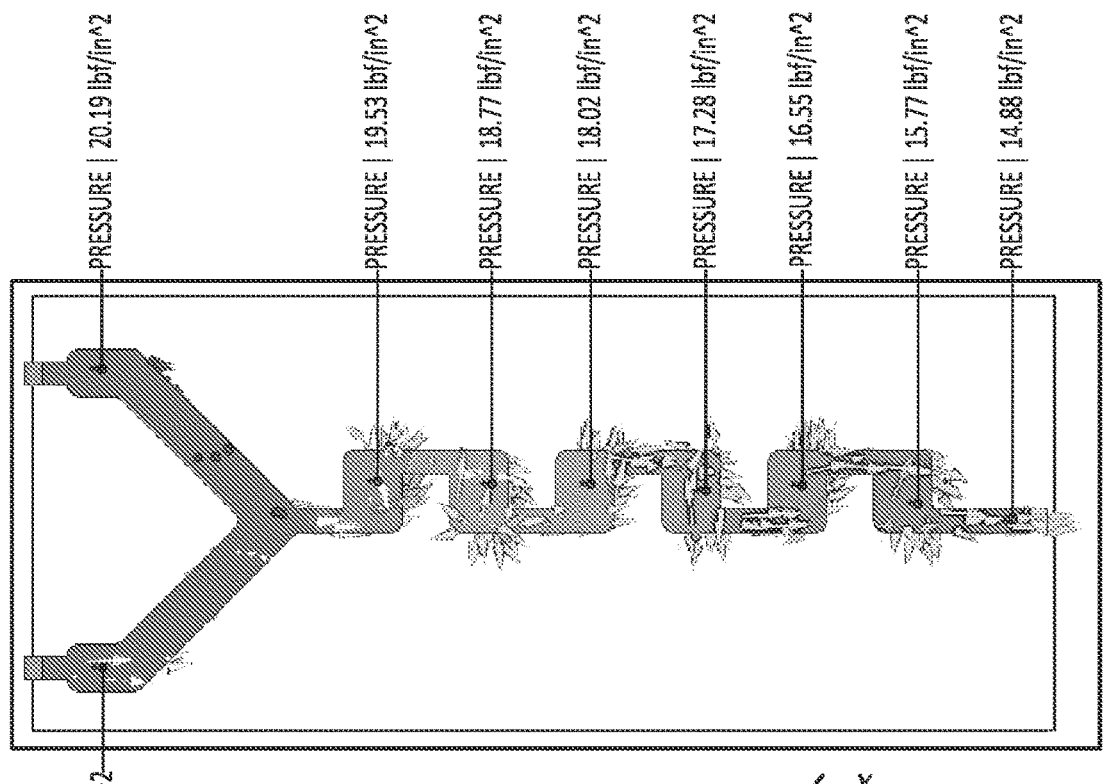
FIGS. 2F and 2G illustrate another example of a mixing apparatus as described herein, showing the mixing of ethanol:water.
Figure 2F:
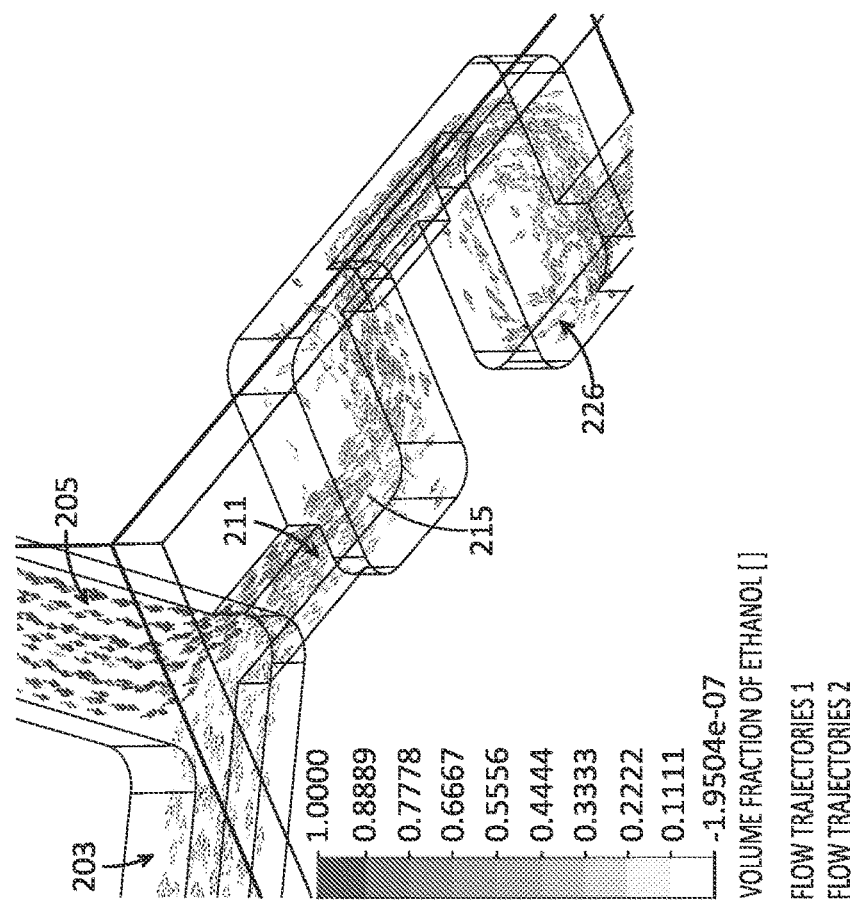

FIGS. 2F and 2G show another example of an apparatus including a series of vortex mixing chambers in which each of the channel inlets 211 is also (as in FIGS. 2D-2E) 100 μm wide by 50 μm deep. The vortex mixing chamber in this example is approximately rectangular (with rounded sides), having a length that is 350 μm, a width of 250 μm and a depth of 100 μm. Thus, this example has vortex mixing chambers that are 1.4 times as long but are otherwise similarly dimensioned as shown in FIGS. 2D and 2E, above. In FIGS. 2F and 2G the depth of the vortex mixing chamber is also 2 time the depth of the inlet, where the inlet opening and the chamber have a common upper surface, so that the maximum drop from the inlet opening to the top (or bottom, depending on the frame of reference) of the vortex mixing chamber is approximately the same as the depth of the inlet. The mixing profiles for 1:10 ethanol:water (shown by the shaded arrows) is nearly the same as in the example of FIGS. 2D and 2E. FIG. 2G shows the pressure drop for the same example (also showing six sequentially connected vortex mixing chambers). Mixing is substantially complete after leaving the second mixing chamber. The pressure drops from each of the water 205 and ethanol 203 supply channels of 20.19 (e.g., 20.19 lbf/in$^2$ and 20.19 lbf/in$^2$), dropping by about 0.75 lbf/in$^2$ between each sequential vortex mixing chamber.

Figure 2I:
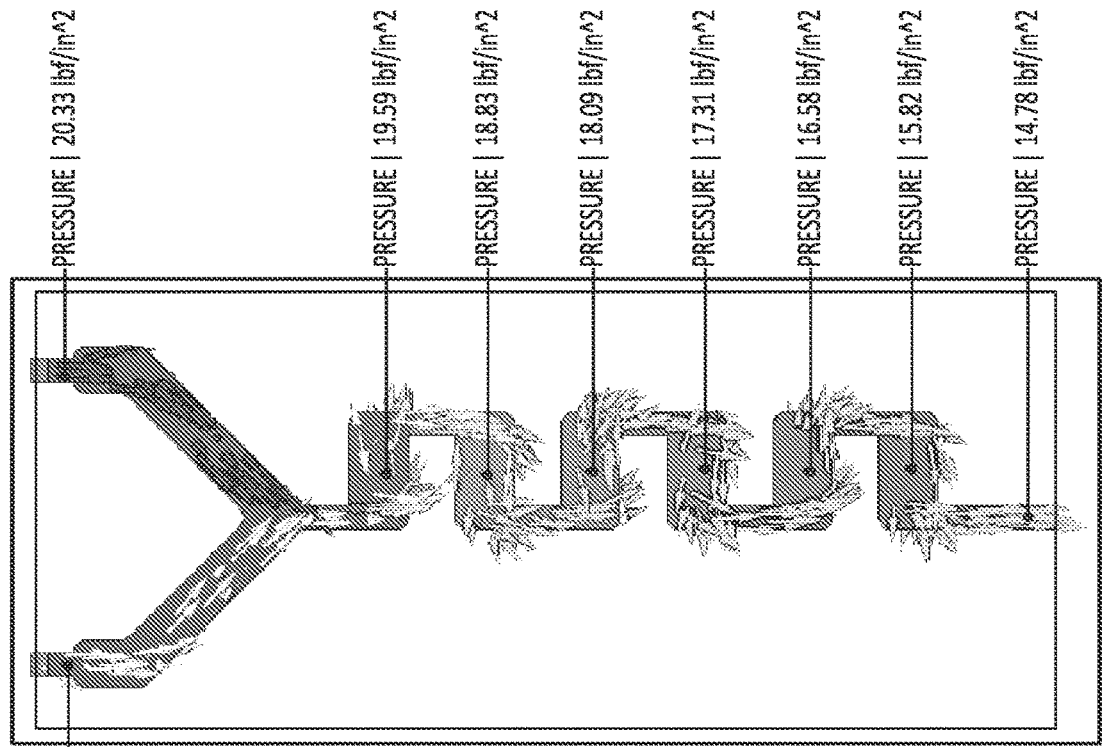
FIGS. 2H and 2I illustrate another example of a mixing apparatus as described herein, showing the mixing of ethanol:water.
Figure 2H:
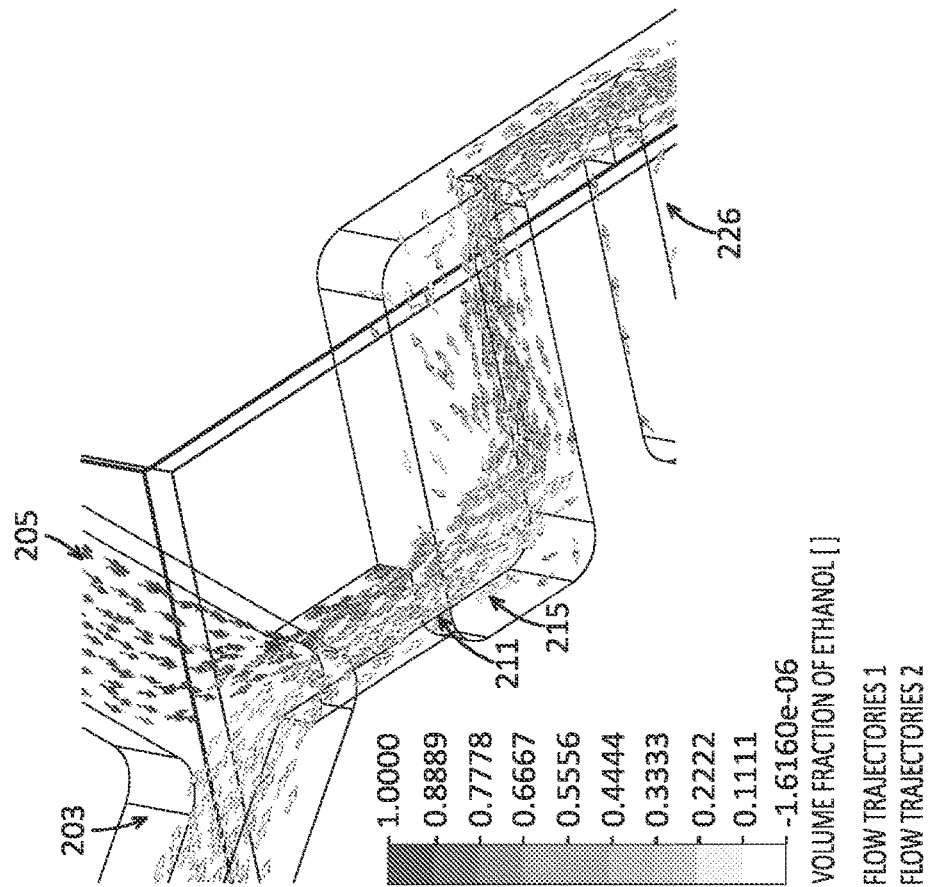

FIGS. 2H and 2I show an example of an apparatus including a series of vortex mixing chambers in which each of the channel inlets 211 is also (as in FIGS. 2D-2G) 100 μm wide by 50 μm deep. The vortex mixing chamber in this example is approximately rectangular (with rounded sides), having a length that is 500 μm, a width of 250 μm and a depth of 100 μm. Thus, this example has vortex mixing chambers that are twice as long but are otherwise similarly dimensioned as shown in FIGS. 2D and 2E, above. In FIGS. 2H and 2I the depth of the vortex mixing chamber is also 2 times the depth of the inlet, where the inlet opening and the chamber have a common upper surface, so that the maximum drop from the inlet opening to the top (or bottom, depending on the frame of reference) of the vortex mixing chamber is approximately the same as the depth of the inlet. The mixing profiles for 1:10 ethanol:water (shown by the shaded arrows) is nearly the same as in the example of FIGS. 2D and 2E. FIG. 2I shows the pressure drop for the same example (also showing six sequentially connected vortex mixing chambers). Mixing is substantially complete after leaving the second mixing chamber. The pressure drops from each of the water 205 and ethanol 203 supply channels of about 20 (e.g., 20.33 lbf/in$^2$ and 20.37 lbf/in$^2$), dropping by about 0.75 lbf/in$^2$ between each sequential vortex mixing chamber.

Figure 2J:
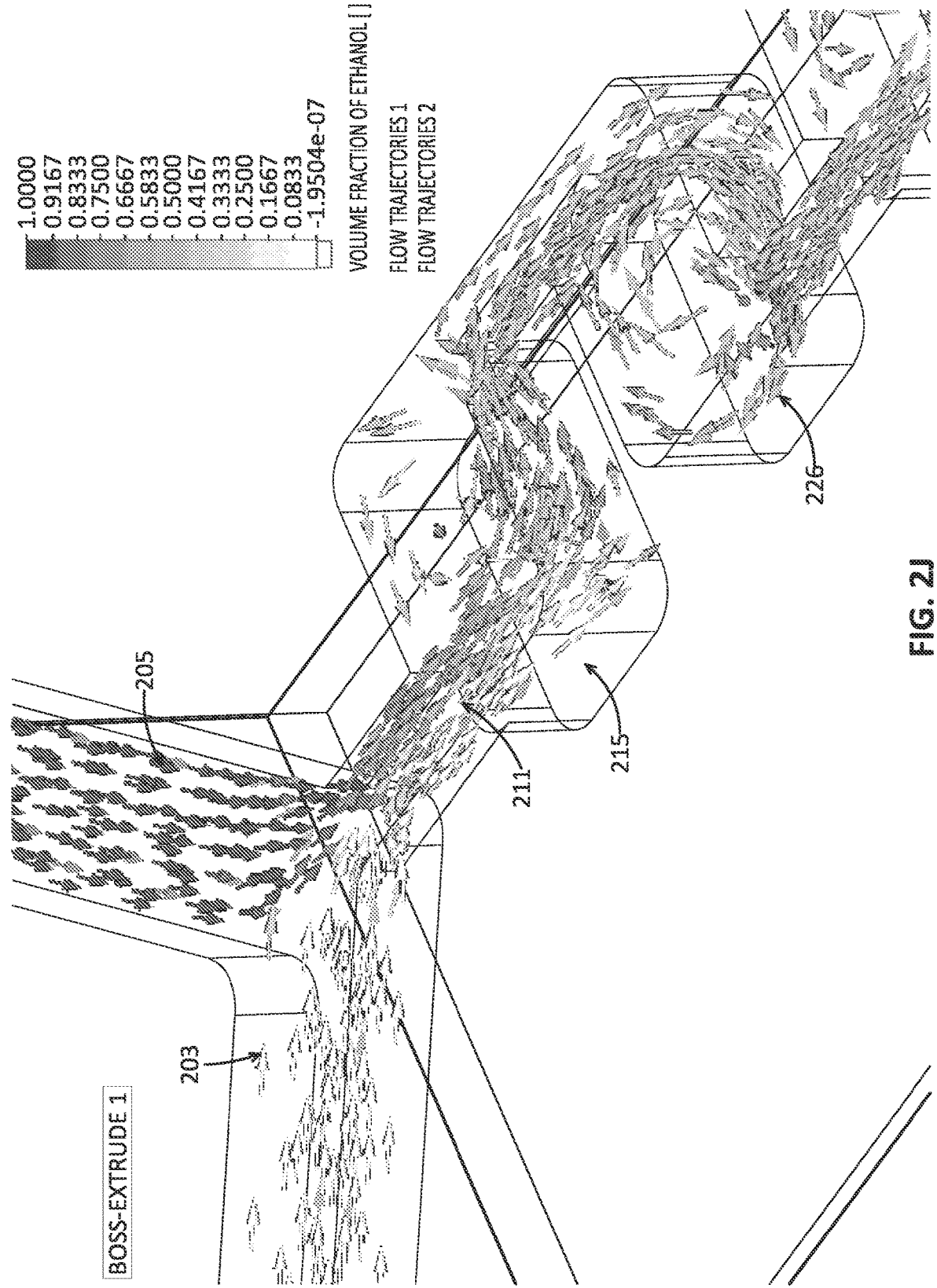
FIG. 2J illustrates mixing in another example of a mixing apparatus as described herein.

FIG. 2J shows an example of an apparatus including a series of vortex mixing chambers in which each of the channel inlets 211 are again, as shown in FIGS. 2D-2I, 100 μm wide by 50 μm deep. The vortex mixing chamber in this example is approximately rectangular (with rounded sides) but is nearly 3 times as deep as the channel inlet opening. In FIG. 2J, the vortex mixing chamber has a length that is 350 μm, a width of 250 μm and a depth of 150 μm. Thus, this example has vortex mixing chambers that have a similar shape to those shown in FIGS. 2F-2G but have a depth that is 50% larger. Thus, in FIG. 2J the depth of the vortex mixing chamber is 3 times the depth of the inlet, where the inlet opening and the chamber have a common upper surface, so that the maximum drop from the inlet opening to the top (or bottom, depending on the frame of reference) of the vortex mixing chamber is approximately 2 times the depth of the inlet. The mixing profiles for 1:10 ethanol:water (shown by the shaded arrows) show that the mixing in this example at these pressures and flow rates are highly efficient, showing nearly complete mixing after the first vortex mixing chamber, as shown by the arrows indicating the volume faction of ethanol. The pressure drop between vortex mixing chambers is approximately the same as shown in FIGS. 2D-2I. Thus, at these pressures and flow rates, the relative drop from the inlet into the vortex mixing chamber appears to strongly correlate with mixing efficiency, as compared, e.g., to chamber length. In the mixing model of FIG. 2J, the vorticity and complete mixing was achieved in one stage.

Any of the vortex mixing chambers described herein may be part of a microfluidic mixing apparatus; a microfluidic mixing apparatus may include one or more vortex mixing chambers. A microfluidic mixing apparatus may be implemented as part of a microfluidic device. For example, a microfluidic mixing apparatus used as part of a microfluidic apparatus for mixing and formulating biomolecular products is shown in FIGS. 3A-3E and 4. As mentioned above, the microfluidic apparatus may be formed from a first plate and a second plate, and the microfluidic flow path may be formed in portions of one or both plates. In FIG. 3A, the microfluidic apparatus 300 may include an elastic layer disposed between the first plate and the second plate. This apparatus also includes two mixing regions 330, 331, and is configured to mix materials from three distinct inputs 303, 305, 335. Similar to the mixing apparatuses described above, a first fluid is introduced to a first fluidic input 303 and a second fluid is introduced into a second fluidic input 305, which intersect at fluidic intersection 309, which may be configured like fluidic intersection 109. The fluids may be configured to be driven at a pressure greater than atmospheric pressure, assisted by inlet valves 332 (e.g., where positive or negative pressure may be applied). The merged flow continues into four vortex mixing chambers 330, arranged sequentially along the microfluidic flow path. Each of the individual vortex mixing chambers of the mixing apparatus 330 may be configured like microfluidic vortex mixing unit 130 describe above and may have any of the dimensions as described above. The two-stage mixing apparatus may be configured to output the mixed fluid via a single output from the final microfluidic vortex mixing chamber (the fourth in the series).

Apparatus 300 is further configured to mix a third fluidic component. After outputting the mixed fluid from the first stage mixing apparatus 330, the output channel becomes a third fluidic inlet 333 and intersects with a fourth fluidic inlet 335, introducing the third fluidic component at a second fluidic intersection 319, as described above. The merged fluid flow is then input into a vortex mixing chamber of the second mixing stage 331, which is disposed sequentially along the microfluidic flow path. Each of the vortex mixing chambers of this second stage 331 may be configured like any of microfluidic vortex mixing chambers described above. Complete mixing may be achieved using a single vortex mixing chamber in either the first or second stage mixing paths, however in some examples the additional mixing chambers may allow further mixing, and may provide a buffer for examples in flow rate. The mixed fluid from traversing through the vortex mixing chambers may be output in a single channel from the mixing pathway (e.g., from the second stage), and may continue along the microfluidic flow path for further processing in other regions of the microfluidic apparatus.

The microfluidic path apparatus 300 in FIG. 3A also includes vacuum caps 334, which may be held at negative pressure to remove gas from the liquid (fluidic) lines by drawing it through the membrane overlying the fluid path if it is gas permeable. PolyDiMethylSilicone (PDMS) elastomer film for example is sufficiently gas permeable to allow this. For the cascaded mixing apparatus shown in this example, there are three fluid driving chambers configured to drive each of the first, second and third fluidic components into the respective inlet channels. Each fluid driving chamber has a fixed volume and is formed between the first plate and the second plate. A portion of the elastic layer disposed between the first and the second plate, divides each fluid driving chamber into a fluid-contacting side in the second plate and a pressure-receiving side in the first plate. The pressure-receiving side may be pressurized to drive fluidic through the chamber and into the mixing apparatuses 330, 335. The fluid driving chambers each include a fluid port (from the microfluidic flow path) that fluidly connect with the fluid-contacting side of each of the respective first and second fluid driving chambers via a respective fluid channel in the second plate; and a pressure port extending through the first plate and into the second plate that fluidly connect with the pressure-receiving side of the fluid driving chamber via a respective pressure channel extending through the second plate and along the first plate. The volume of the fluid-contacting side of the fluid driving chamber may be adjusted by applying pressure or vacuum from the respective pressure port. The fluidic port of the fluid driving chamber may further include a flow restrictor 336. In some examples, the flow restrictor may include a serpentine elongate fluidic channel.

In general, the methods and apparatuses described herein may include the use of multiple fluids (e.g., materials in fluids, including mRNA, buffers, salts, delivery vehicles, etc.) that may be supplied from external reservoirs. Any of these methods and apparatuses may include one or more vacuum cap structures and valves to advance all fluids to a starting point, without bubbles, then release the fluids in a controlled way such that the mixing results are stable over the time of mixing. As mentioned above, the vacuum cap may be configured to reduce or remove bubbles from the fluid(s). The apparatuses and methods described herein may also include valves connecting to one or more waste collection regions. In some examples the initial results may be sent to waste output if needed to preserve the quality of the overall output.

The microfluidic mixing apparatus 300 may further include a fourth fluid driving chamber which may be disposed along the microfluidic flow path, subsequent to the mixing apparatus. In FIG. 3A, a vacuum cap 338 may be included. While two cascaded mixers are shown, additional mixers may be included as part of the fluid channel. In this manner the steps of forming a nanoparticle based therapeutic may be broken down into steps that are accomplished in a very timely and controlled manner along the cascade. For example in the first mixer a polynucleotide such as mRNA in water, may be mixed with a delivery vehicle molecule or molecules in ethanol to form complexed nanoparticles. A second mixer may be used to add a dilution agent such as a citrate-based buffer solution for pH adjustment. If more mixers are used additional steps could be included. For example it may be desirable to add a surface layer to the nanoparticles formed in the first mixing step to enhance bioactivity of the nanoparticles. This could be done by combining the output fluid stream of the first mixer with a solution containing the desired overcoating material in a second mixing structure. This could then be combined in a third mixer with a pH adjustment buffer solution. It might also be useful to create the mixture of polynucleotides and water in an upstream mixer structure where the polynucleotides and Delivery vehicle molecules are combined. In this way more concentrated polynucleotides as are typically produced in the mRNA production process could be diluted evenly with water prior to the nanoparticle formation step. Similarly upstream mixing of Ethanol and delivery vehicle molecules could be done before the mixer that combined the polynucleotide solution and delivery vehicle solution.

Figures 3B, 3C:
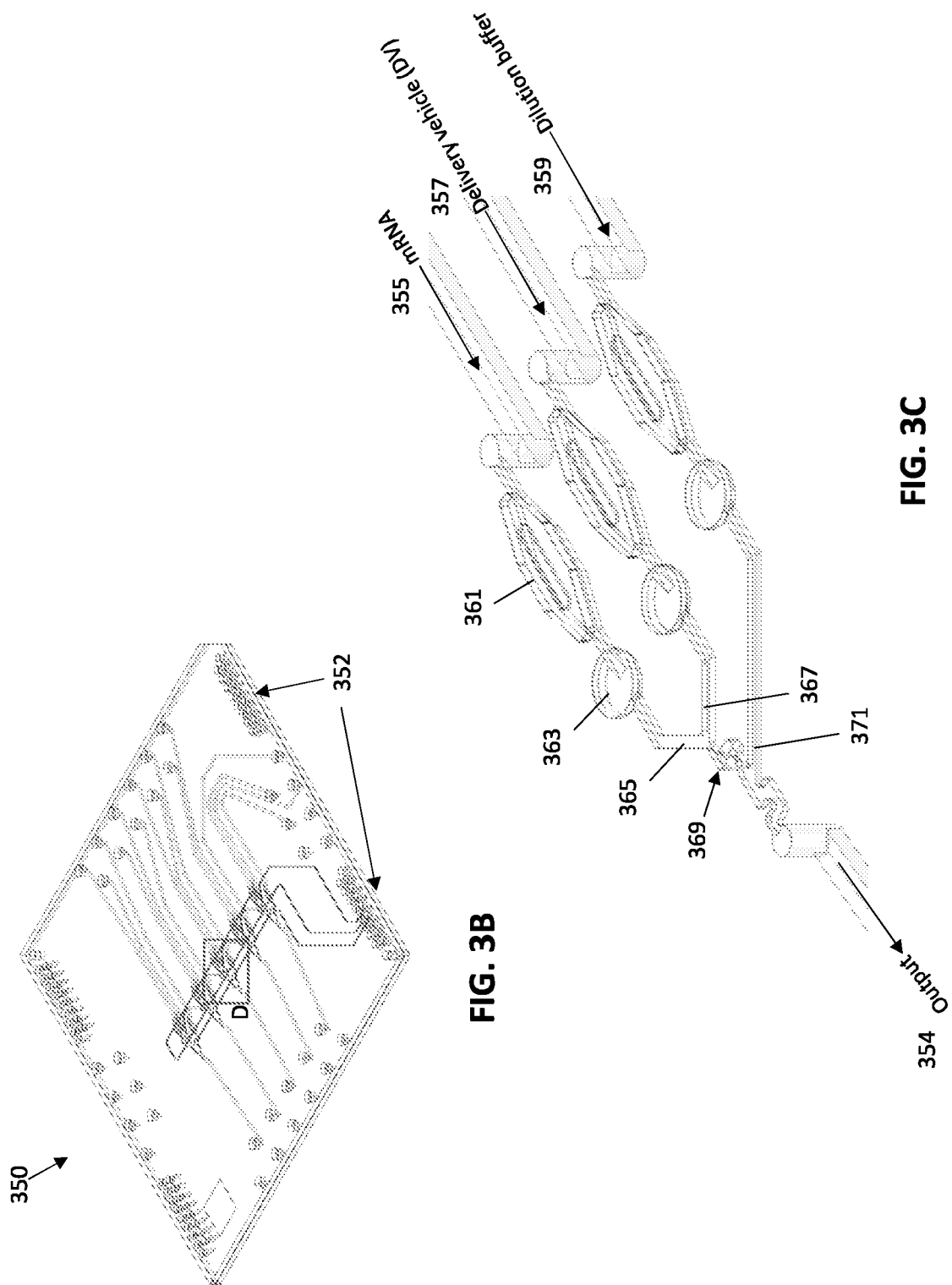
FIGS. 3B and 3C illustrate an example of a microfluidic apparatus including a mixer as described herein.

FIGS. 3B and 3C illustrate an example of a microfluidic apparatus configured as a continuous mixer. In FIG. 3B, the microfluidic apparatus 350 includes a plurality of mixers arranged in parallel. As described above, the microfluidic apparatus may include two or more plates, separated by a deflectable membrane, with chambers and channels formed in the upper and/or lower surfaces of plates, which may be divided by the membrane. In this example, the apparatus may be configured to receive multiple reagents, e.g., mRNA, delivery vehicle, diluent, etc., that may be directly pumped from reagent containers (e.g., vials, tubes, not shown) that are outside of the microfluidic apparatus (e.g., "chip"). The mixer maybe used to mix the reagents for dispensing off of the microfluidic apparatus, e.g., into a collection container (not shown). The microfluidic device may include ports for coupling to one or more pressure lines 352 that may be used to selectively apply pressure (e.g. positive and/or negative air pressure) to control one or more valves (e.g., allowing flow of the reagents on/off the chip). The reagents may be pressurized within the reagent containers, driving them onto the microfluidic apparatus if a valve allowing them to flow is opened.

FIG. 3C shows an enlarged view of region D of the apparatus 300 of FIG. 3B. In this example, the mixer 369 may be configured as a single mixer as describe herein. Three inputs for each of three reagents are shown, and include an mRNA input 355, a delivery vehicle input 357 and a diluent input 359. A valve 363 may be opened/or closed by selectively applying positive and/or negative pressure (e.g., by a controller) to allow fluid to flow. In the example shown in FIG. 3C, each reagent is also coupled to a vacuum cap 361 that may be used to remove air (e.g., bubbles) from the fluid before it is passed into the mixer 369. For example, the vacuum cap may apply negative pressure to draw air through a membrane that allows passage of air but not fluid.

In FIG. 3C the mixer 369 includes a first fluidic input 365 and a second fluidic input 367 that meet at a fluidic intersection channel that inputs into the mixer 369. In this example, the mRNA reagent is mixed with the delivery vehicle in the mixer, as described above. The output of the mixer forms an intersection with an input 371 for dilution buffer, just upstream of the output 354 of the microfluidic device ("chip").

In this example, the mixer may be operated continuously or nearly continuously, as the volume of material arrives from an off-chip container and the output from the chip may be stored in an off-chip storage container. Thus, in this example, fluid may be driven through the mixer directly by applying air pressure. In some cases, which may be used for smaller volumes, or more discrete (including metered) volumes of material, the fluid may be driven through the channels and/or mixer by defecting the membrane between plates of the microfluidic device.

Figure 3E:
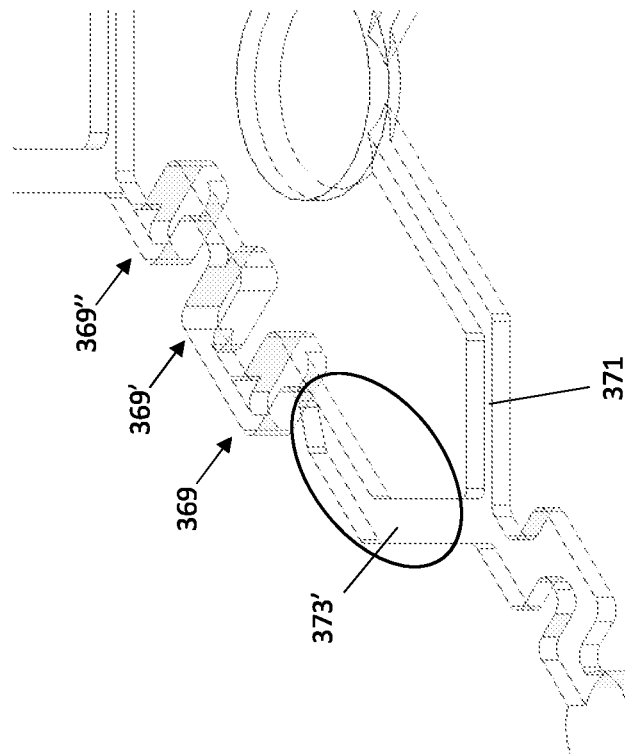
FIG. 3E is an example of an apparatus having a longer distance between the output of the mixer and a junction with a dilution buffer.
Figure 3D:
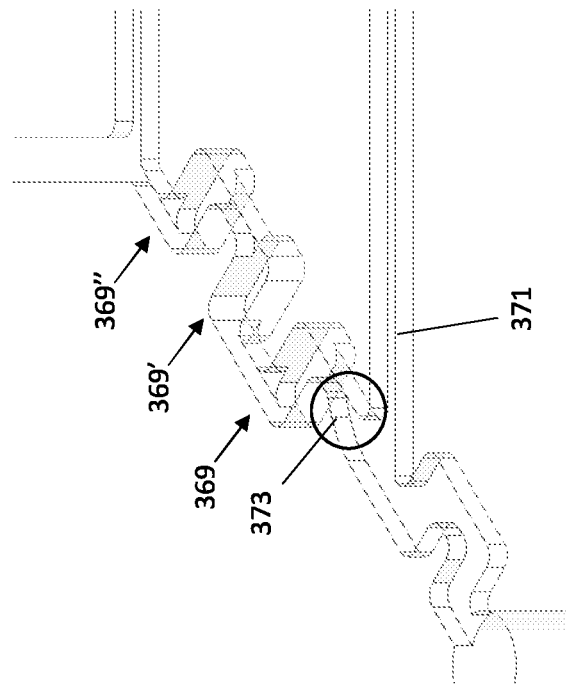
FIG. 3D shows another example of a mixer of a microfluidic apparatus having a short distance between the output of the mixer a junction with a dilution buffer.
Figure 8:
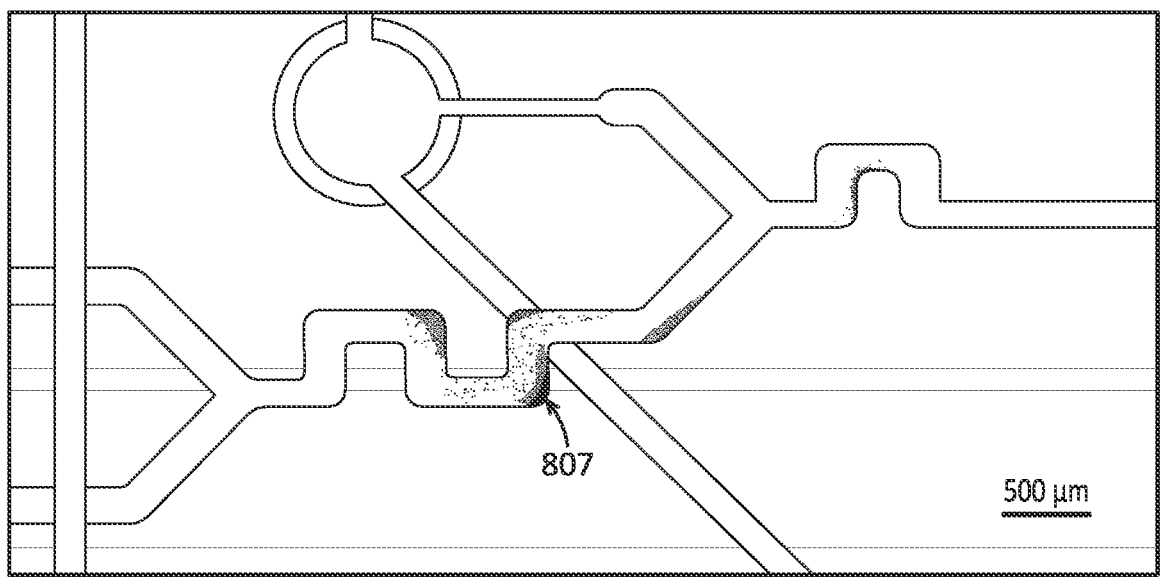
FIG. 8 is a picture illustrating a mixing apparatus including three serially connected mixers showing deposition within the mixers.

The example, shown in FIG. 3C may be configured to prevent clogging or deposition of material within the mixer, which is described in greater detail below in reference to FIG. 8. For example, FIGS. 3D and 3E illustrate examples of microfluidic apparatuses similar to that shown in FIGS. 3B and 3C, in which dilution buffer is added (with or without mixing using a mixer) to a mixed solution of reagents, e.g., mRNA and delivery vehicle, following mixing in a mixing chamber. In FIG. 3D the output channel 373 of the mixers 369, 369', 369" extends only a very short distance (e.g., less than about 100 µm, less than about 150 µm, less than about 200 µm, less than about 400 µm, less than about 500 µm, etc.) before intersecting with the dilution buffer input 371. In contrast, in FIG. 3E, the microfluidic apparatus is configured so that the output channel 373' of the three, serially-arranged mixers 369, 369', 369" if long, e.g., greater than about 600 µm, greater than about 700 µm, greater than about 800 µm, greater than about 900 µm, greater than about 1000 µm, etc.

Apparatuses in which the output channel is shorter than, e.g., 500 µm (about 400 µm, about 300 µm, etc.) may generally be more compact than other designs while still providing enhanced mixing. Further, less deposition of material may result when mixing with dilution buffer a very short distance from the input. Alternatively or additionally, shortening the distance between the first 369" and the second 369' mixer (or the second and the third 369) may also reduce or eliminate deposition. For example, the mixing apparatuses described herein may include less than about 500 µm (e.g., less than about 400 µm, less than about 300 µm, less than about 200 µm, less than about 100 µm) between serially arranged mixing chambers. In some examples, these apparatuses may include a dilution buffer input at or near the output of the mixing apparatus.

Figure 4:
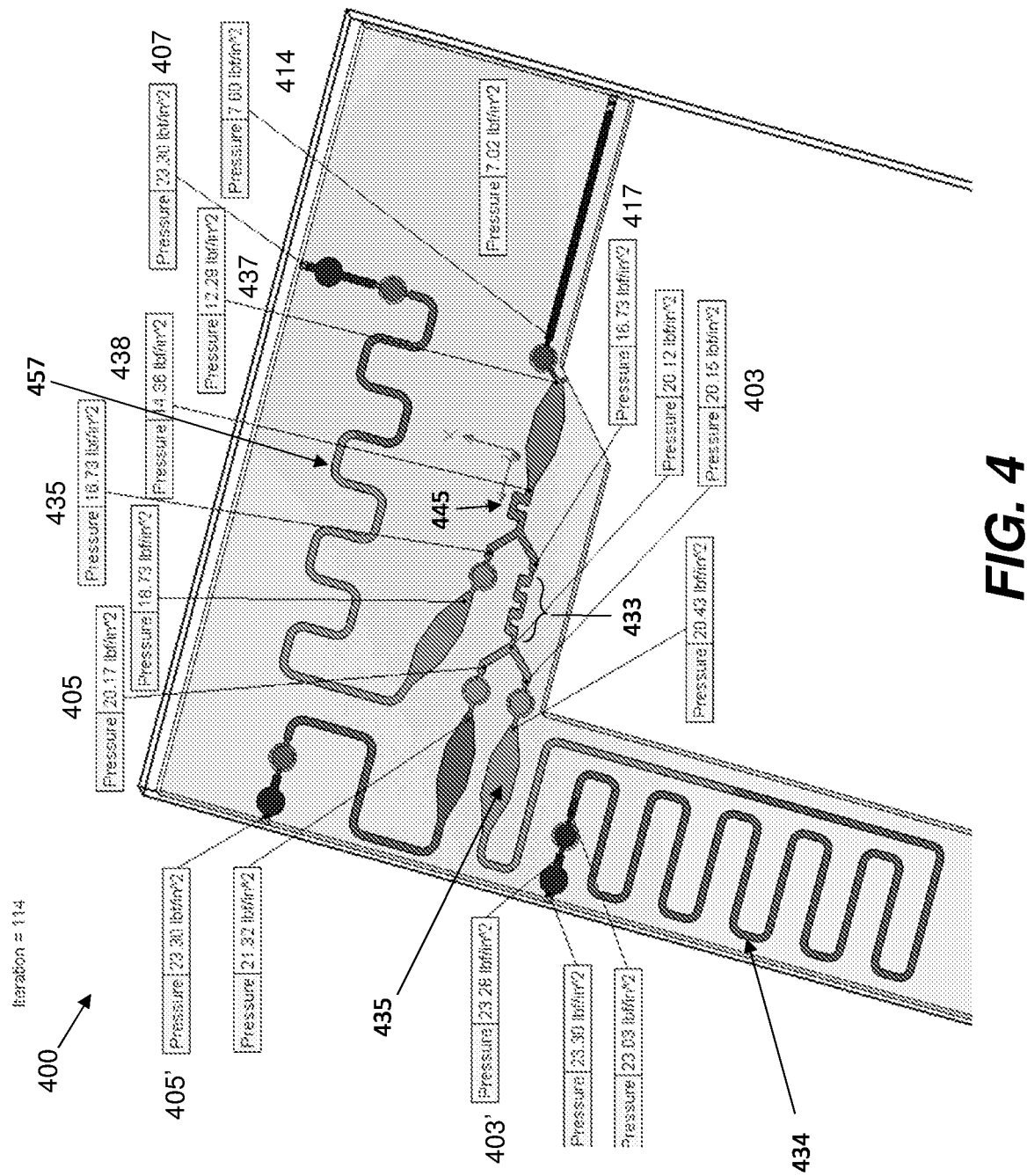
FIG. 4 is a schematic representation of selected characteristics for an example apparatus including an example mixer according to some examples of the disclosure.

FIG. 4 shows an example of portion of another microfluidic device also pressure drops across the apparatus 400, including a mixing sub-assembly 433 which is configured like apparatus 300. A first fluid component may be introduced into the microfluidic device at input 403'. In this example, the fluid flow is initiated at a pressure of 23.28 lbf/in$^2$ (160.5 kPa), and traverses through a flow restrictor 434, and vacuum cap 435, arriving at first fluidic inlet 403 at a pressure of 20.15 lbf/in$^2$ (138.9 kPa). The second fluid component is introduced at input 405' at a pressure of 23.30 lbf/in$^2$ (160.6 kPa), flowing through its respective flow restrictor and fluid driving chamber, to the second fluidic inlet 405 at a pressure of 20.17 lbf/in$^2$ (139.0 kPa). The two fluids intersect, at an equalized pressure, and are mixed in the first vortex mixing chamber, and may pass into subsequent sequentially arranged chambers of the mixing sub-assembly 433 until exiting at output 417, e.g., at 16.73 lbf/in$^2$ (115.3 kPa). The mixture may then enter a second stage 445 of the cascaded mixing apparatus, to intersect a third fluidic component at the second fluidic intersection. The third fluidic component in this example is input into the microfluidic path apparatus 400 at input 407, e.g., at a pressure of 23.30 lbf/in$^2$ (160.6 kPa), and traverses a flow restrictor 457 and to arrive at the fourth fluidic inlet 435 at 16.73 lbf/in$^2$ (115.3 kPa), pressure equalized to the fluid arriving from the third fluidic inlet 417. The merged flow passes through the last pair of vortex mixing chambers of the second stage of the mixing sub-assembly and enters a 438 at 14.36 lbf/in$^2$ (99.0 kPa). Pressure may be further reduced within 438, and fluid may be outputted at output 414, e.g., at a pressure of 7.60 lbf/in$^2$ (52.4 kPa). In some examples this mixing subassembly may be fluidly connected in-line with additional processing components, either on the same microfluidic device (microfluidic path apparatus) or a separate microfluidic device.

In general, the mixers described herein may be cascaded together. Cascaded mixers may provide additional mixing and may allow high degrees of mixing at increased flow rates. For example any of the microfluidic apparatuses described herein may include a plurality of cascading microfluidic vortex mixing apparatuses, wherein each microfluidic vortex mixing apparatus comprises: a vortex mixing chamber comprising a base defining a bottom surface, side walls, and an upper surface enclosing the vortex mixing chamber; a mixing inlet channel comprising an opening into the vortex mixing chamber at a first side wall of the vortex mixing chamber; a mixing outlet channel comprising an opening into the vortex mixing chamber at a second side wall of the vortex mixing chamber, wherein a vertical dimension of the vortex mixing chamber is larger than a vertical dimension of the mixing inlet channel and is larger than a vertical dimension of the mixing outlet channel; further wherein the plurality of microfluidic vortex mixers are connected in a series so that the mixing inlet channel of each of the microfluidic vortex mixers after a first microfluidic vortex mixer in the series is connected to the mixing outlet of a prior microfluidic vortex mixer in the series.

Figure 5:
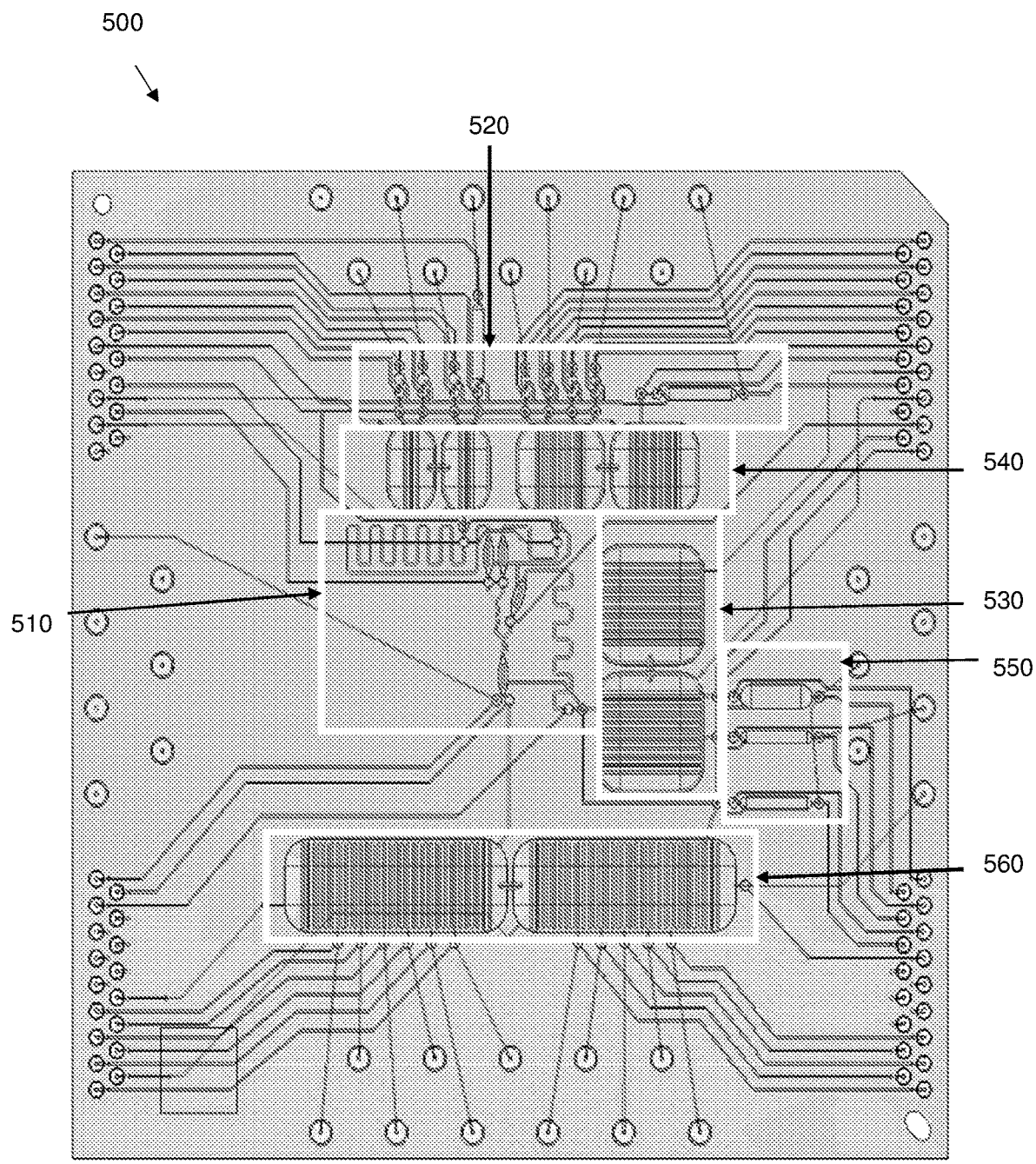
FIG. 5 is a schematic representation of an example apparatus including an example mixer and processing components according to some examples of the disclosure.

For example, FIG. 5 shows a microfluidic device configured as a microfluidic path formulation apparatus 500 including a cascading mixing sub-assembly 510 similar to that shown in FIG. 4. This mixing sub-assembly may include a plurality of vortex mixing chambers, which are configured in series. Apparatus 500 also includes pumps 520 and 550, and fluid driving chambers 530, 540, 560 (which may act as blending chambers).

Temperature

In any of the mixing apparatuses described herein Applicants have surprisingly found it to be beneficial for some materials, e.g., mRNA in aqueous solution and delivery vehicle (e.g., in ethanol) to mix at a temperature that is less than room temperature (e.g., less than about 25 degrees C.), such as, for example, 20 degrees C. or less, 18 degrees C. or less, 15 degrees C. or less, 12.5 degrees C. or less, 10 degrees C. or less, 8 degrees C. or less, 7 degrees C. or less, etc., e.g., between 20 and 5 degrees C., about 10 degrees C., etc.).

Any of the microfluidic path apparatuses described herein may be operated as part of a system that includes temperature control, including temperature control of the mixing portion (mixing sub-assembly) of a microfluidic device. Thus, the mixing sub-assembly, including one or more vortex mixing chambers, may be cooled to a temperature, e.g., between 20 degrees and 5 degrees C., such as between about 18 degrees and 5 degrees C., between about 15 degrees C. and 5 degrees C., between about 15 degrees C. and 8 degrees C., etc.) during operation of the mixing sub-assembly.

In some examples the entire microfluidic device including the mixing chamber may be regulated to the mixing temperature. Alternatively only a portion of the microfluidic device may be temperature controlled as described herein. For example, just the mixing chamber(s) may be temperature controlled to the mixing temperature, other portions of the microfluidic devices may be temperature controlled to one or more different temperatures. In some examples, the microfluidic device (or any sub-region thereof, such as the mixing chamber(s)) may be temperature controlled to the mixing temperature only while mixing; at other times they may be held at another temperature.

Figure 6:
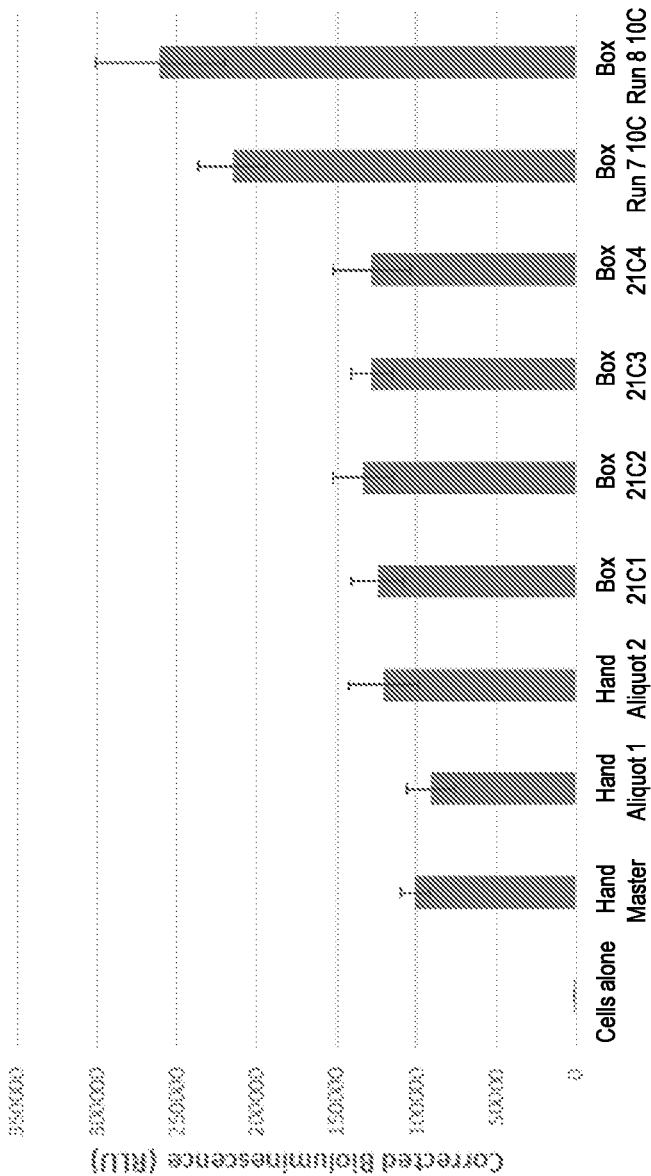
FIG. 6 is a graph illustrating, in one example, the effect of temperature (e.g., cooling) on mixing using a mixing apparatus as described herein.

FIG. 6 is a graph illustrating the effect of temperature on mixing using a mixing apparatus as described herein. In FIG. 6, mixing using a mixing apparatus similar to that shown above in FIGS. 1A-1B is shown (corresponding to the "8/28 Box" mixing), and compared against unmixed ("Cells alone") and hand mixed ("8/28 Hand") samples. Samples included cells that were transfected with a fluorescing agent, allowing quantification of the efficacy of mixing; a greater florescent signal indicates a higher degree of mixing efficiency, measured as corrected bioluminescence (RLU). Reagents mixed by hand ("8/28 Hand Master," "8/28 Hand Aliquot 1" and "8/28 Hand Aliquot 2") had a corrected bioluminescence that was approximately equivalent to those mixed at 21 degrees C. in a mixing apparatus as described above (e.g., "8/28 Box 21C 1," "8/28 Box 21C 2," "8/28 Box 21C 3" and "8/28 Box 21C 4"). Surprisingly, those mixed at lower temperatures, e.g., 10 degrees C., showed a much higher degrees of bioluminescence (compare with "8/28 Box Run 7 10C" and "8/28 Box Run 8 10C"). In FIG. 6, those mixed with the same mixing apparatus at lower temperature, e.g., 10 degrees C., had almost twice the bioluminescence as compared to the same mixing apparatus or by hand at 21 degrees C. For the combination of reagents shown, at higher temperatures (e.g., 40 degrees C. and 60 degrees C.), the bioluminescence, was approximately the same as at 21 degrees C.

The mixing temperature may be manually or automatically set. In some examples, the mixing temperature, which is typically but not exclusively between about 20 degrees and about 5 degrees C., may be determined based on the mRNA (e.g., the therapeutic mRNA) and/or delivery vehicle that is being mixed. For example, the combination of mRNA and delivery vehicle may be used to determine the enhanced mixing temperature, as described above. The enhanced mixing temperature may be determined empirically (e.g., experimentally) and/or by calculating, e.g., based on the size, molecular weight, sequence, etc. of the mRNA and/or delivery vehicle.

As described above, the mixing apparatuses described herein may be part of a microfluidic apparatus (e.g., a microfluidic device), and may include a first fluidic input and a second fluidic input, a fluidic intersection channel configured to receive fluid from the first fluidic input and the second fluidic input, in which the fluidic intersection channel opens into a first mixing chamber on an upper region of a first side of the first mixing chamber. The first mixing chamber may have a depth that is greater than about 1.5 times a depth of the fluidic intersection channel. The device may also include an outlet channel on an upper region of a second side of the first mixing chamber, wherein the outlet channel has a depth that is less than the depth of the first mixing chamber, further wherein an opening of the outlet channel is offset along a width of the second side of the first mixing chamber relative to the fluidic intersection.

In some examples, multiple mixers (e.g., multiple mixing chambers) may be included as part of the microfluidic mixing apparatus and may be connected in series. For example, FIGS. 7A-7D illustrate examples of mixing apparatuses having one (FIG. 7A), three (FIG. 7B), six (FIG. 7C) and twelve (FIG. 7D) mixing chambers. As described above, surprisingly, nearly uniform mixing may be achieved with a single mixing chamber (see, e.g., FIGS. 2A-2E). In some cases, particularly where the mixture includes particles that are suspended in the fluid being mixed, more than one, e.g., two or three, mixing chambers may be used to achieve complete or nearly complete mixing. This is illustrated below, and is particularly surprising, given the relatively small dimensions (e.g., footprint) for the mixing apparatus, even when relatively high flow rates and low pressures are used (e.g., pressures of between about 6.9 kPa to about 206.8 kPa and flow rates of between 1 ml/min and about 10 ml/min). The mixing apparatuses described herein may have a total length of about 2 mm or less (e.g., about 1.75 mm or less, about 1.7 mm or less, about 1.6 mm or less, about 1.5 mm or less, about 1.4 mm or less, about 1.2 mm or less, about 1 mm or less, about 0.8 mm or less, about 0.7 mm or less, etc.) from input to output. Even these relatively short lengths may achieve mixing that is nearly uniform.

All of the apparatuses and methods described herein provide mixing that is superior to that of hand mixing, including providing more uniformity as well as smaller resulting particle sizes in mixtures including particles (which may otherwise cluster). However, mixtures having particles may present particular challenges for microfluidic mixing. For example, repeated and/or continuous use of a microfluidic mixer may result in deposition of particles within the channels of the microfluidic mixing apparatus. FIG. 8 illustrates this potential issue. In FIG. 8, an image of a mixing apparatus is shown. The mixing apparatus include three serially connecting mixers (mixing chambers) as described herein, e.g., having a width/depth/length of about 250/200/500 μm. In this illustration the mixing apparatus was used for continuous operation, mixing fluids including material (e.g., mRNA and molecules of delivery vehicle with or without mRNA, such as molecules of an amino-lipidated peptoid delivery vehicle) to form therapeutics (e.g., mRNA encapsulated in delivery vehicle), but resulted in deposition of material 807 within the mixing apparatus over time. In operation, such deposition may lead to clogging. The apparatuses and method described herein may be configured to reduce or prevent clogging and/or deposition of material.

For example, in some examples the number of mixing chambers may be limited. Thus in some cases 3 or fewer mixing chambers may be used. As mentioned and illustrated above, in some examples two mixing chambers may be serially coupled for mixing in a mixing apparatus. In some example, three mixing chambers may be serially coupled for mixing in the mixing apparatus. Alternatively, in some examples only a single mixing chamber may be included. These configurations may have the added benefit of having a substantially smaller footprint as compared to other mixers.

In some examples, the size of the chambers and/or channels of the mixing apparatus may be proportionally increased. Larger mixing chambers may reduce the deposition of particles within the channels. For example, in some examples, the dimensions of the mixing chamber(s) may have a width of between about 225 and about 600 μm (e.g., between about 250-about 600 μm, between about 300-about 550 μm, etc.), a depth of between about 175 and about 425 μm (e.g., between about 200-about 400 μm, between about 300-about 425 μm, etc.), and a length of between about 450-about 1050 μm (e.g., between about 500 μm—about 1000 μm, etc.). For example, the mixing chamber(s) may have a width/depth/length of about 500/400/1000 μm. Similarly, the connecting channel(s) may have a width of between about 75 μm—about 225 μm (e.g., between about 100 μm—about 200 μm, etc.), a depth of between about 75 μm—about 225 μm (e.g., between about 100 μm—about 200 μm, etc.), and a length of between about 225 μm—about 525 μm (e.g., between about 250 μm—about 500 μm, etc.).

FIGS. 9A and 9B illustrate examples of mixing apparatuses that are similar but scaled relative to each other. The mixing apparatus of FIG. 9A shows mixing chambers 905 and connecting channels 903 that are of a first set of dimensions (e.g., the mixing chamber width/depth/length is about 250/200/500 μm, and the connecting channel width/depth/length is about 100/100/250 μm). In FIG. 9B the same shape has been scaled up by a factor of 2 (e.g., 2 times), so that the mixing chamber and connecting channels have twice the width, depth and length (e.g., mixing chamber having a width/depth/length of about 500/400/1000 μm, and connecting channels having width/depth/length of about 200/200/500 μm).

As shown in FIG. 9C, the overall mixing efficacy of the mixing apparatus in both the smaller (e.g., FIG. 9A) and larger (e.g., FIG. 9B) dimensions were comparable; both the average particle size as well as the dispersity of the particles was examined for both. Dispersity is a measure of the heterogeneity of sizes of molecules or particles in a mixture. A collection of objects is called uniform if the objects have the same size, shape, or mass. A sample of objects that have an inconsistent size, shape and mass distribution is called non-uniform. Polydispersity index (PDI) is used as a measure of broadness of molecular weight distribution, therefore an indicator of the size distribution. The larger the PDI, the broader the molecular weight distribution. PDI of a polymer is calculated as the ratio of weight average by number average molecular weight. Dispersity (e.g., PDI) can be measured by light scattering measurements such as dynamic light scattering, and/or direct measurement, e.g., via mass spectrometry, using matrix-assisted laser desorption/ionization (MALDI) or electrospray ionization with tandem mass spectrometry (ESI-MS). The Polydispersity Index is dimensionless and scaled such that values smaller than 0.05 are rarely seen other than with highly monodisperse standards. Values greater than 0.7 may indicate that the sample has a very broad size distribution, and thus not uniform in size. The Z-Average size or Z-Average mean may be used in dynamic light scattering as a parameter (also known as the cumulants mean) to provide a hydrodynamic parameter that is applicable to particles in a dispersion or molecules in solution.

As shown in FIG. 9C, the PDI for both the smaller (FIG. 9A) and larger (FIG. 9B) mixing apparatuses were reasonably similar; however, the Z-average was somewhat smaller in the smaller mixer apparatus as compared to the larger mixing apparatus.

Figure 10A:
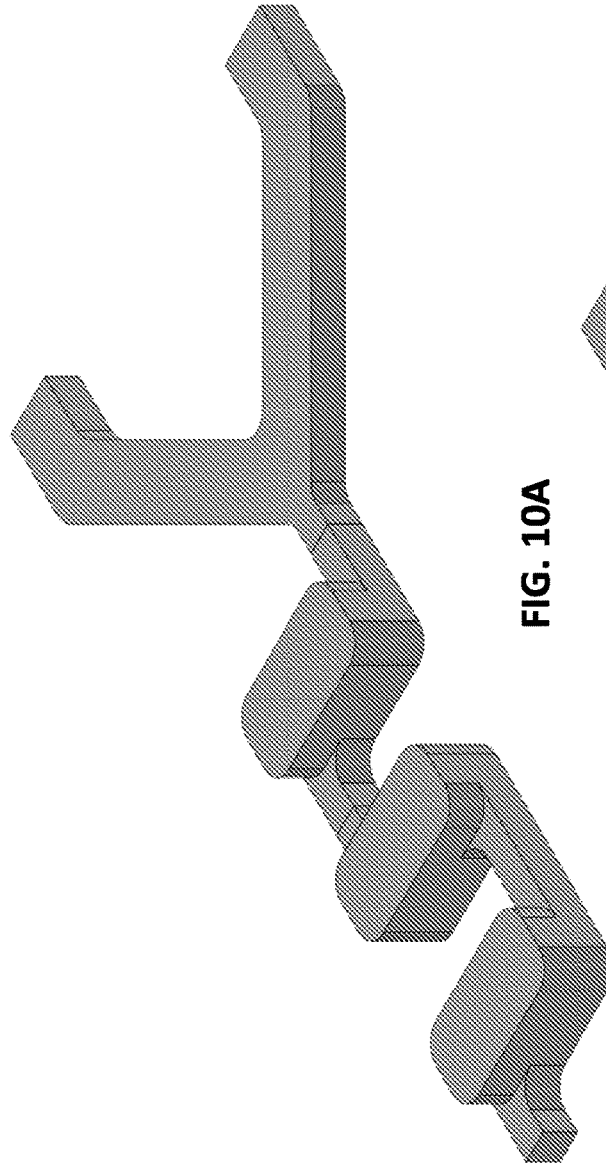
FIG. 10A shows a mixing apparatus including three mixers connected in series, as described herein.
Figure 10B:
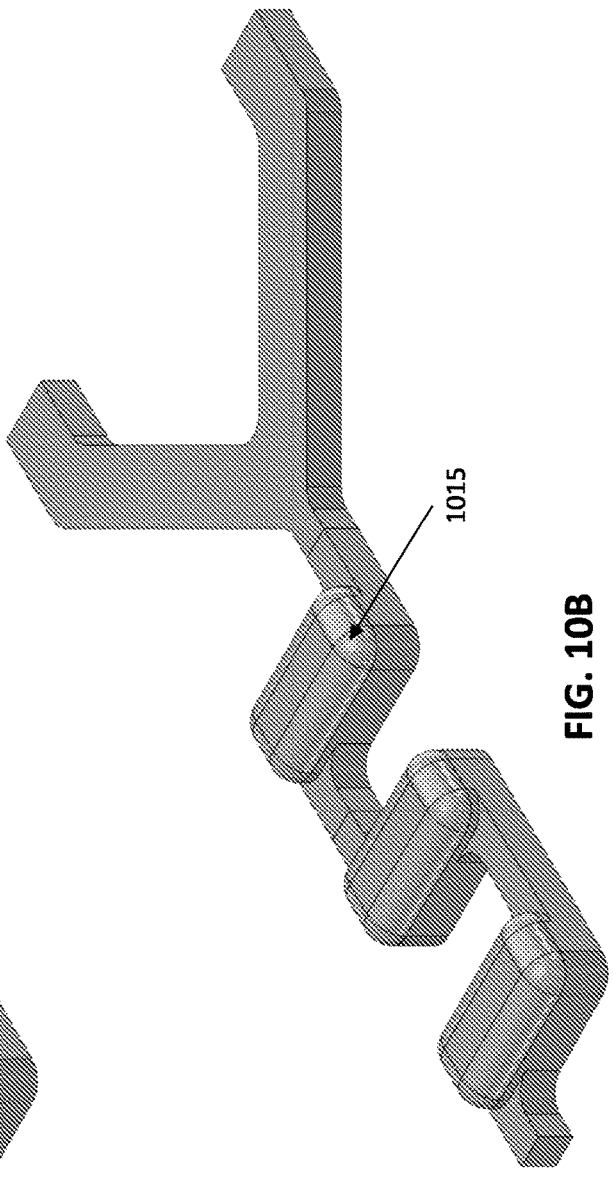
FIG. 10B shows a similar mixing apparatus to that shown in FIG. 10A, but with the corner regions rounded, which may reduce, and in some instances even eliminate, dead regions (regions of little fluid flow) within the mixer.

Any of the mixing apparatuses described herein may have rounded or curved corners and/or edges. For example, FIG. 10A shows a mixing apparatus similar to that shown above (e.g., FIG. 7B, 9A, etc.) and FIG. 10B shows an example of a mixing apparatus having rounded edges 1015 and/or corners on the bottom and/or top of the mixing apparatus. Rounded (e.g., radiused, curved, etc.) edges/corners may prevent dead regions or regions of stagnation in the mixer where particles may deposit. Further, the rounded edges may also amplify the mixing within the mixing chamber, as described above (as the fluid may be driven against the wall to rotate within the chamber, enhancing mixing). In some examples the openings into the exits from the mixing chambers (e.g., into the connecting channels) may include a ramp or funnel shape, in which diameter of the opening (or the width and depth) may be ramped, funnel-shaped, etc. to provide a more gradual transition between the mixing chamber and the channel(s).

Figure 11B:
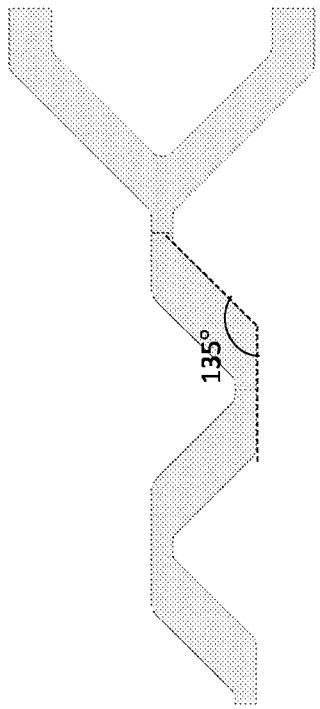
FIGS. 11A and 11B illustrate an example of a mixing apparatus having three mixers connected in series at an angle that is greater than 90 degrees, but less than 180 degrees.
Figure 11A:
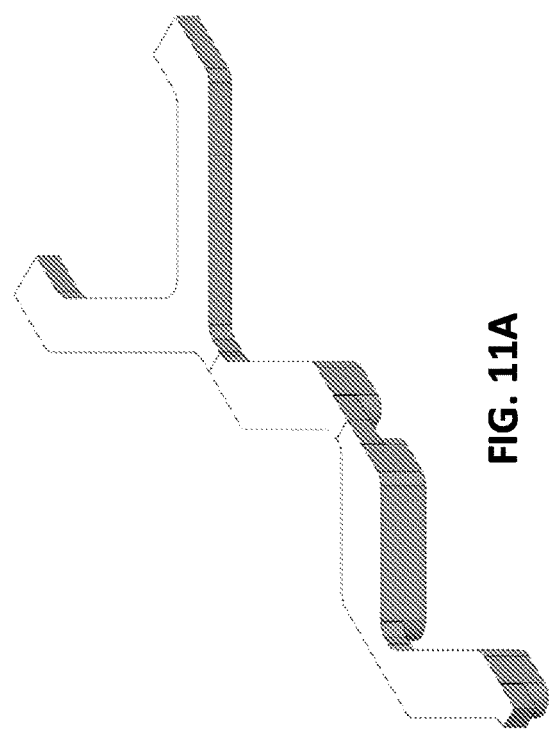

Any of the apparatuses described herein may be configured so that the mixers are at an angle relative to each other, as described above. In some examples the angle is approximately 90 degrees (as shown in FIGS. 7B-7D), in which the mixing chambers are arranged perpendicular to the connecting channel. FIGS. 11A-11B illustrate another example of a mixing apparatus in which the angle between the mixing chamber and the connecting channel is about 135 degrees (see FIG. 11B), when observed from the top. Thus in some examples the angle between the mixing chamber and the connecting channel (which may be referred to as a box angle or mixing chamber angle) may be between 90 degrees and 180 degrees, such as about 100 degrees, about 110 degrees, about 120 degrees, about 130 degrees, about 135 degrees, about 140 degrees, about 150 degrees, about 160 degrees, etc.). Increasing this angle above 90 degrees may reduce deposition and/or may increase the flow rate (for a lower pressure). Conversely, in some cases it may be preferable to decrease the angle to less than 90 degrees, which may increase mixing efficiency.

Figure 11C:
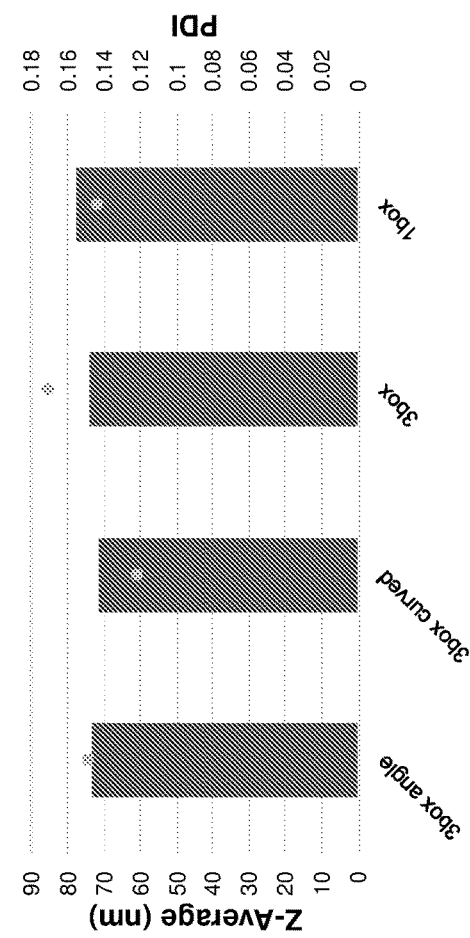
FIG. 11C is a graph illustrating the mixing effects of different configurations of mixing apparatuses, including a mixing apparatus having a 135 degree angle ("3 box angle," as shown in FIGS. 11A-11B) and a curved mixing apparatus ("3 box curved," as shown in FIGS. 10A-10B), compared to a mixing apparatus such as shown in FIG. 7B having three mixers connected in series ("3 box"), or a mixing apparatus such as shown in FIG. 7A having a single mixer ("1 box").

As shown in FIG. 11C, there was not a significant change in the Z-Average (e.g., particle size) or PDI between angled and curved (e.g., 135 degrees vs. 90-degree angles). As shown in FIG. 11C, in general, a one-stage mixer (e.g., a mixer having only a single mixing chamber) may sufficiently mix, even with particles. As compared with three-stage devices that are otherwise similar in dimension, the final particle sizes and PDI values were found to be comparable, or in some instances even better, for the one-stage mixer. Thus, the highly compact one-stage apparatus may be used and may result in much less flow restriction.

In some examples, the mixing apparatuses described herein may result in substantially less deposition over time. For example, apparatuses in which the sidewalls and/or bottom and/or top are curved may result in less than 25% deposition per time and/or rate of flow (e.g., less than 20%, less than 15%, less than 10%, less than 5%, etc.).

Figure 13:
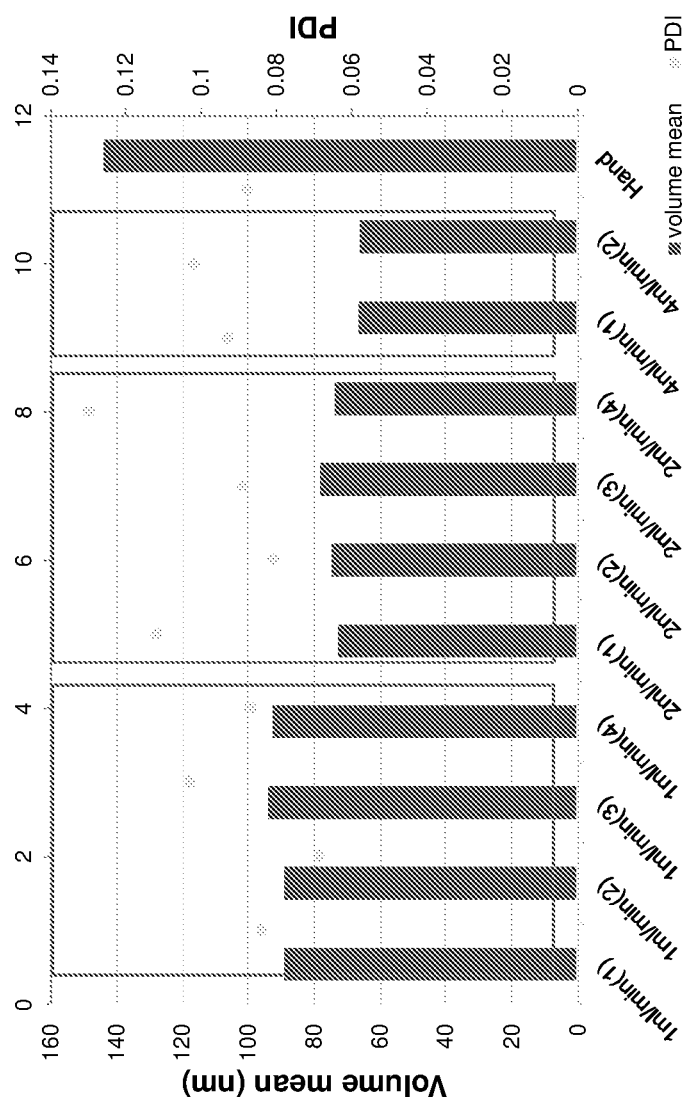
FIG. 13 is a graph illustrating the effects of flow rate through a mixing apparatus having three mixers ("3 box" mixer) similar to that shown in FIGS. 7B, 9A, and 10A, showing that higher flow rates have resulted in smaller particle sizes, and visibly better mixing as compared with hand mixing.

As mentioned, the flow rate may be controlled. The flow rate may also impact the mixing. In general, faster flow rates through these apparatuses may result in smaller particle sizes, which may reflect the enhanced mixing. This is illustrated in FIG. 13. In FIG. 13, multiple examples of similar microfluidic mixing apparatuses were examined on the same microfluidic device substrate (e.g., "chip"), providing parallel repeats of 1 ml/min (1-4), 2 ml/min (1-4) and 4 ml/min (1-2). Flow rates may be tuned to the particle size and/or the dimensions of the microfluidic device. In FIG. 13, both volume mean (size in nm) and PDI were reasonably comparable, and showed that as flow rate increased, the particle sizes decreased.

Figure 12B:
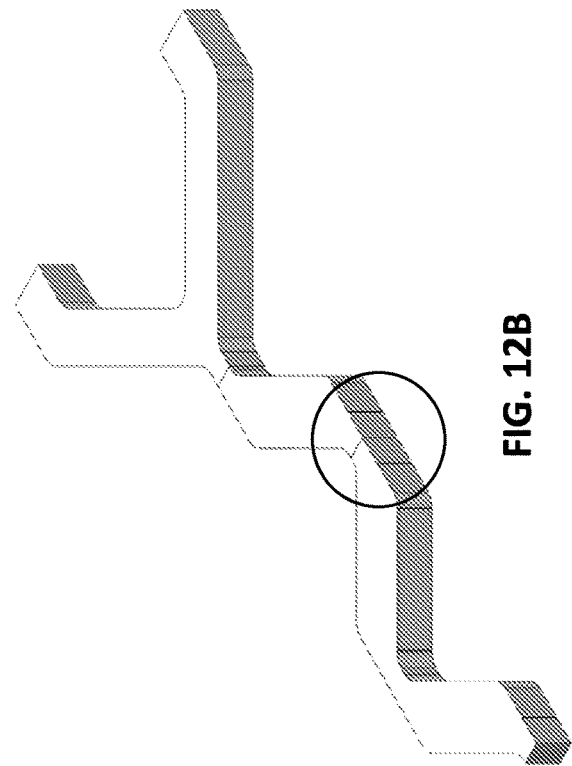
FIG. 12B shows an example of an apparatus that does not include the step from a narrower height channel into the deeper box of the mixer.
Figure 12A:
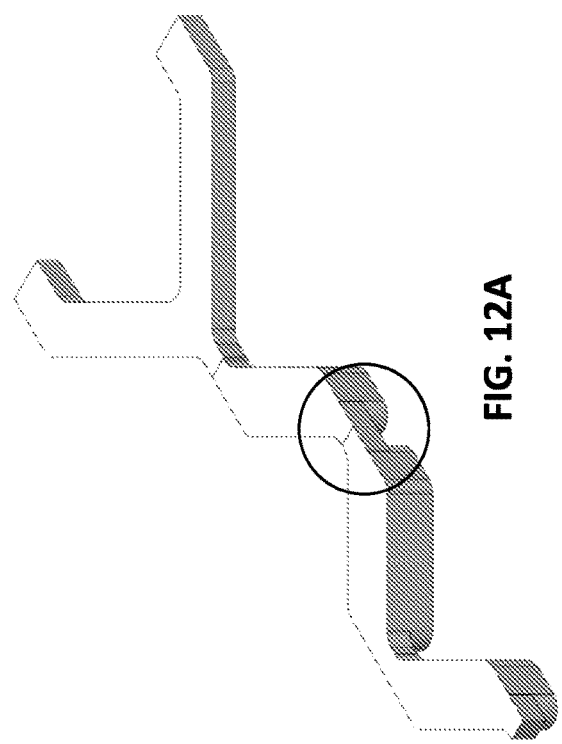
FIG. 12A shows another example of a mixing apparatus including three mixers connected in series, as described herein.
Figure 12C:
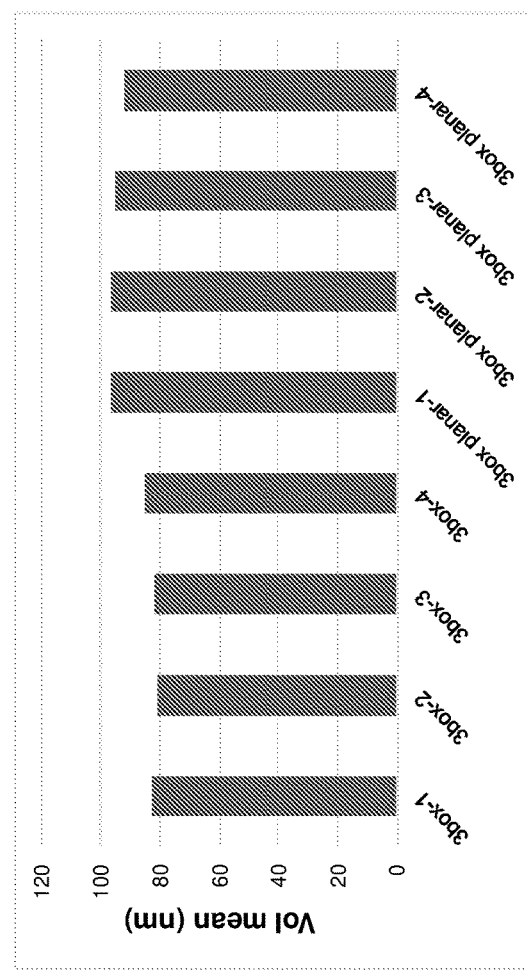
FIG. 12C is a graph showing the particle size (due to mixing) following multiple runs through a mixing apparatus as shown in FIG. 12A ("3 box") or through a linear mixing channel as shown in FIG. 12B ("3 box planar"), showing visibly smaller particle sizes (and therefore more efficient mixing) in the mixing apparatus of FIG. 12A as compared to FIG. 12B.

As discussed above, the 'step' or transition from the smaller opening in the input of the mixing chamber to the mixing chamber and the return to the small diameter in the output (or connection) channel(s) may enhance the mixing. However, in some examples, as shown in FIG. 12B, the mixing apparatus may have a same height between the input, output and mixing chamber. FIG. 12A shows another example of a mixing apparatus including three mixers connected in series, similar to FIG. 7B. For comparison, FIG. 12B shows an example of an apparatus that does not include the step from a narrower height channel into the deeper box of the mixer. In general, these mixers may not result in the high level of mixing shown for other examples, as shown in FIG. 12C. FIG. 12C is a graph showing the particle size (due to mixing) following multiple runs through a mixing apparatus as shown in FIG. 12A ("3 box") or through a linear mixing channel as shown in FIG. 12B ("3 box planar"), showing substantially smaller particle sizes (and therefore more efficient mixing) in the mixing apparatus of FIG. 12A as compared to FIG. 12B.

Optional Examples

Also described herein are additional examples of microfluidics apparatuses. These apparatuses may include a mixer as described herein with one or more additional and optional microfluidic components. For example, the outlet channel of a mixer may be in fluid communication with one or more of: a pair of final blending chambers, a dialysis chamber or an evaporation chamber. A microfluidic path device (e.g., microfluidic chip) may include a microfluidic dialysis chamber and/or microfluidic concentrator. A dialysis chamber and/or concentrator may be extremely compact and efficient and may operate on or within the bounds of a microfluidic apparatus with high efficiency and accuracy. The mixing methods and apparatuses described herein may allow a microfluidic apparatus to also provide, in a single integrated apparatus, purification, dialysis and concentration of one or more therapeutic composition (including, but not limited to therapeutic polynucleotides).

For example a microfluidic path device may include: a first plate and a second plate; a fluid-contacting chamber having a fixed volume formed in the first plate; a dialysis buffer chamber having a fixed volume formed in the second plate; wherein the fluid-contacting chamber is separated from the dialysis buffer chamber by a dialysis membrane disposed between the first plate and the second plate; and a plurality of pressure ports through the first plate; and wherein the fluid-contacting chamber comprises a plurality of channels partitioning the fluid-contacting chamber.

A microfluidic dialysis chambers may have a fluid-contacting chamber formed in the first plate, a dialysis buffer chamber formed in the second plate, wherein the fluid-contacting chamber is separated from the dialysis buffer chamber by a dialysis membrane disposed between the first plate and the second plate, and a plurality of pressure ports through the first plate; and wherein the fluid-contacting chamber comprises a plurality of channels partitioning the fluid-contacting chamber.

Any of these microfluidic dialysis chamber devices may include an inlet into the fluid-contacting chamber and an outlet from the fluid-contacting chamber, wherein the inlet is located on an opposite side of the length and an opposite side of the width of the fluid contacting chamber. The inlet may be offset from a side of the fluid-contacting chamber by between about 15% and about 35% of the width of the fluid-contacting chamber. Any of these dialysis apparatuses may include an elastic membrane sandwiched between the first and second plates. The periphery of the dialysis membrane may be sealed by an elastic membrane.

For example, a microfluidic path device may include: a first plate and a second plate; a fluid-contacting chamber having a fixed volume formed in the first plate; a concentration chamber having a fixed volume formed in the second plate; wherein the fluid-contacting chamber is separated from the concentration chamber by a hydrophobic membrane disposed between the first plate and the second plate; and a plurality of pressure ports through the first plate; and a plurality of separately-addressable membrane-driven pumps controlled by the pressure ports and configured to drive fluid through the fluid contacting chamber and dry air through the concentration chamber.

A microfluidics path device may include: a mixer; a dialysis sub-assembly; and a concentrator sub-assembly; wherein the mixer dialysis sub-assembly and concentrator are formed between a first plate and a second plate.

A dialyzer may be formed as part of a microfluidics path device and may include a first chamber separated from a second chamber by a dialysis membrane; the first and/or second chamber may be divided up into channels. The first channel is configured to pass the fluid to be dialyzed and the second channel is configured to pass a dialyzing solution. The dialyzing solution may be passed through the second channel in a countercurrent direction (e.g., opposite the direction of fluid flowing through the first channel.

In some examples the dialyzer is formed between a first plate and second plate (e.g. a first layer and a second layer) of a microfluidics path device. The first channel may be formed in the first plate and the second channel may be formed in the second plate; the dialysis membrane may be sealed between the first and second plates. In some examples an elastic membrane may be sandwiched between the first plate and the second plate; the dialysis membrane may be sandwiched between the first plate and the second plate across an opening in the elastic membrane and may be sealed (e.g., around its perimeter) by the elastic membrane. The first chamber of the dialyzer may include an inlet on one end and an outlet on an opposite end of the first chamber. The inlet and outlet may be offset from the side edges of the first chamber, e.g., at a location between 15-45% of the width of the chamber from the first side edge, where the width is formed between the side edges. Similarly the outlet may be on an opposite side of the chamber (separated by most of the length of the chamber, and offset from the second side (opposite to the first side edge) by an amount that is the same or approximately the same as the inlet is from the first side edge (e.g., between 15-45% of the width of the chamber).

Alternatively, in some examples the elastic membrane is not used to seal the dialysis membrane. Thus, the dialysis membrane may be held securely by the engagement of the first plate with the second plate. In some examples an additional (e.g., third plate) and/or elastic membrane may be included, e.g., beneath or above the putative first and second plates.

The first and/or second chambers of the dialyzer may be divided up into a plurality of channels, as mentioned above. In some examples the channels may be parallel and may extend in straight lines. In some examples the channels extend in curved or zig-zag lines. The channels may be a uniform cross-sectional diameter, or they may be different diameters and/or may have the same cross-sectional diameters.

FIG. 14A shows a perspective view of an example of a dialyzer as described herein. In FIG. 14A, the dialyzer is a sub-region (or dialyzer module) of a microfluidics device including a first plate 1401, a second plate 1403 and an elastic membrane 1405 sandwiched between the first and second plate. An opening through the elastic membrane (not visible) may be spanned by a dialysis membrane 1407. The first chamber is separated from the second chamber of the dialyzer by the dialysis membrane 1407, and each chamber shown is divided up into a plurality of parallel channels extending the length of the first and second chambers.

FIG. 14B is an example of a cross-section through a dialyzer similar to that shown in FIG. 14A. In FIG. 14B, the dialyzer includes a first chamber 1411, a second chamber 1413 and a dialysis membrane 1407 between the first and second chambers. An inlet 1422 into the second chamber is also shown as is an outlet 1423 from the first chamber (the second chamber outlet and first chamber inlet are not visible in FIG. 14B). The channels in each chamber may be formed by the plates from which the chambers are formed. In some examples the channels are on just one side (e.g., the first chamber side); in some examples the channels are on both sides and may be opposite from each other or may be offset from each other.

FIG. 15 is an example of an edge region of a dialyzer such as the example shown in FIGS. 14A-14B, showing the seal between the upper and lower chambers and the dialysis membrane. In FIG. 15, a first plate 1501 includes a first chamber 1511. The first chamber is divided up into connected channels. A second plate 1503 is affixed to the bottom of the first plate and includes a second chamber 1505 that is also divided into channels. Channel dividers 1509, 1519 in the first and/or second plate form contact points that crimp a dialysis membrane 1515 therebetween.

At the edge of the dialyzer 1500 an elastic membrane 1521 may be sandwiched between the first and second plates. An edge of the elastic membrane (e.g., a silicone membrane, etc.) may be also secure (e.g., seal) the dialyzer membrane between the first and second plates, as shown in FIG. 15.

Figure 16:
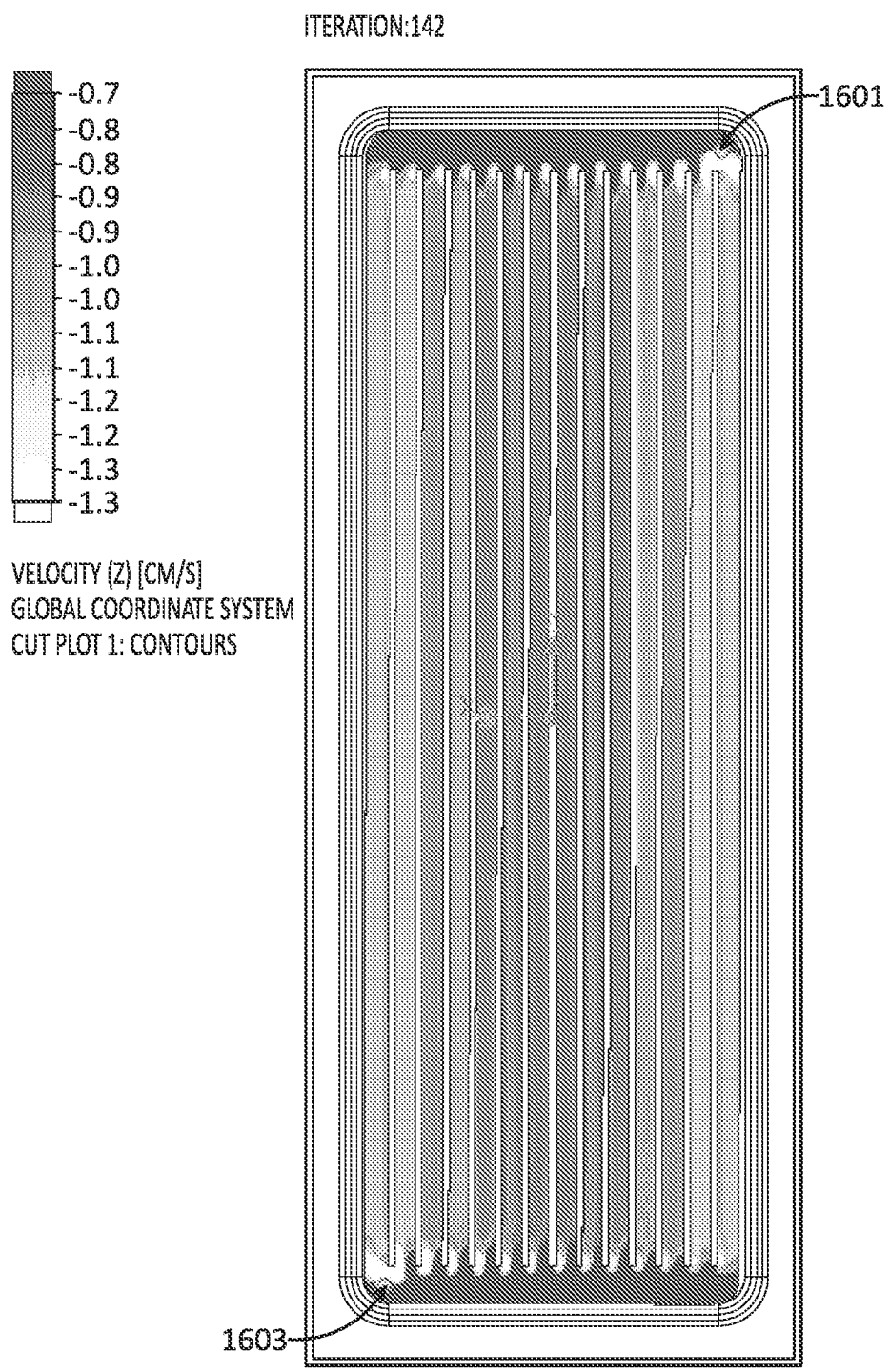
FIG. 16 illustrates one example of a dialyzer as described herein, showing exemplary flow rate (velocity) through the device.

In operation, a dialyzer portion of a microfluidics path device may include an inlet on the sample processing side of the device for driving (by applying pressure) a solution to be dialyzed into the first chamber of the dialyzer. In FIG. 16 the first chamber is shown, divided by a plurality of parallel channels. The inlet 1601 in this example is positioned in the top, common region of the channel, from which fluid to be dialyzed may flow towards the outlet 1603. In this example, the inlet and outlet are on opposite sides of the width and on opposite sides of the length of the chamber. The shading indicate the flow rate (velocity, Z, in cm/s) through the chamber, from the inlet to the outlet. With this arrangement of inlet and outlet the flow rate is non-uniform, as evidenced by the shading map, showing slower flow through the more peripheral channel regions.

FIG. 17A shows an example in which the inlet 1701 and outlet 1703 are positioned slightly inwardly from the long sides of the chamber (e.g., between 15% and 35% of the width of the chamber, e.g., approximately one-quarter of the way into the width) in the common regions at the ends of the chamber, on opposite sides of the width and length. The resulting flow (shown by heat map key FIG. 17B) rates are significantly more uniform, with slightly faster regions in the channels closest to the inlet and outlet. In the example of FIG. 17A-17C, the maximum flow rate may be, e.g., about −1.1 cm/sec, while the minimum flow rate may be, e.g., about −0.9 cm/sec. FIG. 17C show the upper common region 1707 that feeds into the channels extending the length of the first chamber of the dialyzer; this region may have local regions of higher flow rate 1711, 1709. In this example, the pressure between the inlet and outlet may drop between, e.g., about 14.92 psi (102.87 kPa) and 14.70 psi (101.35 kPa), delta of 0.22 psi (1.52 kPa), when the flow is 0.5 ml/min.

In use, the dialyzer may be used to dialyze a solution containing a therapeutic material, e.g., to remove an unwanted material from the solution. As the solution is flowed through the first chamber, the dialysis solution may be flowed in the same or counter direction as the second chamber opposite from the first chamber. The second chamber may have essentially the same structure as the first chamber described above.

Also described herein are concentrators. A concentrator may have the same structure as the dialyzer described above, however the membrane may be a membrane that permits water vapor to pass (allowing evaporation therethrough) so that air can be flowed across, (hydrophobic membrane) within the second chamber, as fluid is passed through the first chamber, thereby evaporating and concentrating the solution.

Figure 18:
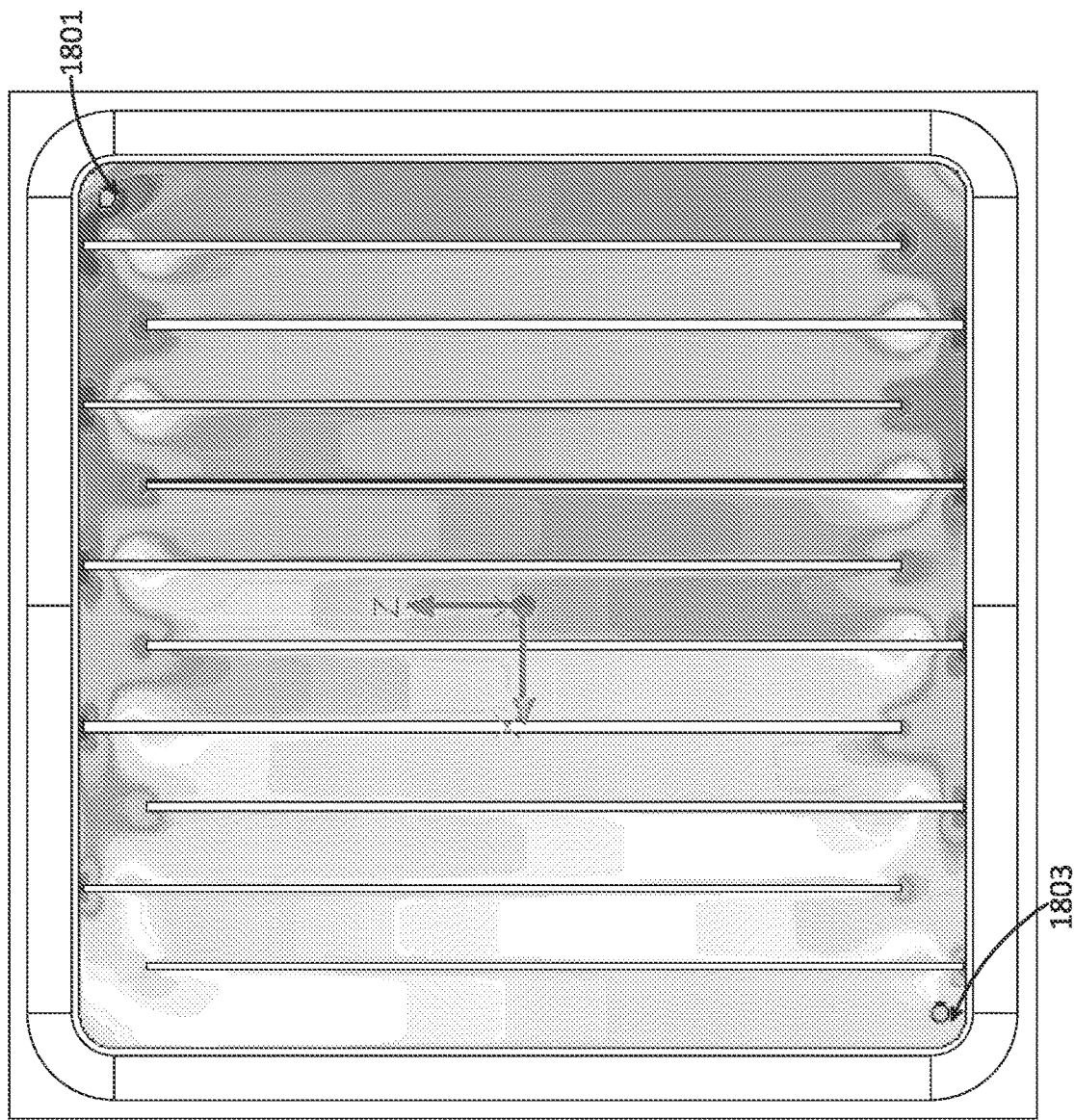
FIG. 18 is an example of a concentrator as described herein.

In some examples the concentrator is configured to have one or more pathways (channels) through the first, fluid-passing chamber and in some cases, the second chamber through which gas (e.g., air) is passed. FIG. 18 illustrates one example of a concentrator apparatus (e.g., a concentrator sub-assembly for a microfluidics path device). In FIG. 18, the concentrator includes an elongate channel from the inlet 1801 to the outlet 1803 in the first chamber. A membrane (not shown in FIG. 18) that allows water vapor to pass extends between the first chamber and a second chamber. Gas may be passed through the second chamber to remove water and therefore concentrating the solution as it passes through the first chamber. The rate of evaporation may be related to the flow rate through the concentrator. In FIG. 18, the shading mapping shows the velocity (cm/s) through the first chamber of the concentrator.

In use, the concentrator may be highly efficient and may concentrate a manufactured dose of therapeutic agent from the microfluidics path device into a concentration range that allows dilution to an injectable dose form (e.g., between 2 mL and 0.1 mL).

The example concentrator shown in FIG. 18 is a 25.4 mm by 25.4 mm square. The membrane is a Sterlite PTFE Membrane, 0.22 μm pore size, 37 μm thick. In FIG. 18, the input flow rate is approximately 0.5 ml/min. The dialysis membrane transport rate is 0.483 ml/min, and the resulting output flow rate is approximately 0.019 ml/min, 1.1 ml/hr. In this example, for a velocity between about 4.321 cm/s and 0.160 cm/s, the pressure drop between the inlet and the outlet may be, e.g., 14.96 psi (103.15 kPa) at the inlet and 14.70 psi (101.35 kPa) at the outlet (delta of 1.8 kPa).

Figure 19:
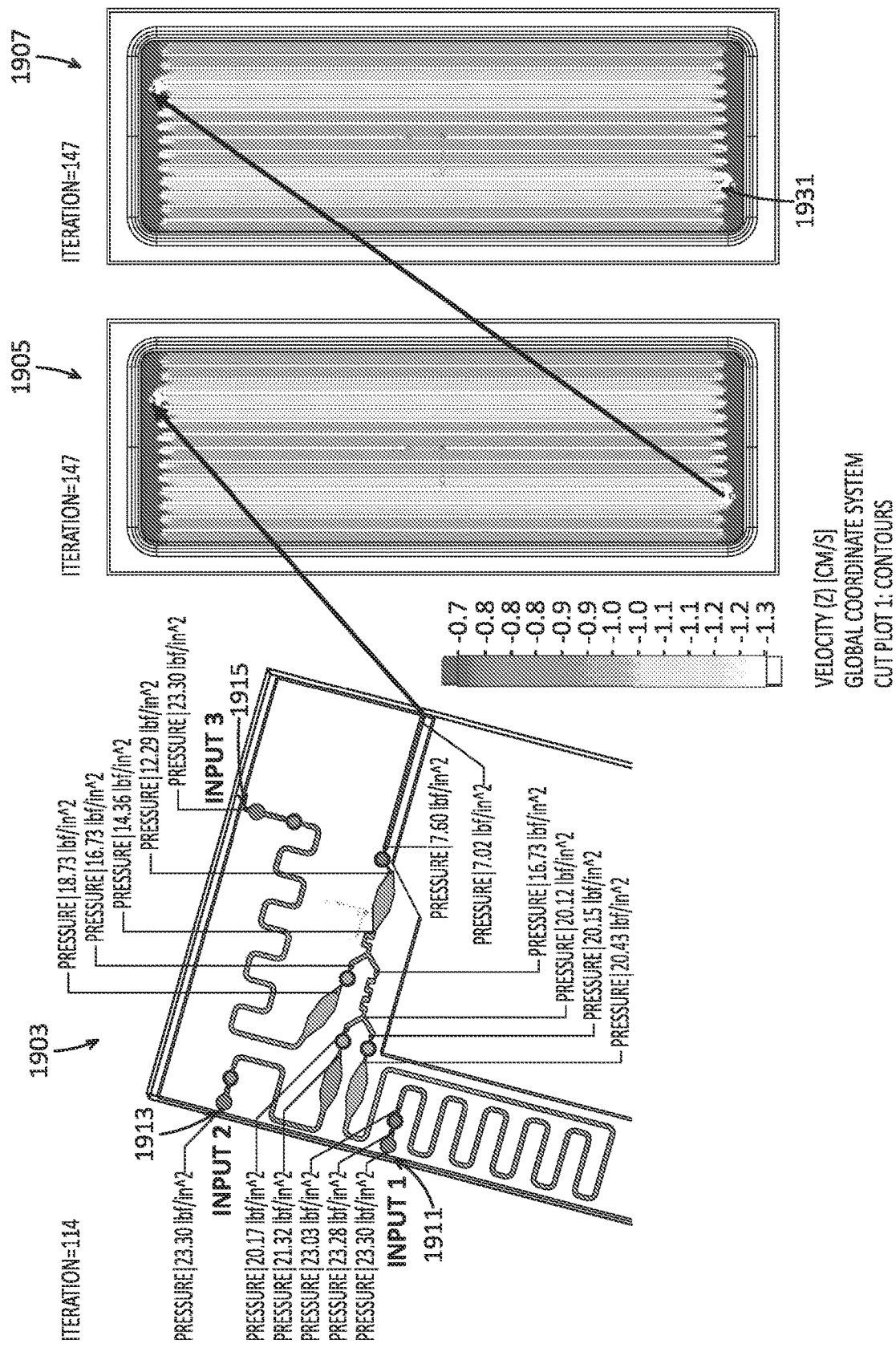
FIG. 19 schematically illustrates an example of a microfluidics path device as described herein, including both mixing (using one or more vortex mixing chambers), dialysis, and concentration.

As described above, any of the microfluidic path devices described herein may include one or more dialyzers and/or one or more concentrators (dialyzer sub-assembly and/or concentrator sub-assembly). FIG. 19 schematically illustrates a microfluidics path device that include both a series of mixers 1903, e.g., for compounding a therapeutic (e.g., a therapeutic RNA) formed on the microfluidic path device or added to the microfluidic path device, including for adding a delivery vehicle, and a dialyzer 1905 in series between the mixer(s) and a concentrator 1907. A first input 1911, a second input 1913 and a third input 1915 may be inserted as described above in reference to FIG. 4. The final product, following compounding/mixing, dialysis and concentration, may be output from the concentrator 1931 and may be used or stored, or further processed. In this fashion the creation of nanoparticle therapeutics, including dialysis and concentration to a final injectable form may be done using a single, continuous flow microfluidic device with no intermediate storage of materials created in the formulation process.

Figure 20:
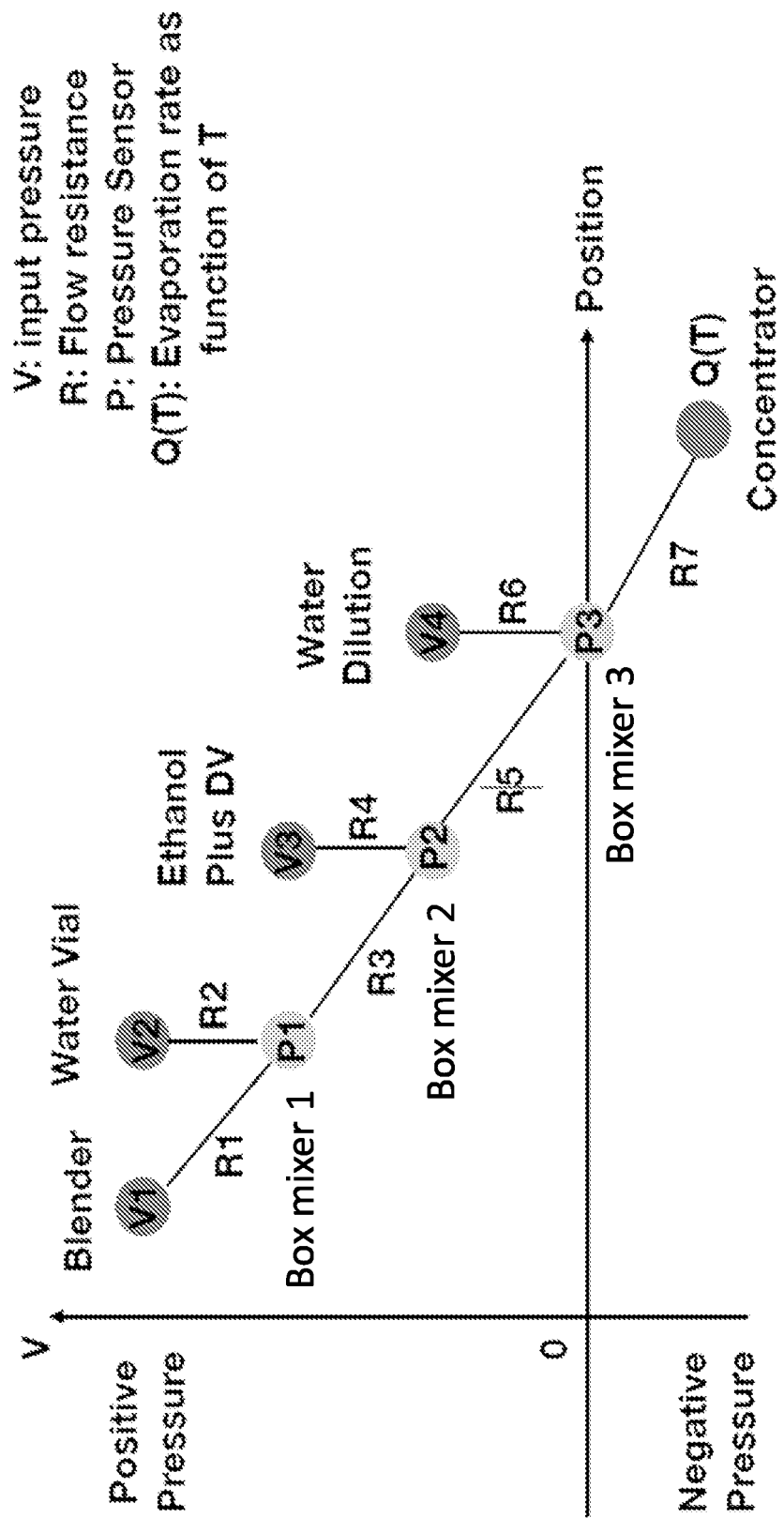
FIG. 20 is a schematic representation of pressure characteristics of a microfluidic apparatus including microfluidic mixers (e.g., box mixers), formulating components, and a concentrator according to some embodiments of the disclosure.

FIG. 20 illustrates one example of the relationship between pressure and position on an exemplary microfluidics path device such as the device shown schematically in FIG. 19. In FIG. 20, the input pressures (V1-V4) flow resistances and pressures may be adjusted and/or monitored by the system to control the final concentration by regulating the concentrator.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be cojointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. In all cases, where the phrase "about" or "approximately" is used, the actual value (e.g., amount, distance, etc.) may be used. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A method of formulating a therapeutic mRNA with a delivery vehicle, the method comprising mixing the therapeutic mRNA and the delivery vehicle in a microfluidic mixing chamber of a microfluidic device at a temperature that is between about 2 and about 20 degrees C., wherein the temperature is selected using at least a composition of the therapeutic mRNA, a composition of the delivery vehicle, or a combination thereof.

2. The method of claim 1, further comprising selecting the temperature using at least: a polynucleotide sequence of the therapeutic mRNA, a sequence of the delivery vehicle, a molecular weight of the delivery vehicle, a molecular weight of the therapeutic mRNA, a charge of the delivery vehicle, a charge of the therapeutic mRNA, a molecular weight of the delivery vehicle, a molecular weight of the therapeutic mRNA, a flow rate of the therapeutic mRNA and/or the delivery vehicle within the microfluidic mixing chamber, and a dimension of the microfluidic mixing chamber, or any combination thereof.

3. The method of claim 1, wherein mixing comprises mixing in a microfluidic device comprising the microfluidic mixing chamber.

4. The method of claim 1, further comprising separately maintaining the temperature of the mixing chamber to be between about 2 and about 20 degrees C., relative to the rest of the microfluidic device.

5. The method of claim 1, wherein mixing in the microfluidic mixing chamber comprises passing the therapeutic mRNA and the delivery vehicle through a first opening into the mixing chamber of a microfluidic device so that the therapeutic mRNA and the delivery vehicle are driven against a wall of the mixing chamber and driven out of a plane of the first opening to a depth of greater than one times the depth of the first opening.

6. The method of claim 5, wherein passing comprises driving the therapeutic mRNA and the delivery vehicle against the wall of the mixing chamber and out of a plane transverse to the first opening to the depth of greater than about 2.5 times the depth of the first opening.

7. The method of claim 5, wherein the therapeutic mRNA and the delivery vehicle are driven against the wall of the mixing chamber and out of a plane transverse to the first opening to a depth of 3 or more times the depth of the first opening.

8. The method of claim 5, wherein a top of the first opening is in line with a top of the mixing chamber.

9. A method comprising:
communicating a first fluid into a mixing chamber within a microfluidic device via a first fluidic input within the microfluidic device, the first fluid comprising therapeutic mRNA;
communicating a second fluid into the mixing chamber via a second fluidic input within the microfluidic device, the second fluid comprising delivery vehicle molecules;
mixing the first fluid with the second fluid in the mixing chamber; and
communicating a third fluid from the mixing chamber via an outlet channel within the microfluidic device, the third fluid comprising a mixture of the first fluid with the second fluid.

10. The method of claim 9, the act of mixing resulting in encapsulation of the therapeutic mRNA with the delivery vehicle molecules, the third fluid comprising the encapsulated therapeutic mRNA.

11. The method of claim 9, further comprising mixing a dilution buffer with the third fluid within the microfluidic device.

12. The method of claim 11, the dilution buffer being mixed with the third fluid within a second mixing chamber in the microfluidic device.

13. The method of claim 9, further comprising:
communicating the first fluid through a vacuum cap region in the microfluidic device before communicating the first fluid into the mixing chamber; and
removing air from the first fluid via the vacuum cap region before communicating the first fluid into the mixing chamber.

14. The method of claim 13, the vacuum cap region comprising an air-permeable membrane in the microfluidic device, the act of removing air from the first fluid via the vacuum cap region before communicating the first fluid into the mixing chamber comprising applying negative pressure to draw air through the air-permeable membrane.

15. The method of claim 9, further comprising:
communicating the second fluid through a vacuum cap region in the microfluidic device before communicating the second fluid into the mixing chamber; and
removing air from the second fluid via the vacuum cap region before communicating the second fluid into the mixing chamber.

16. The method of claim 9, the act of communicating the first fluid into the mixing chamber further comprising communicating the first fluid to a fluidic intersection via the first fluidic input, the fluidic intersection being positioned within the microfluidic device upstream of the mixing chamber;
the act of communicating the second fluid into the mixing chamber further comprising communicating the second fluid to the fluidic intersection via the second fluidic input, such that the first fluid and the second fluid each reach the mixing chamber via the fluidic intersection.

17. The method of claim 9, the second fluid further comprising ethanol.

18. The method of claim 9, the delivery vehicle molecules comprising amino-lipidated peptoid molecules.

19. A method comprising:
communicating therapeutic mRNA via a first fluid through a microfluidic device;

communicating a delivery vehicle molecules via a second fluid through the microfluidic device; and mixing the first fluid with the second fluid in the microfluidic device, the act of mixing the first fluid with the second fluid resulting in encapsulation of the therapeutic mRNA in the delivery vehicle molecules.

20. The method of claim 19, further comprising synthesizing the therapeutic mRNA before communicating the therapeutic mRNA via the first fluid through the microfluidic device.

* * * * *